United States Patent
McKenzie et al.

(10) Patent No.: US 6,548,643 B1
(45) Date of Patent: Apr. 15, 2003

(54) ANTIGEN CARBOHYDRATE COMPOUNDS AND THEIR USE IN IMMUNOTHERAPY

(75) Inventors: Ian F. C. McKenzie, Victoria (AU); Vasso Apostolopoulos, Victoria (AU); Geoff Allan Pietersz, Victoria (AU)

(73) Assignee: Austin Research Institute (AU)

( * ) Notice: Subject to any disclaimer, the term of this patent is extended or adjusted under 35 U.S.C. 154(b) by 0 days.

(21) Appl. No.: 09/593,870

(22) Filed: Jun. 14, 2000

Related U.S. Application Data

(63) Continuation-in-part of application No. 09/223,043, filed on Dec. 30, 1998, now Pat. No. 6,177,256, which is a continuation of application No. 08/833,807, filed on Apr. 9, 1997, now Pat. No. 5,989,552, which is a continuation of application No. 08/340,711, filed on Nov. 16, 1994, now abandoned.

(51) Int. Cl.[7] ............................. C07K 1/00; A61K 39/00
(52) U.S. Cl. ..................................... 530/395; 424/185.1
(58) Field of Search ..................... 424/185.1; 530/395

(56) References Cited

U.S. PATENT DOCUMENTS

| 4,720,386 A | * | 1/1988 | McCollester ................. 424/88 |
| 4,963,484 A | | 10/1990 | Kufe |
| 5,047,227 A | * | 9/1991 | Rodwell et al. ........... 424/1.49 |
| 5,053,489 A | | 10/1991 | Kufe |

FOREIGN PATENT DOCUMENTS

| AU | 4187689 | | 3/1990 |
| EP | 0308147 | | 3/1989 |
| EP | 0326111 | | 8/1989 |
| FR | 2279422 | | 3/1976 |
| JP | 71016913 | | 1/1971 |
| JP | 61112023 | | 5/1986 |
| JP | 01233219 | | 9/1989 |
| JP | 05246860 | | 9/1993 |
| WO | WO 8805054 | | 7/1988 |
| WO | WO 8907107 | | 8/1989 |
| WO | 8908711 | * | 9/1989 |
| WO | 9005142 | * | 5/1990 |
| WO | WO 91/09867 | | 7/1991 |
| WO | WO 9211033 | | 7/1992 |
| WO | WO 9306858 | | 4/1993 |
| WO | WO 9314195 | | 7/1993 |
| WO | WO 9317712 | | 9/1993 |
| WO | WO 9320841 | | 10/1993 |
| WO | WO 9321948 | | 11/1993 |
| WO | WO 9406916 | | 3/1994 |
| WO | WO 9413312 | | 6/1994 |
| WO | WO 95/18145 | | 7/1995 |
| WO | WO 96/03502 | | 2/1996 |
| WO | WO 97 11715 | | 4/1997 |
| WO | WO 97/11963 | | 4/1997 |
| WO | WO 98/37095 | | 8/1998 |
| WO | WO 00/25827 | | 5/2000 |

OTHER PUBLICATIONS

Ellis Chapter 29 in Vaccines Plotkin et al Eds, WB Saunders Co. Philadelphia, 1988, pp. 568–575.*
Okawa et al J. Immunological Methods 149:127–131 (1992).*

(List continued on next page.)

*Primary Examiner*—Hankyel T. Park
(74) *Attorney, Agent, or Firm*—Dann Dorfman Herrell and Skillman, P.C.

(57) ABSTRACT

Conjugates between whole antigen or one or more repeated subunits of an antigen and a carbohydrate polymer are described. Also described are immunogenic vaccines against disease states which contain the conjugates and methods for inducing cell-mediated immune responses. The conjugates may especially contain polymers of the carbohydrate mannose and one or more repeated subunits of human mucin or non-repeated regions of human mucin.

22 Claims, 15 Drawing Sheets

OTHER PUBLICATIONS

Figure 1:
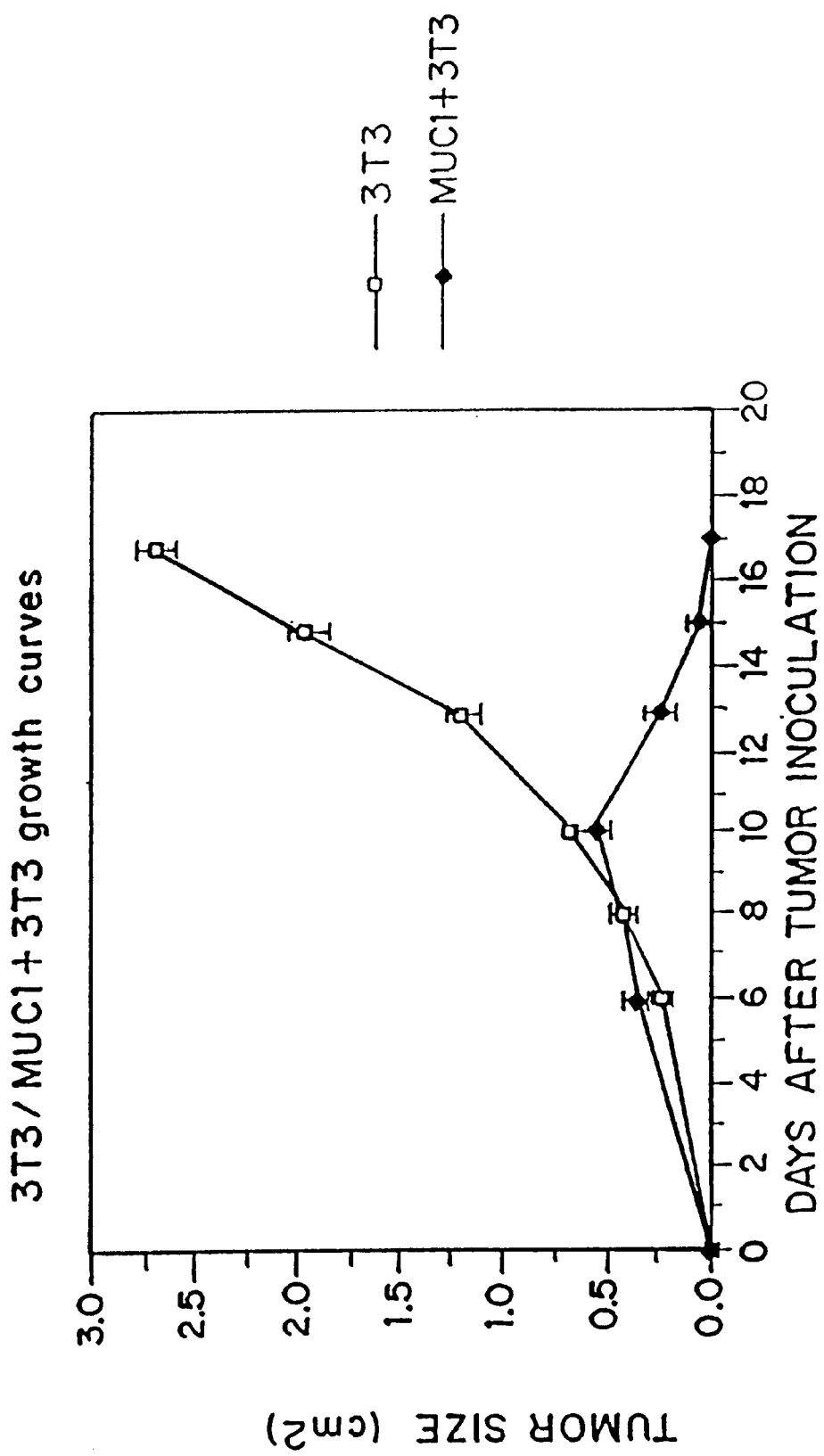

Ada in fundamentals of Immunology $2^{nd}$ Ed. Chapter 36 pp. 985–1032 William Paul Ed.*

Keith Jerome et al., Cancer Research, 51: 2908–2916 (Jun. 1, 1991).

J. Darrell Fentonot et al., Cancer Research, 53: 5386–5394 (Nov. 15, 1993).

Donna L. Barnd et al., Proc. Natl. Acad. Sci. USA, 86: 7159–7163 (Sep., 1989).

Franz–Georg Hanisch et al., J. Biol. Chem., 264: 872–883 (Jan. 15, 1989).

Keth Jerome et al., Cancer Research, 52: 5985–5990 (Nov. 1, 1992).

D. J. McCool et al., Biochemical Journal, 267: 491–500 (1990).

El–Nasir Lalani et al., J. Biol. Chem., 266: 15420–15426 (1991).

Peter L. Devine et al., Cancer Research, 51: 5826–5836 (Nov. 1, 1991).

Sheila Zrihan–Licht et al., *Eur. J. Biochem.*, vol. 224, pp. 787–795 (1994).

Michael S. Lan et al., *J. Biol. Chem.*, vol. 265, No. 25, pp. 15294–15299 (Sep. 1990).

Sandra J. Gendler et al., *J. Biol. Chem.*, vol. 265, No. 25, pp. 15286–15293 (Sep. 1990).

I. Tsarfaty et al., *Gene*, vol. 93, pp. 313–318 (1990).

Peer Bork et al., *Protein Science*, vol. 4, pp. 1421–1425 (1995).

A.P. Spicer et al., *Mammalian Genome*, vol. 6, pp. 885–888 (1995).

Daniel H. Wreschner et al., *Eur. J. Biochem.*, vol. 189, No. 3, pp. 463–473 (1990).

Geoffrey A. Pietersz et al., *Vaccine*, vol. 18, pp. 2059–2071 (2000).

T. Nurmukhamedov et al., Immunologiya, 4: 61–63 (1991) [See English abstract at p. 63].

Tracey Langsdale, Inpharma Weekly, 915: 3–4 (1993).

V. Apostolopoulos et al., Proceedings of the National Academy of Science of USA, 92: 10128–10132 (1995).

V. Apostolopoulos et al., "Production of Anti–Breast Cancer Monoclonal Antibodies Using a Glutathione–S–transferase–MUC1 Bacterial Fusion Protein", *Br. J. Cancer, 67*: 713–720 (1993).

Ding, Lei et al., "Immunogenicity of Synthetic Peptides Relates to the Core Peptide Sequence Encoded by the Human MUC1 Mucin Gene: Effect of Immunization on the Growth of Murine Mammary Adenocarcinoma Cells Transfected with the Human MUC1 Gene", *Cancer Immunology Immunotherapy, 36*: 9–17 (1993).

Denton, G., "Induction of Antibody Responses to Breast Carcinoma Associated Mucins Using Synthetic Peptide Constructs as Immunogens", *Cancer Letters, 70*: 143–150 (1993).

Hudecz, F. et al. ,"Monoclonal Antibody Binding to Peptide Epitopes Conjugated to Synthetic Branched Chain Polypeptide Carriers", *Journal of Immunological Methods, 147*: 201–210 (1992).

Okawa, Y. et al., J. Immunol. Meth., "Production of anti–peptide specific antibody in mice following immunization with peptides conjugated to mannan", 149: 127–31 (1992).

* cited by examiner

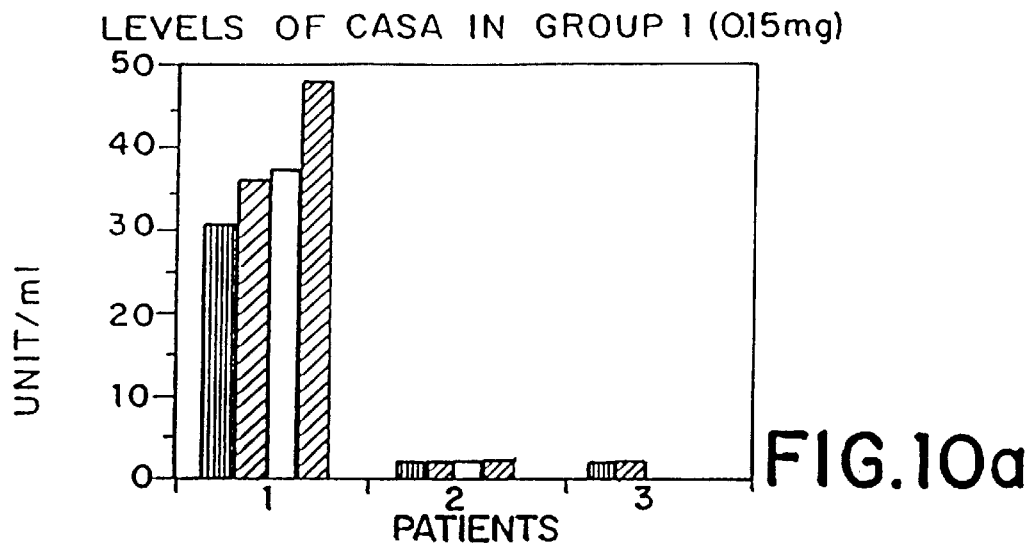
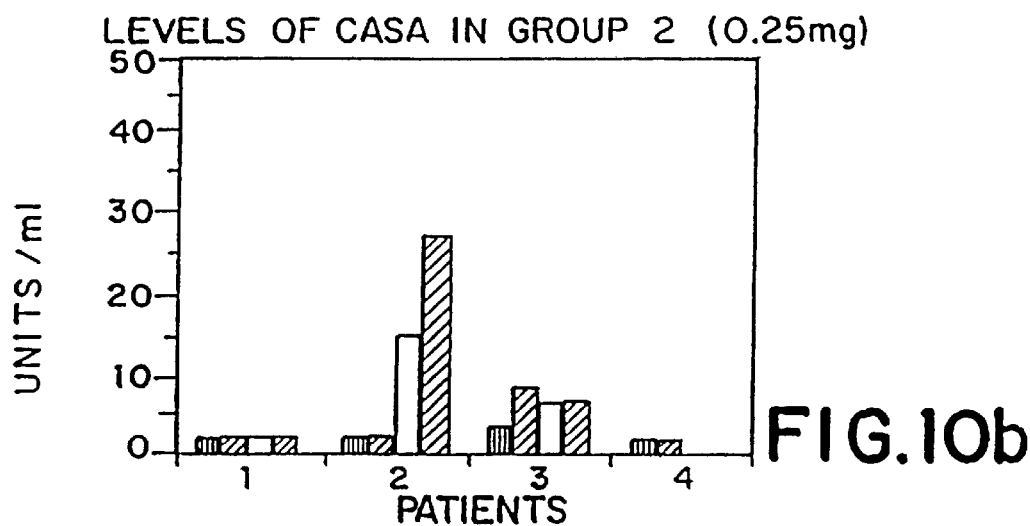
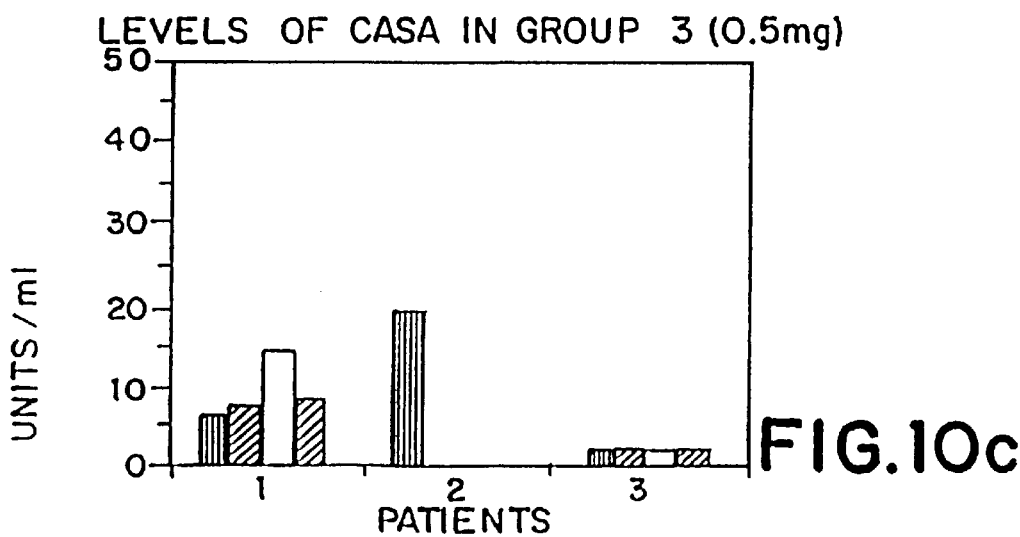

ANTIGEN CARBOHYDRATE COMPOUNDS AND THEIR USE IN IMMUNOTHERAPY

This application is a continuation-in-part application of U.S. application Ser. No. 09/223,043 filed Dec. 30, 1998 now U.S. Pat. No. 6,177,256, which is a continuation of U.S. application Ser. No. 08/833,807, filed Apr. 9, 1997, now U.S. Pat. No. 5,989,552, which in turn is a continuation of abandoned U.S. application Ser. No. 08/340,711, filed Nov. 16, 1994, all of which are herein incorporated by reference.

This invention relates to the immunotherapy of disease states, and in particular, but not exclusively to the immunotherapy of carcinomas.

Cancer is a major cause of death and severe trauma in modern society. Cancer is no respecter of persons as the young, old, males, females and peoples of all races may contract cancer, although cancer in children is relatively rare, perhaps with the exception of childhood leukemia. In western society, cancer of the colon and lung cancer are major diseases. In women, breast cancer is the most common form of cancer.

Many cancers are accompanied by overproduction of human mucin. Mucins are heavily glycosylated proteins (greater than about 100 Kd) which are produced by many epithelial cells and tumours (1). Mucins found on cancer cells are different in some respects to those on normal epithelial cells, in that some mucins have a deficiency in their carbohydrate coat which leaves the protein core exposed. (2). There are seven forms of known human mucin designated MUC1, MUC2, MUC3, MUC4, MUC5 MUC6 and MUC7 (3, 4, 26, 27). MUC1 is the most ubiquitous. The various mucins all have very similar properties, that is, they are transmembrane glycoproteins, all having a variable number of repeated amino acid sequences, which have a high content of serine, threonine and proline. Overproduction of aberrantly glycosylated mucins (either non-glycosylated or a deficiency in glycosylation) is characteristic of tumours of the breast, ovary, pancreas, colon, lungs, prostate and other tumours of secretory tissue. The cDNA sequences of the respective protein cores of the human mucins MUC1 to MUC7 have been cloned and characterized and have been found to contain highly repetitive central portions of varying numbers of repeats of particularly amino acid motifs (known as VNTR's). By way of example, MUC1 consists of unique amino and carboxyl terminal sequences separated by a highly repetitive central portion containing forty to eighty tandemly arranged copies or repeats of a twenty amino acid motif. The VNTR's of MUC1 through MUC7 are set forth below:

```
MUC1 VNTR - SAPDTRPAPGSTAPPAHGVT SEQ ID NO: 1

MUC2 VNTR - PTTTPISTTTMVTPTPTPTGTQT SEQ ID NO: 2

MUC3 VNTR - HSTPSFTSSITTTETTS SEQ ID NO: 3

MUC4 VNTR - TSSASTGHATPLPVTD SEQ ID NO: 4

MUC5 VNTR - PTTSTTSA SEQ ID NO: 5
(494 base pair insert - eight
amino acid tandem repeat)

MUC6 VNTR - 169aa repeat unit

MUC7 VNTR - TTAAPPTPPATTPAPPSSSAPPE SEQ ID NO:6
```

The repeated subunit of MUC6 comprises 169 amino acids, although at this time the amino acid sequence of this repeat unit has not been fully characterized. The MUC7 sequence has recently been published (27).

Finn and colleagues have demonstrated that in the lymph nodes of patients with breast cancer (5, 6), cancer of the pancreas, ovary and other tumours, cytotoxic lymphocytes are present which react with human mucin. Antibodies to the MUC1 peptide can block the activity of these cytotoxic T-lymphocytes on MUC1$^+$ target cells (5, 6). Recently, cytotoxic lymphocytes to a murine lung cancer have also been described (28).

The surgery associated with tumour removal is traumatic to the patient, often disfiguring, and costly. Established chemotherapeutic and radiation procedures for tumour treatment which may be carried out in place of or in conjunction with surgical procedures are often debilitating and associated with severe side-effects. There is accordingly an urgent need for therapeutic compounds and methods for the prevention/treatment of tumours.

There is an urgent need for new compounds and methods for the treatment of cancer. Similarly, there is a pressing need for alternative compounds and therapies for the treatment of other disease states such as type I allergies, malaria, HLV, dental caries, flu, cholera, foot and mouth disease, meningitis, Leishmania infection, whooping cough, rabies, Streptococcus infection, respiratory infection, measles, Lyme disease, tuberculosis, bacterial meningitis, shingles, rubella, hepatitis, herpes, hepatitis A, polio, venereal disease/trachoma, hepatitis B, common cold, cervical cancer, meningitis/pneumonitis, chicken pox, small pox, pneumonia/PUO.

In accordance with the first aspect of the present invention, there is provided a compound comprising a conjugate between an antigen and a carbohydrate polymer.

In accordance with another aspect of the present invention, there is provided a compound comprising a conjugate between the human mucin polypeptide, one or more repeated subunits thereof, or a fragment of said repeated subunits, with a carbohydrate polymer.

In a preferred embodiment of the present invention, the carbohydrate polymer is a polymer of the carbohydrate mannose.

Insofar as the present invention is concerned, the antigen can be a human autoantigen or a peptide antigen derived from a virus, microorganism or plant or an amino acid subunit of at least five amino acids in length of a human autoantigen or a peptide antigen derived from a virus, microorganism or plant. The antigen of the present invention can also consist of more than one, five or more amino acid subunits (as mentioned above) linked together. These linked subunits may be from the same or different origins within the bounds described above.

Examples of the antigens envisaged by the present invention are as follows: pollens, hepatitis C virus (HIV) core, E1, E2 and NS2 proteins, Plasmodium faliciparum circumsporozoite protein, HIV-gp1201160 envelope glycoprotein, streptococcus surface protein Ag, influenza nucleoprotein, haemagglutinin-neuraminidase surface infection, TcpA pilin subunit, VP1 protein. LMCV nucleoprotein, Leishmania major surface glycoprotein (gp63), Bordetella pertussis surface protein, rabies virus G protein, Streptococcus M protein, Syncyticial virus (RSV) F or G proteins, Epstein Barr virus (EBV) gp340 or nucleoantigen 3A, haemagglutinin, Borrelia burgdorferi outer surface protein (Osp) A, Mycobacterium tuberculosis 38 kDa lipoprotein or Ag85, Neisseria meningitidis class 1 outer protein, Varicella zoster virus IE62 and gp1, Rubella virus capsid protein, Hepatitis B virus pre S1 ag, Herpes simplex virus type I glycoprotein G or gp D or CP27, Murray valley encephalitis virus E glycoprotein, Hepatitis A virus VP1, polio virus capsid protein VP1, VP2 and VP3, chlamydia trachomatis surface protein, Hepatitis B virus envelope Ag pre S2, Human rhinovirus (HRV) capsid, papillomavirus peptides from oncogene E6 and E7, Listeria surface protein, Varicella virus envelope protein, Vaccinia virus envelope protein, Brucella surface protein, a combination of one or more of said antigens, an amino acid subunit of said antigens comprising five or more amino acids in length or combinations of one or more of said subunits.

The antigens of the present invention can also consist of whole cells or sub-cellular fractions thereof. Such cells or sub-cellular fractions thereof may be derived from any tumour type or other source. Examples of cancer types from which the whole cells or sub-cellular fractions may be derived are breast, lung, pancreas and colon cancer and melanoma. Some further examples of specific antigens obtained from tumours are melanoma specific antigen (for example, the MAGE series antigen), carcino embryonic antigen (CEA) from colon and other cancers or indeed antigens extracted from any tumour.

This invention includes any one or more of the antigens listed and in particular includes any one ore more of the human mucins MUC1 through MUC7 which, as mentioned above, all comprise highly repetitive central portions of repeated amino acid sequences which are high in serine, threonine and proline. In particular, the compounds of this invention may comprise a human mucin polypeptide (containing a variable number of repeats associated with normal allelic variation), or may comprise one or more of the repeated sequences of human mucin, preferably two to eighty, more preferably two to twenty and even more preferably two to ten repeated subunits of human mucin or it may comprise the whole native MUC1 molecule. The human mucin and subunits thereof are preferably non-glycosylated or aberrantly glycosylated so as to provoke an immune response to the mucins found on cancer cells which have a deficiency in their carbohydrate coat which leaves the protein core exposed. The use of human mucin MUC1 is particularly preferred although it is to be clearly understood that the invention extends to the use of any antigen and especially to the use of the human mucins MUC1 through MUC7. For the purpose of convenience, the term MUC will hereafter be used to refer to any of the human mucins MUC1 through MUC6 and repeated subunits thereof. While only the human mucins will be dealt with hereafter, it must be kept in mind that this invention equally relates to any other antigen as mentioned previously.

Fragments of MUC may also be conjugated to a carbohydrate polymer. These fragments would generally comprise from five to twenty amino acids from the repeated amino acid sequences of any mucins MUC1 through MUC6. For example, a fragment of the mucin MUC1 may comprise the amino acid sequence APDTR SEQ ID NO: 7, APDTRPAPG SEQ ID NO: 8, DTRPAPGSTAPP SEQ ID NO: 9, and the like. For convenience of description these fragments are also included with the definition MUC. Similarly, other antigen fragments comprising at least five amino acids may be conjugated to a carbohydrate polymer.

A specified antigen (such as MUC1, MUC2, MUC3, MUC4, MUC5, MUC6 or MUC7) may form part of a fusion protein in order to facilitate expression and purification on production of the fusion protein in recombinant host cells. The non-antigen portion of the fusion protein would generally represent the N-terminal region of the fusion polypeptide with the carboxy terminal sequences comprising antigen sequences. Fusion proteins may be selected from glutathione-S-transferase, β-galactosidase, or any other protein or part thereof, particularly those which enable affinity purification utilizing the binding or other affinity characteristics of the protein to purify the resultant fusion protein. The protein may also be fused to the C-terminal or N-terminal of the carrier protein. The nature of the fusion protein will depend upon the vector system in which fusion proteins are produced. An example of a bacterial expression vector is pGEX which on subcloning on a gene of interest into this vector produces a fusion protein consisting of glutathione-S-transferase with the protein of interest. Examples of other vector systems which give rise to fusion proteins with a protein of interest are described in Sambrook et al (7), which is incorporated herein in its entirety by reference. These can be included or cleaved; if included they could a have a "carrier" function.

The protein or fusion protein maybe expressed in a number of prokaryotic (*E. coli* or β-*sutilis*) or eukaryotic (baculovirus, CHO cells, cos cells or yeast) expression systems. In some of these systems, for example, baculovirus or yeast, by introducing glycosylation motifs into the protein or fusion protein, the mannose rich glycosylation may be adequate; negating the need for chemically linking with mannose rich carbohydrate polymers. These novel fusion proteins may be used with or without mild periodate oxidation.

The carbohydrate portion of the compounds of the invention may comprise any carbohydrate polymer, for example, selected from polymers of glucose, galactose, mannose, xylose, arabinose, fucose, glucosamine, galactosamine, rhamnose, 6-O-methyl-D-galactose, 2-O-acetyl-β-D-xylose, N-acetyl-glucosamine, iduronate, guluronate, mannuronate, methyl galacturonate, α-D-galactopyranose 6-sulphate, fructose and α abequose, conformation and configuration isomers thereof, or a carbohydrate formed of two or more different monomer units. The number of repeated monomer units in the polymer is not important but generally carbohydrate polymers would comprise at least twenty monomer units, preferably in excess of one hundred monomer units, more preferably in excess of one thousand monomer units, and still more preferably in excess of ten thousand monomer units or more. Carbohydrate polymers may be a mixture of polysaccharide chains of varying molecular weights. Most preferably the carbohydrate polymer is a polymer of mannose or is a carbohydrate polymer containing mannose units.

Antigens may be conjugated to a carbohydrate polymer according to standard processes well known in the art of carbohydrate chemistry for the derivatization and reaction of polysaccharides and monosaccharides. Carbohydrates may be oxidized with conventional oxidizing reagents such as sodium periodate to give a polyaldehyde which is then directly reacted with the antigen (such as repeated subunits of MUC1) where amino functional groups on the protein chain (such as the ε group of lysine) react with the aldehyde groups which may optionally be further reduced to form a Schiff base. Polysaccharide chains may be first activated with cyanogen bromide and the activated polysaccharide then reacted with a diamine, followed by conjugation to the antigen to form a conjugate which may optionally then be oxidized. The carbohydrate and polypeptide may be derivatized with bifunctional agents in order to cross-link the carbohydrate and polypeptide. Commonly used cross-linking agents include 1,1-bis(diazoacetyl}-2-phenylethane, glutaraldehyde, N-hydroxysuccinimide esters, for example, esters with 4-azidosalicyclic acid, homobifunctional imidoesters including disuccinimidyl esters such as 3,3'-dithiobis(succinimidyl-propionate), and bifunctional maleimides such as bis-N-maleimido-1, 8-octane. Derivatizing agents such as methyl-3-[(p-azido-phenyl)dithio] propioimidate yield photactivitable intermediates which are capable of forming cross-links in the presence of light. Oxidized carbohydrates may be reacted with hydrazine derivatives of antigens to give a conjugate. Alternatively, carbohydrates may be reacted with reagents such as carbonyl diimidazole, which after oxidation gives the desired conjugate.

The coupling of antigens to a carbohydrate involves converting any or all of the functional groups on the carbohydrate to reactive groups and thereafter reacting the reactive groups on the carbohydrate with reactive groups on the polypeptide. Carbohydrate polymers are replete with hydroxide groups, and in some instances, carboxyl groups (such as in idruionate), ester groups (such as methylgalacturonate) and the like. These groups may be activated according to standard chemical procedures. For example, hydroxyl groups may be reacted with hydrogen halides, such as hydrogen iodide, hydrogen bromide and hydrogen chloride to give the reactive halogenated polysaccharide. Hydroxy groups may be activated with phosphorous trihalides, active metals (such as sodium ethoxide, aluminium isopropoxide and potassium tert-butoxide), or esterified (with groups such as tosyl chloride or acetic acid) to form reactive groups which can be then be reacted with reactive groups on the polypeptide to form one or more bonds. Other functional groups on carbohydrates apart from hydroxyl groups may be activated to give reactive groups according to well known procedures in the art.

Polypeptides comprising MUC or other antigens may be produced according to well known procedures such as peptide synthesis, protein purification, or expression of polypeptides in host cells. Peptide synthesis may be employed for polypeptides containing up to about a hundred amino acids (for example, five repeated subunits of MUC1). Generally, for polypeptide containing about twenty or more amino acids, the preferred means of production is recombinant expression in a host cell, preferably a prokaryotic host cell, and more preferably a bacterial host cell. However, as discussed earlier, eukaryotic systems may also be used. Procedures for expression of recombinant proteins in host cells are well established, see, for example, Sambrook, et al (7).

Carbohydrates may be purified from natural sources or synthesized according to conventional procedures. Carbohydrates are available commercially from many suppliers. For example, the antigens of the invention may be coupled to keyhole limpet hemacyanin (KLH) using glutaraldehyde and then reacted with oxidised mannan.

In another aspect, the invention relates to an immunogenic vaccine against human disease states and in particular against tumour cells expressing human mucin or a subunit thereof, which comprises a compound comprising a conjugate between an antigen and a carbohydrate polymer, in association with a pharmaceutically acceptable carrier. Antigens which may be used in this aspect of the invention are as previously described. The vaccine is administered to human patients to protect against various disease states including cancer cell growth, and in particular, the growth of tumours of secretory tissues, such as tumours of the breast, colon, lung, pancreas, prostate, and the like. Patients may be immunized with the vaccine to protect against tumour formation of secretory tissues. Alternatively, patients suffering from tumours may be immunized with the vaccine as part of a therapeutic regimen for tumour treatment. By way of example, to protect women from breast cancer, women may be immunized with the vaccine pre- or post-puberty and may receive one or more injections, preferably an initial immunization, followed by one or more booster injections separated by several months to several years. In one immunization schedule, women may be immunized with the compounds of the invention and then receive a booster immunization at appropriate intervals. Further booster immunizations are then provided at regular intervals. The route of immunization is no different from conventional human vaccine administration. Accordingly, vaccines may be administered subcutaneously, intramuscularly, orally, intravenously, and the like.

In a particularly preferred aspect the invention provides a immunogenic vaccine against tumour cells expressing human mucin which vaccine comprises a conjugate between whole human milk fat globule antigen (HMFG) and a carbohydrate polymer in association with a pharmaceutically acceptable carrier.

Some other disease states which may be protected against in this manner include, type I allergies, malaria, HIV, dental caries, flu, cholera, foot and mouth disease, meningitis, Leishmania infection, whooping cough, rabies, Streptococcus infection, respiratory infection, measles, Lyme disease, tuberculosis, bacterial meningitis, shingles, rubella, hepatitis, herpes, hepatitis A, polio, venereal disease/trachoma, hepatitis B, common cold, cervical cancer, meningitis/pneumonitis, chicken pox, small pox, pneumonia/PUO.

The amount of compounds of the invention or compositions thereof delivered to a patient is not critical or limiting. An effective amount of a compound of the invention is that which will stimulate an immune response against the antigen component. The amount of compounds or compositions delivered may vary according to the immune status of the patient (depending on whether the patient is immunosuppressed or immunostimulated), the judgement of attending physician or veterinarian whether the compound is used as a vaccine to prevent or treat a disease state or as a vaccine to prevent tumour formation, or whether the vaccine is used in the treatment of an existing tumour. By way of example, patients may receive from 1 $\mu$g to 10,000 $\mu$g of the compounds of the invention, more preferably 50 $\mu$g to 5,000 $\mu$g, still more preferably 100 $\mu$g to 1,000 $\mu$g, and even more preferably 100 $\mu$g to 500 $\mu$g of the compounds of the invention. Adjuvants are not generally required. However, adjuvants may be used for immunization. Suitable adjuvants include alum, as well as any other adjuvant or adjuvants well known in the vaccine art for administration to humans.

Compounds of the invention may be administered to patients in concert with a cytokine or other immune regulator. By way of example, immune regulators which may be administered in concert with the compounds of the invention include one or more of GM-CSF, G-CSF, M-CSF, TNF$\alpha$ or $\beta$, interferon $\alpha$ or $\gamma$, any of IL1 through IL13, or any other cytokine. The immune regulator may be administered at the same time as the compounds of the invention, optionally as part of a multi-component administration form. Alternatively, the compounds of this invention and immune regulators may be administered at different time intervals.

In a still further aspect of this invention, there is provided a method for inducing a cell mediated immune response against antigens which comprises administering to an animal (including a human) a compound comprising a conjugate between said antigen and a carbohydrate polymer, optionally in association with a pharmaceutically acceptable carrier.

The immunization of humans and animals with the compounds of this invention may provoke a potentiated cellular response of activated T-lymphocytes which are cytotoxic to cells expressing the antigen component. By way of example, humans and animals may be immunized against tumours which express human mucins. A potential benefit of this invention arises from the fact that animals may be protected against cancer prior to tumour growth, as the compounds of the invention may provoke a cellular immune response of cytotoxic T-cells which kill tumour cells expressing mucin or other antigenic determinants. This invention is applicable to the immunization against tumours of secretory tissue, such as adenocarcinomas, more particularly, tumours of the breast, ovary, pancreas, colon, lung, prostate and the like.

The compounds of the invention may also be used as therapeutic agents for the treatment of patients suffering from cancer, as a part of the overall treatment for eradication of the cancer. Thus, the compounds of the invention may be administered to patients suffering from cancer either before or after surgery to remove the tumour. Preferably the compounds are administered as part of a chemotherapeutic regime following tumour excision. In these circumstances, the compounds of the invention are administered in amounts consonant with standard chemotherapeutic regimes for the administration of cytotoxic compounds for use in tumour treatment.

The compounds of this invention can also be used In immunization for therapy or prophylaxis of other disease states as mentioned earlier.

to standard techniques or produced recombinantly. The immunogenic peptide, protein or portion thereof may be part of a fusion protein.

The immunogenic peptide, protein or portion thereof may be produced according to well known procedures such as those described earlier.

Preferably the immunogenic peptide, protein or portion thereof is derived from human mucin 1, or the amino acid sequence is based on that of a human mucin 1. More preferably the immunogenic peptide, protein or portion thereof is derived from or the amino acid sequence is based on human milk fat globule membrane antigen (HMFG).

Even more preferably the immunogenic peptide, protein or portion thereof is derived from the extracellular region or intracellular region of human MUC1.

Even more preferably the immunogenic peptide, protein or portion thereof is glycosylated. It will be understood by a person skilled in the art that one or more amino acids of the immunogenic peptide, protein or portion thereof may be suitably glycosylated.

Still more preferably the immunogenic peptide, protein or portion thereof comprises one of the following amino acid sequence or an immunogenic fragment thereof:

| | | |
|---|---|---|
| (i) | TGSGHASSTPGGEKETSATQRSSVP | SEQ ID NO: 10 |
| (ii) | RSSVPSSTEKNAVSMTSSVL | SEQ ID NO: 11 |
| (iii) | SGHASSTPGGEKETSATQRSSVPSSTEKNAVSMTSSVLSSHSPGS GSSTTQGQDVTLAPATEPASGSAATW | SEQ ID NO: 12 |
| (iv) | SAPDNRPAL | SEQ ID NO: 13 |
| (v) | NSSLEDPSTDYYQELQRDISE | SEQ ID NO: 14 |
| (vi) | TQFNQYKTEAASRVNL | SEQ ID NO: 15 |
| (vii) | AVCQCRRKNYGQLDIFPARDTYH | SEQ ID NO: 16 |
| (viii) | YVPPSSTDRSPYEKVSAGNG | SEQ ID NO: 17 |

In a still further aspect, the invention relates to the use of a compound comprising a conjugate between the human mucin polypeptide, one or more repeated subunits thereof, or a fragment of said repeated subunits and a carbohydrate polymer in the treatment of adenocarcinoma, particularly breast cancer.

The compounds of this invention possess the advantage of being substantially non-toxic on administration to animals or humans, and as a consequence the compounds are well tolerated by administration to patients.

The invention described herein is not restricted to the human mucin MUC1. The invention clearly extends to the use of other mucins expressed by cancer cells, as well as to the use of other antigens which on coupling to polysaccharides, can be used to provoke cytotoxic T-cell responses against tumour cells, which compounds may be used in vaccines to prevent tumour formation, as well as for the treatment of cancer, and/or the treatment or prophylaxis of other disease states as mentioned earlier.

In a further aspect the invention provides an immunogenic peptide, protein or portion thereof capable of eliciting an immune response comprising an amino acid sequence of non VNTR, non leader regions of mucin.

The immunogenic peptide, protein or portion thereof may be derived from natural sources, synthesized according The immunogenic peptide, protein or portion thereof may be a mutant variant or derivative of amino acid sequences (i) to (ix) above, provided it has the same or similar immunogenic properties.

The inventors' data suggest that the non-VNTR regions of MUC1 may be advantageous immunologically as they appear to steer antigen presentation towards stimulation of the cellular immune response. By contrast, the VNTR region can deviate the immune response towards antibodies due to cross-reaction with the gal antibodies. The preferential stimulation of cellular immune responses e.g. upregulation of cytotoxic T cells etc could provide efficacious and long-lasting non-VNTR vaccination which would be highly advantageous.

In accordance with a further aspect of the present invention, there is provided a compound comprising a conjugate between the immunogenic peptide, protein or portion thereof described above and a carbohydrate polymer.

In a preferred embodiment of the present invention, the carbohydrate polymer is a polymer of the carbohydrate mannose.

The immunogenic peptides, proteins or portions thereof may have amino acid sequences which are derived from or based upon antigens from any tumour type or other source expressing MUC1. Examples of cancer types from which the whole cells or sub-cellular fractions may be derived from or based upon antigens from any tumour type or other source expressing MUC1. Examples of cancer types from which the whole cells or sub-cellular fractions may be derived are breast, lung, pancreas and colon cancer. Some further examples of specific antigens obtained from tumours are carcinoembryonic antigen (CEA) from colon and other cancers or indeed antigens extracted from any tumour expressing MUC1.

Fusion proteins may be selected from those described earlier.

The carbohydrate portion of the compounds of the invention may comprise those described earlier.

Antigens in the form of the immunogenic peptide, protein or portion thereof may be conjugated to a carbohydrate polymer according to standard processes well known in the art of carbohydrate chemistry for the derivatization and reaction of polysaccharides and monosaccharides such as those described earlier.

Carbohydrates may be purified from the natural sources or synthesized according to conventional procedures. Carbohydrates are available commercially from many suppliers.

In another aspect, the invention relates to an immunogenic vaccine against disease states particularly human disease and in particular against tumour cells expressing mucin or a subunit thereof, which vaccine comprises the immunogenic peptide, protein or portion thereof described in an earlier aspect of the invention optionally with an adjuvant in association with a pharmaceutically acceptable carrier.

The adjuvant may be any suitable adjuvant known in the art such as Quil A. QS-21 Iscoms, liposomes, alum, salts, oil, emulsions, etc.

The immunogenic peptide, protein or portion thereof may also be used to pulse dendritic cells for in vivo transfer and use as a vaccine.

In yet another aspect the invention relates to an immunogenic vaccine against disease states, particularly human disease and in particular against tumour cells expressing mucin or a subunit thereof, which vaccine comprises the immunogenic peptide, protein or portion thereof conjugated to a carbohydrate polymer as described in an earlier aspect of the invention optionally in association with a pharmaceutically acceptable carrier.

In yet another aspect of the invention, there is provided a method for inducing a cell mediated immune response against mucin which comprises administering to an animal (including a human) the immunogenic peptide, protein or portion thereof described in an earlier aspect of the invention, optionally in association with a pharmaceutically acceptable carrier.

In a still further aspect of this invention, there is provided a method for inducing a cell mediated immune response against mucin which comprises administering to an animal (including a human) a compound comprising a conjugate between said immunogenic peptide, protein or portion thereof and a carbohydrate polymer as described in an earlier aspect of the invention, optionally in association with a pharmaceutically acceptable carrier.

The immunization of humans and animals with the immunogenic peptide, protein or portion thereof or carbohydrate conjugate compounds of this invention may provoke a potentiated cellular response of activated T-lymphocytes which are cytotoxic to cells expressing the antigen component as described earlier.

The immunogenic peptide, protein, portion thereof or carbohydrate conjugate compounds of the invention may also be used as therapeutic agents for the treatment of patients suffering from cancer, as a part of the overall treatment for eradication of the cancer as described earlier.

In still a further aspect, the invention relates to the use of immunogenic peptide, protein, portion thereof or a conjugate thereof with a carbohydrate polymer in the treatment of adenocarcinoma, particularly breast cancer.

The immunogenic peptide, protein, portion thereof or carbohydrate conjugate compounds of this invention possess the advantage of being substantially non-toxic on administration to animals or humans, and as a consequence the compounds are well tolerated by administration to patients.

In yet another aspect the invention provides isolated nucleic acid sequences encoding the immunogenic peptide, protein or portion thereof described in an earlier aspect of the invention and includes vectors containing such nucleic acid sequences. The nucleic acids may be used as a basis for DNA vaccines. Such nucleic acids may be generated according to standard techniques either by cloning or synthesis as in Sambrook et al (7).

In yet another aspect the invention provides a compound comprising a conjugate between native MUC1 and a carbohydrate polymer. Preferably the native MUC1 is HMFG. This provides an advantage in that a greater number of epitopes or antigens are presented. This means that the compound may be immunogenic in a larger number of people depending on their HLA subtypes. HMGF used as a basis for the compound may be isolated and purified from natural sources which include but are not limited to body fluids such as breast milk, serum and ascites. The HMFG may also be a recombinant protein preferably produced by a eukaryotic cell.

The invention will now be described with reference to the following non-limiting Examples.

The following abbreviations are used in the Examples:

ABBREVIATIONS

ELISA: enzyme linked immunosorbent assay
DTH: delayed type hypersensitivity
FP: fusion protein
GST: glutathione-S-transferase
HMFG: human milk fat globule
Kd: kilodalton
KLH: keyhole-limpet haemocyanin
PAGE: polyacrylamide gel electrophoresis
PBS: phosphate buffered saline
SDS: sodium dodecyl sulphate
Tc: cytotoxic T-lymphocytes
VNTR: variable number of tandem repeats
CTL: cytotoxic T-cells
M-FP: mannan fusion protein
MHC: major histocompatability complex
MSA: mucin serum antigen
CASA: circulating MUC1 serum antigen

FIGURE LEGEND

FIG. 1: Growth of $5 \times 10^6$ 3T3 and MUC1$^+$3T3 cells is BALB/c mice.

Figure 2A:
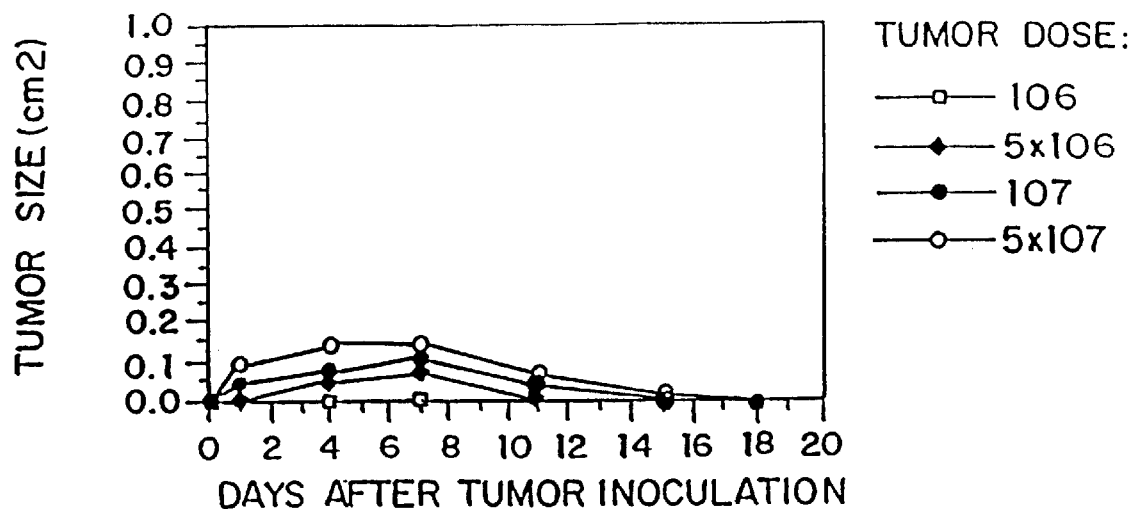

FIG. 2: Dose response of MUC1$^+$3T3 cells in (a) mannan-fusion protein and (b) non immunized BALB/c mice. Doses ranging from $10^6$–$5 \times 10^7$ cells.

FIG. 3: Mice immunized with (a) mannan, mixture of mannan+fusion protein, M-FP and a control group (immunized with PBS); (b) 161FP-mannan, oxidized mannan, pure M-FP, M-FP and PBS; (c) dextran-FP (D-FP), M-FP and PBS, and challenged with $10^6$ MUC1$^+$3T3 cells.

Figure 4:
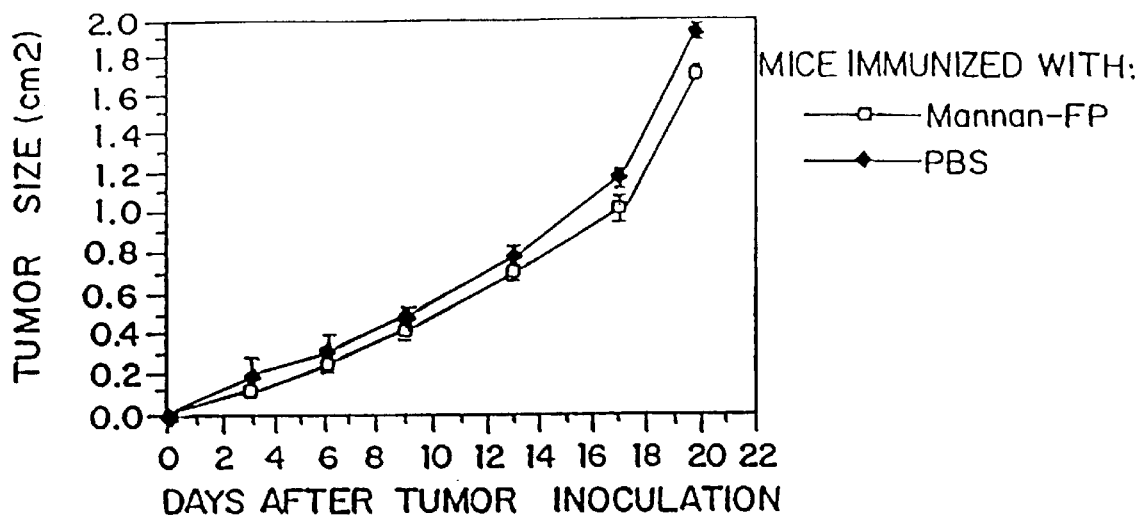

FIG. 4: Mice immunized with M-FP protein and a control group immunized with phosphate buffer and challenged with 10⁶313 cells.

Figure 5:
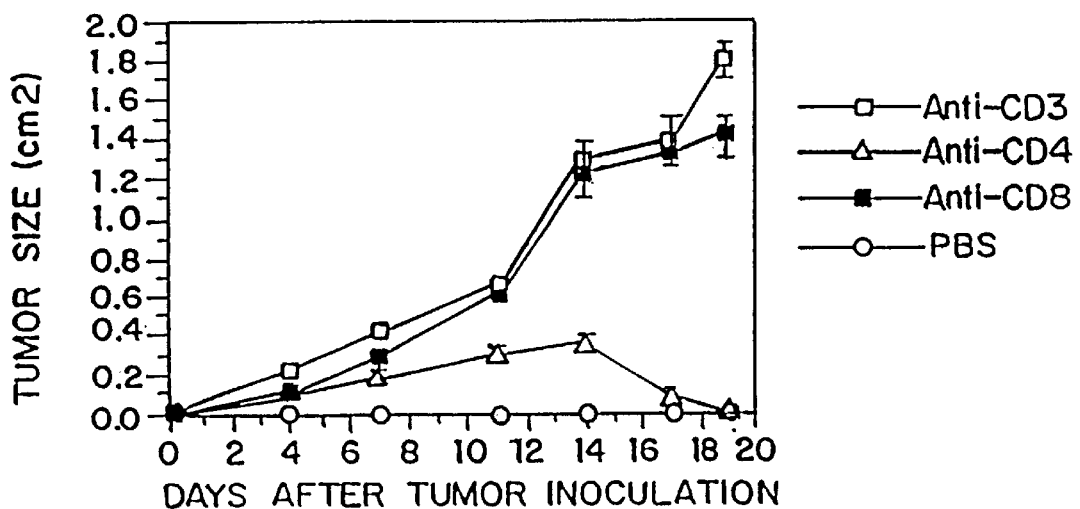

FIG. 5: BALB/c mice treated with anti-CD3, anti-CD4 and anti-CD8 on −2, 0, +2 days. Challenge with $10^6$ MUC1⁺ 3T3 cells.

Figure 6:
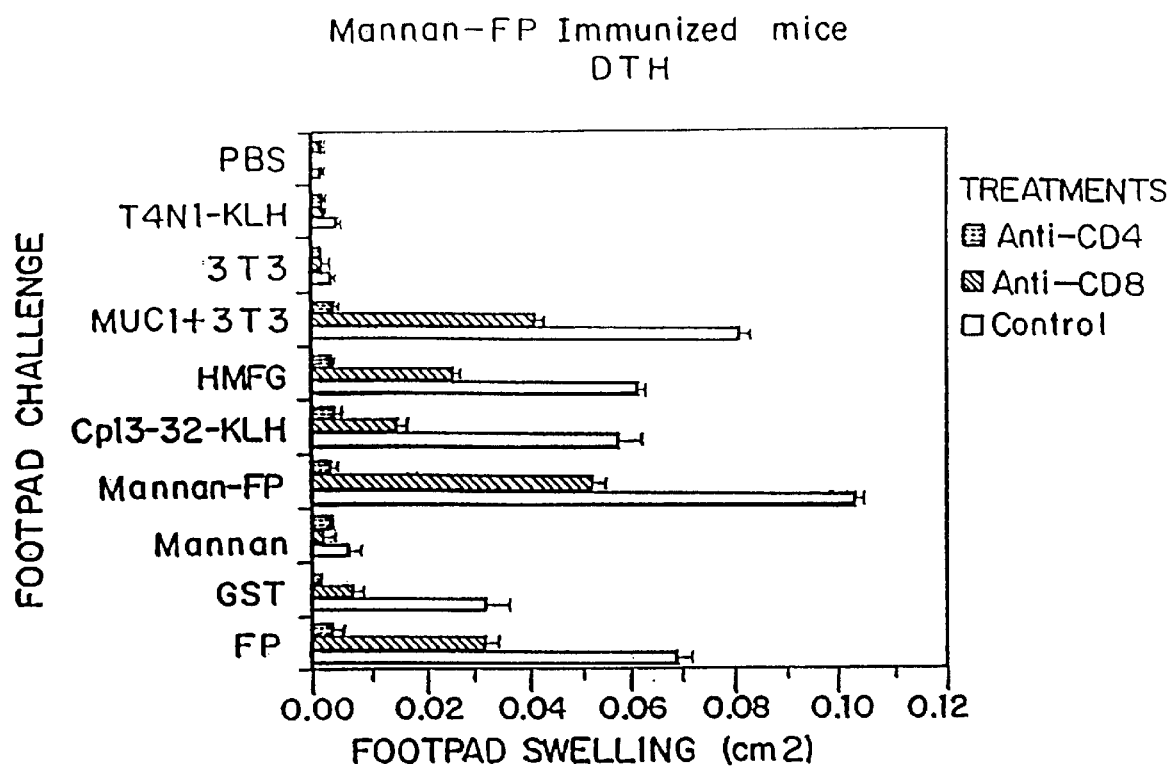

FIG. 6: DTH response measured at forty-eight hours in mice immunized with mannan-fusion protein and challenged with dead 3T3 and MUC1⁺3T3 cells, Cp13–32-KLH, fusion protein, HMFG, mannan-fusion protein, GST, T4N1 and PBS in their hind footpads. Control (open box), mice treated with anti-CD4 (grey box) and mice treated with anti-CD8 (cross lines).

Figure 7:
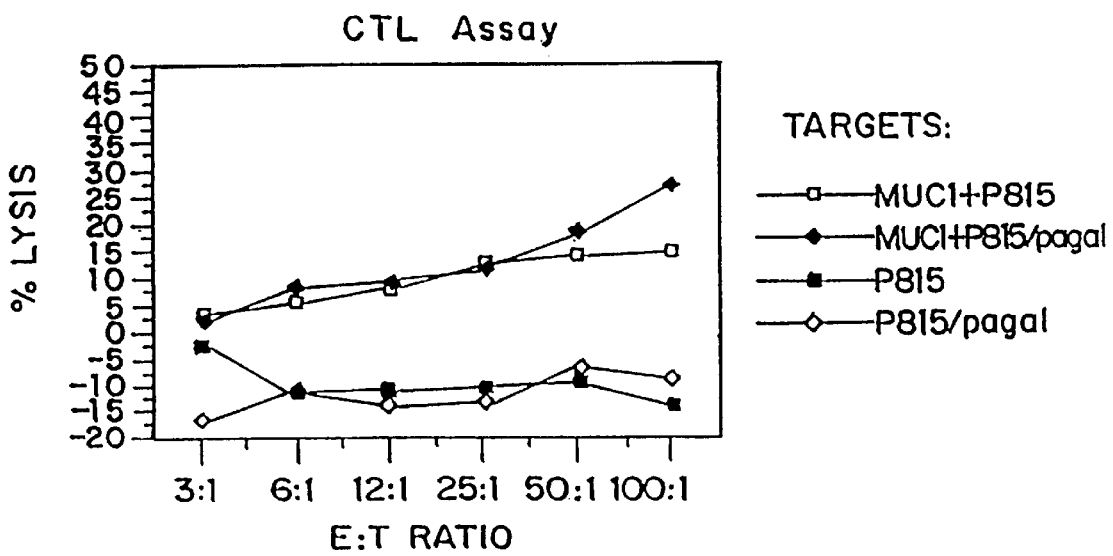

FIG. 7: Cytotoxic T-lymphocyte assay with P815±pagal and MUC1⁺P815±pagal treated target cells.

FIG. 8: A: (DBA/2⁺⁺×BALB/c)F1 mice were challenged with 5×10⁶ MUC1⁺P815 cells. After thirteen days of tumour challenge (established tumours) mice were immunized with 5 μg M-FP (5 μg corresponding to the amount of FP) once or every other day. Control mice were injected with PBS;

B: DBA/2⁺⁺ mice were challenged with 5×10⁶ MUC1⁺ P815 cells. After fifteen days of tumour challenge (established tumours) mice were immunized with 5 μg M-FP (5 μg corresponding to the amount of FP) once or every other day. Control mice were injected with PBS.

FIG. 9: A, B and C—the figures show the level of mammary serum antigen (MSA) in the serum of patients. The vertical axis gives the level (unity/ml) according to the manufacturer's instructions, the horizontal axis refers to different patients.

A: dose (0.15 mg) patients 1,2 and 3;

B: dose (0.25 mg) patients 1 to 4;

C: dose (0.5 mg) patients 1 to 3.

FIG. 10: A, B and C—the figures show the level of cancer associated serum antigen (CASA) in the serum of patients. The vertical axis gives the level (immunity/ml) according to the manufacturer's instructions, the horizontal refers to different patients.

A: dose (0.15 mg) patients 1,2 and 3;

B: dose (0.25 mg) patients 1 to 4;

C: dose (0.5 mg) patients 1 to 3.

FIG. 11: A, B, C, D and E—the figures show the antibody titres (measured as OD=optical density) in ELISA assays to different antigens.

A: anti-FP=fusion protein;

B: anti-DT=diphtheria toxoid;

C: anti-HMFG=human milk fat globular proteins;

D: anti-Cp13 to 32=anti-MUC1 peptide;

E:=anti-STPA (control, non-reactive peptide).

The groups are as in the preceding figures. That is, group 1=0.15 mg peptide injected, group 2=0.25 mg peptide injected, group 3=0.05 mg peptide injected, and the numbers are the patients (in this case 1 to 10). The bar code is shown on the figure for each patient injected before and at three times after immunizations.

Figure 12A:
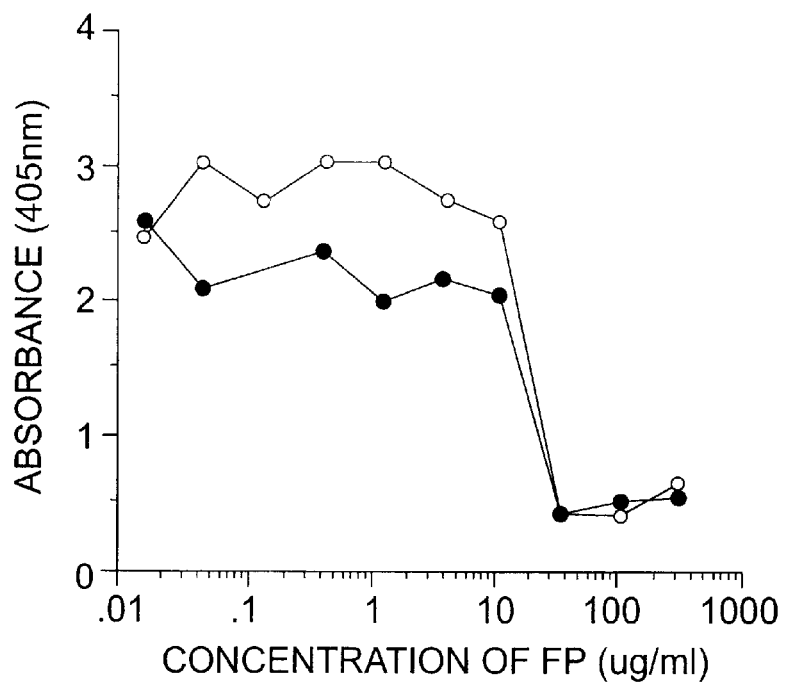

FIG. 12 Assay for HMFG and mannan. (a) Inhibition of binding of anti-MUC1 antibody to HMFG by competitor preparations of HMFG (m) and mannan-HMFG (l). (b) Binding of mannan-HMFG (l) and HMFG (m) to anti-MUC1 antibody and Con A detected by a radioimmunoassay.

Figure 13:
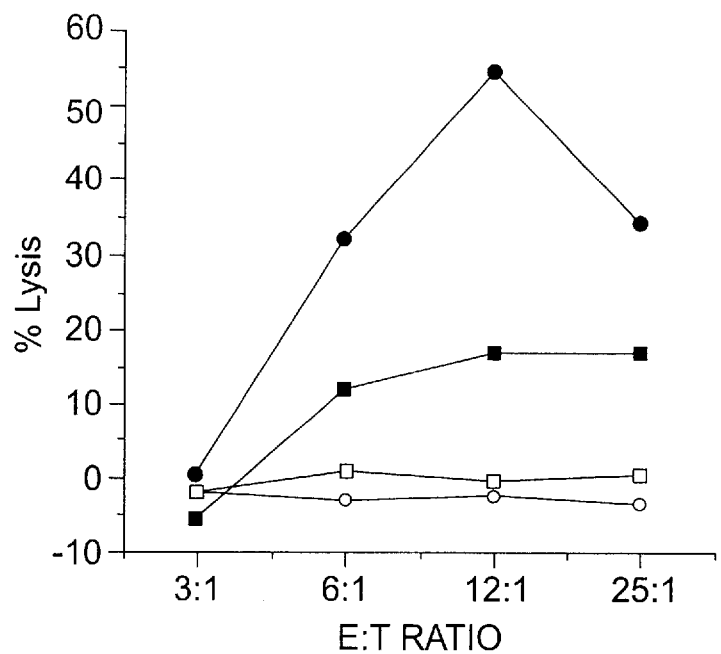

FIG. 13 A2K^b MUC1 double transgenic mice were immunised with mannan-HMFG and splenocytes were used in CTL assays. Cytotoxic activity of the effector cells were measured on ⁵¹Cr-labelled MCF7 with (n) or without cold K562 (l); BT20 (p) or ME272 (m).

FIG. 14 C57BL/6 and BALB/c mice were immunised with mannan-HMFG and splenocytes were used in CTL assays. Lysis of P815 (a) or RMA (c) cells pulsed with various 9-mer peptides from the intracellular peptide 471–493; Lysis of P815 (b) or RMA (d) cells pulsed with various 9 mer peptides from the extracellular peptides 33–103 and 51–70 and (e) Lysis of P815 cells pulsed With YYQELQRDI SEQ ID NO: 18 and RMA-MUC1 cells pulsed with SAPDNRPAL SEQ ID NO: 13. As controls for peptide pulsing and antigen-specific cell lysis, known peptide antigens were used and are shown in each panel and described in the text.

| PEPTIDE | AMINO ACID SEQUENCE |
|---|---|
| MUC1 VNTR Cp13–32 | C-PAHGVTSAPDTRPAPGSTAP SEQ ID NO: 19 |
| Fusion protein | (PAH GVTSAPDTRPAPGSTAP) × 5-GST SEQ ID NO: 20 |
| N-terminal region to MUC1 | |
| p31–55 | TGSGHASSTPGGEKETSATQRSSVP SEQ ID NO: 10 |
| p51–70 | RSSVPSSTEKNAVSMTSSVL SEQ ID NO: 11 |
| C-terminal to MUC1: | |
| p334–364 | NSSLEDPSTDWQELQRDISE SEQ ID NO: 14 |
| p408–423 | TGFNQYKTEAASRVNL SEQ ID NO: 15 |
| Mouse CD4:T4N1 | KTLVLGKEQESAELPCEY SEQ ID NO: 21 |

Figure 15:
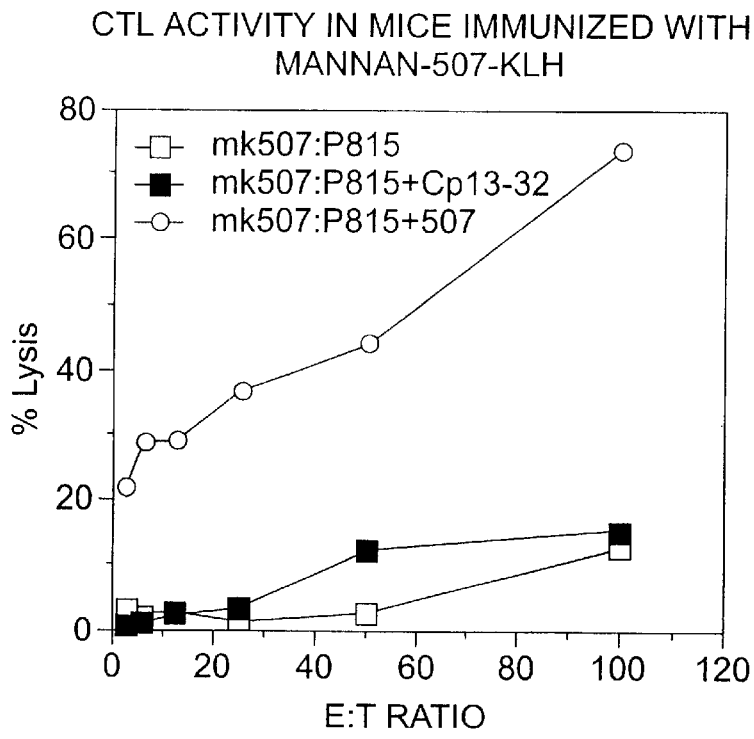

FIG. 15 Balb/c mice were immunised with mannan-507-KLH and splenocytes were used for CTL assays. The % lysis of ⁵¹Cr-labelled P815 target cells unpulsed or pulsed with Cp13–32 or 507 peptide at various effector:target ratios were measured.

Figure 16:
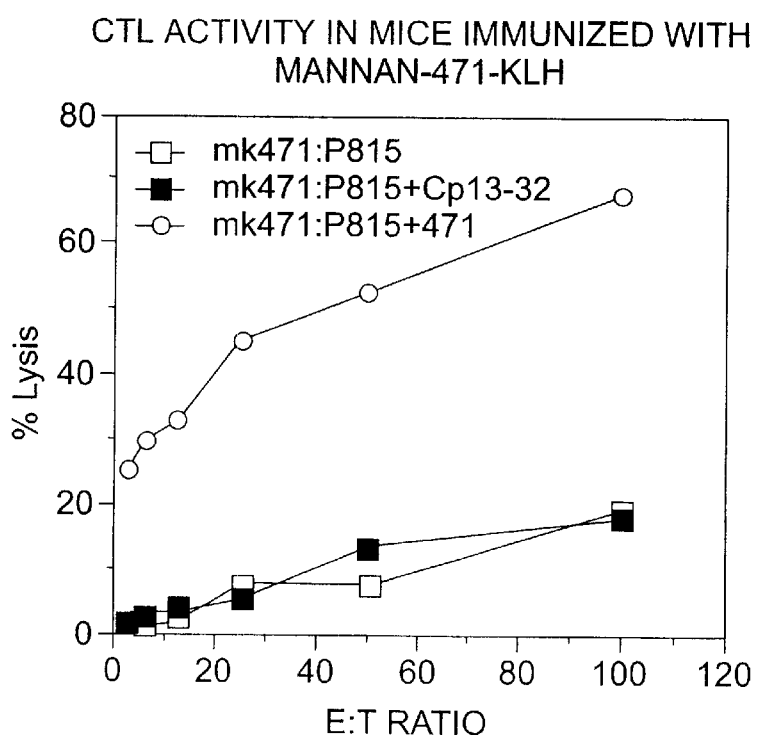

FIG. 16 Balb/c mice were immunised with mannan-471-KLH and splenocytes were used for CTL assays. The % lysis of ⁵¹Cr-labelled P815 target cells unpulsed or pulsed with Cp13–32 or 471 peptide at various effector:target ratios were measured.

EXAMPLE 1

Materials and Methods

Synthetic peptides, fusion protein, and HMFG production and immunization:

Peptides C-p13–32 (MUC1 VNTR), p31–55 and p51–70 (N-terminal to VNTR) and p344–364 and p408–423 (C-terminal to VNTR) were synthesized using an Applied Biosystems Model 430A automated peptide synthesizer (sequences shown in Table 1).

The mouse CD4 N-terminal region peptide (T4N1) was also synthesized and used as a negative control peptide (Table 1). HMPG, was isolated from human milk (8). A fusion protein (9) containing 5 VNTR repeats was produced by subcloning the cDNA into the bacterial expression vector pGEX-3X (10) (Table 1).

BALB/c mice (females aged eight weeks) were immunized intraperitoneally with 50 μg of either fusion protein, HMFG, C-p13–32 (coupled to diphtheria-toxoid with glutaraldehyde) or T4N1 (coupled to diphtheria toxoid) emulsified in complete Freund's adjuvant and this was repeated four and six weeks later in phosphate buffered saline.

Prior to tumour injection and after tumour rejection mice were bled and the serum was tested on an ELISA for antibody production against the relevant immunogens.

MUC1+3T3 tumour injections (see later description for production of these cells) were given subcutaneously in 0.2 mls containing the appropriate tumour dose. Mice treated with anti-CD3, anti-CD4, anti-CD8 and anti-γ-interferon antibodies were given three intraperitoneal injections of 0.2 mls on days −2, 0 and +2 (0=day of tumour injection). Mice to be treated with antibody were injected subcutaneously with the tumour on day zero and on day five (tumour size approximately 0.15 cm$^2$) when they were treated with rabbit complement (fresh serum −0.2 mls intravenously) and antibody (0.2 mls intraperitoneally), on days five and seven.

TABLE 1

Sequences of synthetic peptides

| Peptide | Amino Acid Sequence |
| --- | --- |
| MUC1 VNTR: Cp13–32 Fusion protein N-terminal region to MUC1: | C-PAHGVTSAPDTRPAPGSTAP (PAHGVTSAPDTRPAPGSTAP) × 5-GST |
| p31–55 p51–70 C-terminal to MUC1: | TGSGHASSTPGGEKETSATQRSSVP RSSVPSSTEKNAVSMTSSVL |
| p334–364 p408–423 Mouse CD4: T4N1 | NSSLEDPSTDVVQELQRDISE TGFNQYKTEAASRVNL KTLVLGKEQESAELPCEY |

Treatment of mice with antibodies:

To ensure that the antibodies to CD3, CD4 and CD8 were depleting or blocking CD3+, CD4+ and CD8+ T-cells, a serological analysis of residual cells was performed using the antibodies to CD3, CD4 and CD8. Spleen and lymph node cells were removed from normal and treated BALB/c mice, the lymphocytes were teased, washed in DME and incubated at 37° C. for five minutes in 0.83% ammonium chloride to lyse red blood cells. Serology tests were performed where 2×10$^5$ spleen/lymph node cells from mice were added to a 1:500 dilution of anti-CD3, anti-CD4 and anti-CD8 ascites. Following extensive washing, the cells were incubated with (mouse thymus cell absorbed) rat anti-mouse IgG and incubated for thirty minutes on ice. Mice which had been treated with anti-CD3, anti-CD4, anti-CD8 or anti-CD4+CD8 were each tested with these antibodies. It was found that the CD3+ cells were depleted and CD4+ and CD8+ cells had been blocked.

Preparation of soluble GST-MUC1 fusion protein

A 309 base pair insert (PDF9.3) encoding a little more than 5 repeats of a 60 base pair motif from the VNTR region of MUC1 cDNA (10) was subcloned into the bacterial expression vector pGEX-3X, in the correct reading frame and orientation (11). Fusion protein (FP), consisting of glutathione-S-transferase (GST, 26 Kd) and MUC VNTR (12 Kd)was induced with 0.1 mM IPTG (11) Cells were collected by centrifugation, washed and lysed by sonication in buffer containing 1% (v/v) Triton X-100. Supernatant containing the soluble FP was mixed with glutathione-agarose beads (sulphur-linked) (Sigma, St. Louis) and collected by centrifugation. The FP ((C-PAHGVTSAPDTRPAPGSTAP)×5-GST SEQ ID NO: 20) was eluted with buffer containing 5 mM reduced glutathione, dialyzed against phosphate buffered saline and analysed by SDS-PAGE.

Polyacrylamide gel electrophoresis: Samples to be tested were mixed with SDS sample buffer, boiled for five minutes and then loaded onto a 12.5% SDS-PAGE gel. Gels were stained in 0.2% Coomasie blue and then destained in 7% acetic acid or were silver stained (16). Molecular weight markers used: 200,000 myosin; 116,000 β-galactosidase; 92,500 phosphorylase b: 66,200 Bovine serum albumin; 43,000 Hen egg white ovalbumin; 31,000 Bovine carbonic anhydrase; 21,500, Soybean trypsin inhibitor, and 14,400 Hen egg white lysozyme.

Conjugation of Mannan to MUC1 fusion protein

Mannan was oxidized to a poly-aldehyde by treating 14 mg of mannan (a mannose containing polysaccharide) in 1 ml of 0. 1M phosphate buffer pH6.0 to pH9.0 with 100 μl 0.1M sodium periodate in phosphate buffer for one hour at 4° C. Following a further 30 minute incubation at 4° C. with 10 μl ethandiol, the mixture was passed through a PD10 column and the mannan fraction collected; 230 μg of MUC1 FP was added to the oxidized mannan, reacted overnight at room temperature and used for subsequent studies.

The fusion protein was radiolabelled with 125, using chloramine-T. The unlabelled fusion protein was mixed with radiolabelled fusion protein such that the specific activity was 1×10$^7$ cpm/μg and reacted with oxidized mannan as above. The mannan-FP was stabilized by reducing the Schiffs bases and residual aldehyde groups. The complex was then analysed by SDA-PAGE, Western blot analysis and by gel permeation chromatography using sepharyl S-208 column (1.5 cm×100 cm).

Immunization schedule

BALB/c mice (females aged eight weeks) were immunized intraperitoneally with 5 μg (corresponding to amount of FP) mannan-FP, FP and a mixture of non-conjugated mannan+FP in phosphate buffered saline (PBS) once weekly for three weeks. Mice were previously immunized with FP alone and this was used for a control for antibody production (see below). Prior to tumour injection, mice were bled and the serum tested by ELISA (see below) for antibody production against FP, (anti-mannan antibodies).

Tumours and antibodies

The BALB/c mouse fibroblast cell line 3T3 transfected with the MUC1 cDNA transmembrane form with the ras gene and a cell line MUCL+3T3 was developed (obtained from Dr D Wreschner, Tel Aviv University, Israel). Mice received a 0.2 ml subcutaneous injection of appropriate tumour cell dose in PBS and subsequent tumour growth measured. All measurements were performed with dial gauge callipers (Schnelltaster, H C Kroplin, Hessen, Germany) and the size of the tumours were expressed by the area of the tumour size (cm$^2$) (diameter×diameter). The murine DBA/2 mastocytoma cell lines P815, and MUC1+ P815 (containing the cDNA of the membrane anchored form of MUC1) were obtained from Dr B Acres (Transgene, Strasbourg, France).

Rat Mabs to murine CD3 (KT3.2), CD4 (H129.19) and CD8 (536.72) were prepared from ascites and tissue culture supernatants (12 to 14). Ascites fluid were prepared in SCID mice as described previously (15). Mice treated with anti-CD3, anti-CD4 and anti-CD8 antibodies were given three intraperitoneal injections of 0.2 mls on days −2, 0 and +2 (0=day of tumour injection). MUC1 antibodies used were VA1 and VA2, produced against a GST-MUC1 bacterial FP which contains five VNTR repeats (16).

Preparation of peptides and HMFG

Peptides C-p13–32 (C-PAHGVTSAPDTRPAPGSTAP SEQ ID NO: 19) (MUC1 VNTR) and T4N1 (KTLVLGKEQESAELPCEY SEQ ID NO: 21) (mouse CID4 N-terminal region peptide) were synthesized using an Applied Biosystems Model 430A automated peptide synthesizer. HMFG was isolated from human milk and prepared as previously described (17).

Enzyme linked immunosorbent assay (ELISA)

(a) Measurement of anti-fusion protein antibody: The ELISA test was performed (17), where 20 μg/ml of FP was coated in the wells of a microtitre plate, non-specific binding blocked with 2% bovine serum albumin, and 50 μl of serum from FP and mannan-FP immunized mice added for two hours at room temperature. Normal mouse serum (NMS) was used as negative control. After washing, sheep anti-mouse immunoglobulin conjugated to horseradish peroxidase conjugate (Amersham, United Kingdom) was added, incubated at room temperature and the plate was developed using 50 μl, 0.03% 2,2'-azino-di(3-ethylbenzthiazoline sulphonate (Amersham, United Kingdom), 0.02% $H_2O_2$(100 Volume, Ajax Chemical) in 0.1M citrate buffer, pH4.0 and incubated for ten to fifteen minutes at room temperature until the desired intensity was achieved. Absorbency was read at 405 nm in a plate reader.

(b) Determination of the activity of fusion protein after conjugation to mannan: The ELISA test was performed as described above with the following modifications; 20 μl/ml of FP, mannan-FP and mannan were coated on the plate and the primary antibodies used were VA1 and VA2 (anti-FP Mabs).

Induction of DTH

To induce DTH in mice, cyclophosphamide (Endoxan-Asta, Mead Johnston) at a dosage of 200 mg/kg body weight, was injected into the peritoneal cavity two days before an intraperitoneal injection of 5 μg mannan-FP. Six days later, the hind footpads were injected (20 μl) with either $10^5$3T3 or MUC1$^+$3T3 (freeze/thawed five times), 50 μg of HMFG, FP. C-p13–32 (coupled to keyhole-limpet haemocynin using glutaraldehyde), T4N1 (an irrelevant peptide), mannan-FP, GST and mannan and an equivalent volume of PBS. The DTH response was measured at forty eight hours later, by measuring the width and the thickness of the footpad and calculating their product. All measurements of footpads were performed with dial gauge callipers (Schnelltaster, H C Kroplin, Hessen, Germany).

Cytotoxic T-lymnhocyte assay

BALB/c mice immunized with mannan-FP were sacrificed and their spleen cells were collected and washed in 2% foetal calf serum/PBS. The target cells, P815 and MUC1$^+$P815 cells were either not treated or treated with 5 mM phenyl N-acetyl-a-Dgalactosaminide (pagal) for two days (to inhibit O-linked glycosylation) (Sigma, St Louis, USA) prior to use in a standard $^{51}$Cr release assay. Tumour cells ($10^6$ cells) (target cells) were radiolabelled with 100 μCi of $Na_2^{51}CrO_4$ (Amersham Corp. Arlington Heights) for sixty minutes at 37° C., followed by extensive washing. Spleen cells and target cells, were resuspended in culture medium, and then combined at various effector-to-target ratios in 96-well, U-bottom plates (Costar Corporation). The plates were then centrifuged at 100×g for three minutes to initiate cell contact and incubated for four hours at 37° C. in 10% CO2. After incubation the supernatants were collected and radioactivity was quantitated in a gamma counter (Beckman Instruments).

Spontaneous release of $^{51}$Cr was determined by incubation of the target cells alone, while maximum release of $^{51}$Cr was determined by treatment with 10% sodium-dodecyl sulphate and percentage of specific release was determined as [(experimental-spontaneous)/(maximum-spontaneous)]× 100%.

T Proliferation Assay

Mice immunized with M-FP were sacrificed, their spleen cells were collected, washed in 2% foetal calf serum/PBS, red blood cells lysed with 0.14% $NH_4Cl$ and duplicate cultures of $5 \times 10^5$ spleen cells in 100 μl of culture media were seeded in a 96-microwell plate. Spleen cells were stimulated with 100 μl of the following: 10 μg—T4N1, GST, mannan, HMFG, Cp13–32, FP, MFP; and $10^5$ breast cancer cells (pagal treated and untreated) of –3T3, MUC1$^+$3T3, P815, MUC1$^+$P815, and $10^5$ human breast cancer cell lines—T47D, MCF7 and ZR15. All tumour cells were treated with 25 μg/ml of mitomycin-C (Sigma, Victoria Australia) for two hours at 37° C. to inhibit proliferation of the tumour cells. Cultures were incubated at 37° C. in 5% CO2 for thirty six hours. $^3$[H]TdR (Amersham, United Kingdom) (6.7 Ci/mmol) incorporation was determined during the last four hours of culture (1 μCi/well).

EXAMPLE 2

Serological Analysis of MUC1$^+$3T3 Cells

In vitro MUC1$^+$3T3 cells did not appear to be different to normal 3T3 cells as they had the same appearance and growth characteristics. By serological analysis, MUC1$^+$3T3 cells expressed high concentrations of MUC1 and were H-2$^{d+}$. Antibodies to MUC1 VNTR peptides reacted with MUC1$^+$3T3 and MUC1$^+$P815 similarly to the human breast cancer cell lines T47D and MCF7 (typing with anti-HMFG: BC2 antibody, anti-fusion protein: VA1 and VA2 antibodies, and anti-MUC1 peptide antibodies: BCP7, BCP8, BCP9 and BCP10). However the murine tumour was differently glycosylated than the human tumour as MUC1$^+$3T3 and MUC1$^+$P815 cells were reactive with anti-carbohydrate (3E1.2) antibody (epitope: glycolylsialy-Tn) but not with other antibodies to carbohydrate (CC5-epitope: blood group Le$^2$. This shows that the protein antigens are intact, but the glycosylation is altered. This is not surprising as mice and humans have different glycosyl transferases and therefore different patterns of glycosylation. However, after removal of sugars by pagal treatment, the antibodies of MUC1 VNTR (non-APDTR; SEQ. ID NO: 7 reacting antibodies) which previously had weak or no reaction with cell lines, became reactive as their epitope has now exposed. There was no difference noted with the (AP)DTR(PA) reactive antibodies. There was a major difference in reactivity with the carbohydrate reactive antibody (3E1.2) where the staining became weak or negative after pagal treatment, indicating that the pagal was indeed removing O-linked sugars as the epitope of 3E1.2 is O-linked to the protein core of the mucin (18). The typing was repeated at different times and the same results were obtained, which indicated that the phenotype was stable (not shown).

In vivo growth of MUC1$^+$3T3 cells:

BALB/c mice received a subcutaneous injection of $5 \times 10^6$ MUC1$^+$3T3 or 3T3 cells and the subsequent growth measured; 3T3 cells grew progressively and were not rejected, as would be expected in BALB/c mice. By contrast the MUC1$^+$3T3 cells grew progressively until day 10 when they started to shrink and had gradually disappeared by day eighteen. Thus, the human MUC1$^+$ gene product appears to confer an immunogenicity on 3T3 cells, leading to their rejection. This was indeed the case as the subsequent challenge with 5×10⁶ MUC1⁺3T3 or 3T3 cells demonstrated the total resistance in immunized mice to the growth of MUC1⁺ 3T3 cells, whereas 3T3 cells grew—that is, the immunogenicity was found only in MUC1⁺ bearing tumours and was specific for this antigen. Specificity and memory indicate an immune response to MUC1⁺ and not some other effects such as MUC1⁺ effecting the growth properties of 3T3. After several weeks of repeated experiments using tumours passaged in vivo, we noted that not all of the mice rejected their tumours and up to 30% of MUC1⁺ tumours continued to grow. When these tumours were excised and MUC1⁺ measured serologically, a proportion of cells in the tumours were MUC1⁺, that is, some of the MUC1⁺ transfected cells had lost their capacity to express MUC1⁺ in vivo (we did not determine whether the genes were still present). Such observations have been reported elsewhere with rat tumours (19), presumably due to unstable expression of MUC1. In all our future studies we ensured that tumours were 100% MUC1⁺ when used, by serologically testing the MUC1 expression with the anti-HMFG antibody BC2.

T-cell immune responses to MUC1⁺3T3 cells:

Cellular immunity was most likely to be the mode of rejection as it is the commonest mode of rejecting tumour allografts in mice. This was confirmed by the ability of anti-CD3 antibodies to totally abrogate immunity. To determine whether CD4⁺ or CD8⁺ cells were responsible for rejection, mice received multiple doses of anti-CD4 or antiCD8 antibody as these were known to cause immunosuppression in other models (20, 21). Functional CD4 cell depletion by blocking had a transient effect on tumour growth, and tumours were rejected in a similar fashion to untreated mice. By contrast, anti-CD8 treatment led to prolonged tumour growth.

We conclude that CD3⁺ cells are totally responsible for rejection, CD4⁺ cells have a minimal effect and CD8⁺ cells are the major effectors of graft rejection. It was noted that in anti-CD8 treated mice, the tumours were smaller than those receiving anti-CD3—clearly the anti-CD8 antibody was not as effective as total T-cell removal with anti-CD3 antibody. CD4 cells having a minor effect was unlikely as the combined action of anti-CD4 and anti-CD8 was no better than anti-CD8 alone. However, we noted that anti-γ-interferon (γIFN) treatment (of no effect used alone) combined with anti-CD8 gave a similar effect with anti-CD3; thus γIFN plays a role in tumour graft rejection, which is mediated by CD8⁺ cells and γIFN.

Thus, MUC1⁺3T3 cells could immunize BALB/c mice against MUC1 carried on the 3T3 cells and gave rise to cellular immunity expressed by CD3⁺8⁺ cells but not by CD3⁺4⁺ cells; there was little humoral immunity as no anti-MUC1 antibodies were found. To measure the various parameters of the immune response, we examined (a) delayed type hypersensitivity and (b) cytotoxic T-lyrnphocytes.

(a) Delayed type hypersensitivity: Clearly the immune response was cellular and due to CD8⁺ cells. To determine whether this also involved a DTH response (usually considered to be mediated by CD4⁺ cells) or a cytotoxic T-cell response (usually CD8⁺), mice were immunized with MUC1⁺3T3 cells and a DTH was performed by injecting the hind footpads with various antigens. Preliminary studies demonstrated that in the absence of cyclophospbamide no measurable DTH responses occurred. A DTH response was detected in the footpads injected with killed (freeze/thawed 5 times) MUC1⁺3T3 cells and a weaker response when challenged with either HMFG, fusion protein-GST and Cp13–32-KLH. These responses were clearly specific as 3T3 cells elicited no response. To determine whether the DTH response was mediated by CD4⁺ or CD8⁺ cells, mice were injected with anti-CD4 and anti-CD8 antibodies and the DTH response measured. Anti-CD4 totally blocked DTH reactions, anti-CD8 partially blocked DTH reactions, but to a lesser extent, when challenged with MUC1 +3T3 cells, Cp13–32, HMFG and fusion protein. Thus the cells which cause the effective immune response to human MUC1 (CD8) were not the same as those eliciting a DTH response, although CD8⁺ cells certainly contributed to the DTH.

(b) Cytotoxic T-lymphocytes: Cytotoxic assays were performed after MUC1⁺3T3 cell immunization there was up to 60% lysis of MUC1⁺P815 targets treated with pagal. Untreated MUC1⁺P8 15 targets and non-transfected P815 targets were not lysed. Pagal treated and non-treated 3T3 and MUC1⁺3T3 targets also gave no lysis—possibly as 3T3 cells are poor targets for Tc assays. To determine the phenotype of the Tc, anti-CD4 and anti-CD8 antibodies were used in blocking studies—the anti-CD8 reagent (53-6.7) was known to be capable of blocking T-cell lysis by CD8⁺ cells. This proved to be the case in these studies as anti-CD8 could block Tc, whereas anti-CD4 and a control antibody had little effect. Since only Tc were found to pagal treated MUC1⁺P815 targets, and since non-A.PDTR reactive anti-MUC1 antibodies (VA1, BCP7, BCP9 and BCP10) became reactive with pagal treated MUC1⁺ 3T3, MUC1⁺P815, T47D and MCF7 cells, it is clear that both the antibody reactive and T-cell reactive epitopes are hidden, and both exposed after pagal treatment.

Mice resistant to MUC1⁺3T3 cells have CD8⁺ T-cell immunity, CD4⁺ DTH, a detectable Tc response due to CD8⁺ cells, and no antibody (see below). As the Tc response (at least at the level of the T-cell phenotype) correlated with the effector cell phenotype in rejecting tumours, it would appear to be the more appropriate response to measure.

Immune responses—B cells:

While it was shown above that cellular immunity was effective and little antibody was made, the role of antibody was not clear. Further, mice generally make poor antibodies and mobilize complement so poorly that they are not the species of choice on which to study antibody mediated destruction of grafts, unless certain conditions are met—a) the provision of sufficient antibody (be it polyclonal or monoclonal); b) the provision of sufficient complement; c) high density of surface antigens. The MUC1⁺ antigen density is high so additional antibody and complement were provided. In addition, the mice were in-immunosuppressed with CD3 to remove any component of cellular immunity (22). In spite of large amounts of antibody and complement (as described in materials and methods) (capable of rejecting skin allograft and xenografts), the tumours grew progressively—indeed, at the same rate as in mice not receiving antibody. Thus, antibody and complement are unable to cause rejection of MUC1⁺3T3 cells.

Immunization with HMFG, peptides and fusion protein:

The preceding defines a model of the murine immune response to human MUC1 transfected into 3T3 cells and forms the basis for using various immunogens to generate a similar or greater immune response with synthetic materials as that produced with cellular MUC1. The aim was clearly to substantially decrease tumour growth after immunization. As immunogens, natural mucin (HMPG), synthetic products—MUC1 peptides made of VNTR dimers, and a 5× VNTR repeat fusion protein were used. It should be noted that without prior immunization, tumours are rejected after eighteen days—such mice then being resistant to a subsequent challenge. Thus there is a "window" of approximately eighteen days when tumours will be rejected. So that, immunization could lead either to no tumours appearing or to reduced size during this time.

To examine the immunogenicity of HMPG fusion protein and synthetic peptides groups of 15 BALB/c mice were immunized with 50 μg of these materials and challenged with 1–5×10$^6$ 3T3 or MUC1$^+$3T3 cells. The 3T3 cells had the same progressive growth in all immunized and non-immunized mice, so there were no non-specific effects of the immunization procedures. When mice were challenged with the lower dose of 1×10$^6$ cells, significant differences were noted as compared to the non-immunized control. Thus, on day six, mice immunized with either the peptide or fusion protein had tumours approximately 25% that of controls; immunizing with HMFG was less effective, tumours being approximately 60% the size of controls. However when challenged with 5×10$^6$ MUC1$^+$3T3 cells, there was some difference in tumour size, compared to the controls, but not as obvious by challenging with a lower dose. As expected with subsequent tumour challenge, the peptide immunized mice which had rejected the tumour were now resistant to tumour challenge. Thus, immunizing mice with peptides, fusion proteins or HMPG and challenging with a low dose of MUC1$^+$3T3 cells gave rise to some anti-tumour effect. Although the VNTR containing peptide, fusion protein and HMPG gave some degree of protection, mice immunized with the N- and C-terminal peptides of MUC1 had no significant protection indicating that these peptides do not induce immunity to MUC1, and also showing that the immunization procedure itself was without effect. To measure the various parameters of the immune response, we examined (a) MUC1 antibody production. (b) delayed type hypersensitivity and (c) cytotoxic T-lymphocytes.

(a) Antibody: Immuized mice with peptides, fusion protein or HMPG had high levels of anti-MUC1 antibody both before and after tumour injection. Thus, immunization gave rise to high levels of antibody, but apparently little cellular immunity as shown by a minor effect on the tumours. It was of interest that mice immunized with the control peptide (T4N1), and which had rejected the tumour did not produce antibodies against MUC1; nor did the mice immunized with peptide and other immunogens have an increase in antibody titre after rejecting the tumour.

(b) DTH: Mice immunized with HMFG, Cp13–32 and fusion protein-GST had DTH responses to the various MUC1 antigens and which could be inhibited by CD4 (totally) and CD8 (partially) antibodies. Thus, immunization with the three agents gave rise to some degree of cellular immunity but not sufficient to greatly inhibit tumour growth.

(c) Cytotoxic T-lymphocyte assay: Tc assays were performed from spleen and lymph node cells of immunized mice and no cytotoxic cells were detected. Thus the various immunization procedures appeared to bias the immune response to antibody production, rather than cellular immunity.

Table 2 summarizes the differences in immunizing with cellular and synthetic antigens.

TABLE 2

Differences in immunizing with cellular and synthetic antigens

| Immunogens | Tumour rejection | Antibody | DTH | Tc |
|---|---|---|---|---|
| Tumour MUCI$^+$3T3 | +++ | + | +++ | +++ |
| Peptide | + | +++ | +++ | − |
| Fusion protein | + | +++ | +++ | − |
| HMFG (mucin) | + | +++ | +++ | − |

+++ = high; + = low; − = absent

EXAMPLE 3

Analysis of M-FP

The MUC1 PP was bound to mannan using periodate as described in the materials and methods. The amino groups of the PP reacts with aldehyde residues of the oxidized mannan to form the labile Schiff base (Scheme I). Free mannan and PP was not separated from conjugated mannan.

Elution profiles for $^{125}$I-FP and $^{125}$I-M-FP obtained by gel filtration chromatography demonstrated that the mannan-fusion protein eluted as two peaks (201 Kd and 73 Kd). The FP eluted as two peaks: 38 Kd and 20 Kd (this lower peak may be GST due to cleavage of FP). Autoradiography analysis of $^{125}$I-FP and $^{125}$I-M-FP showed that most of the FP his been conjugated to mannan.

The activity of FP after conjugation to mannan determined by an ELISA test showed that the FP had retained all its activity.

In vivo growth of MUC1$^+$3T3 cells

BALB/c mice which received a subcutaneous injection of 5×10$^6$ MUC1$^+$3T3 cells grew progressively until day ten when they started to shrink and disappeared by day eighteen, whereas 3T3 cells were not rejected as expected by BALB/c mice as set out in Example 2 (FIG. 1). Thus, the human MUC1$^+$ gene product confers an immunogenicity on 3T3 cells, leading to their rejection, and such mice were totally resistant to subsequent challenge. Cellular immunity was the mode of rejection as anti-CD3 and anti-CD-8 antibodies totally abrogated immunity.

Immunization with Mannan-Fusion Protein

Figure 2B:
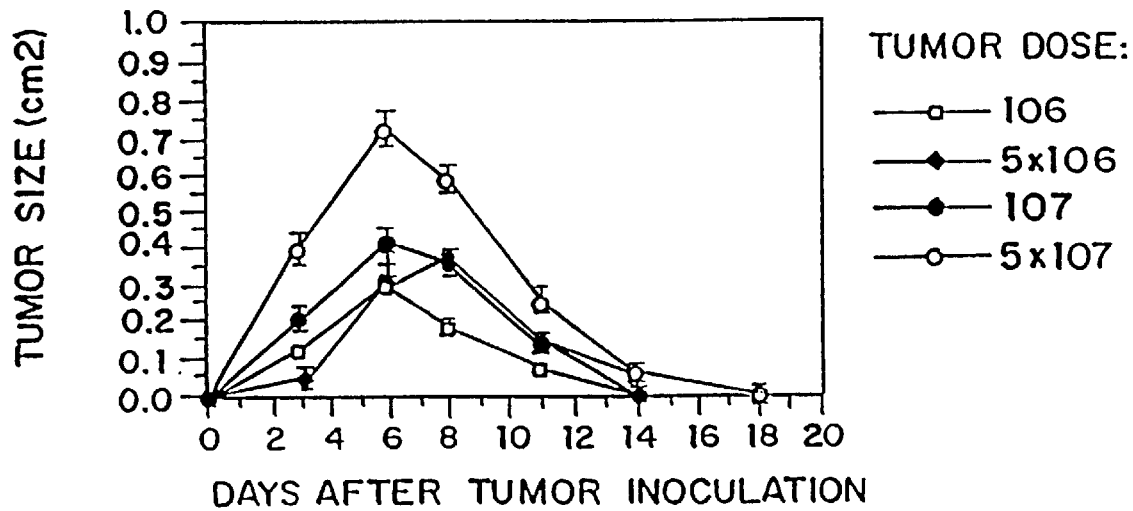
Figure 3A:
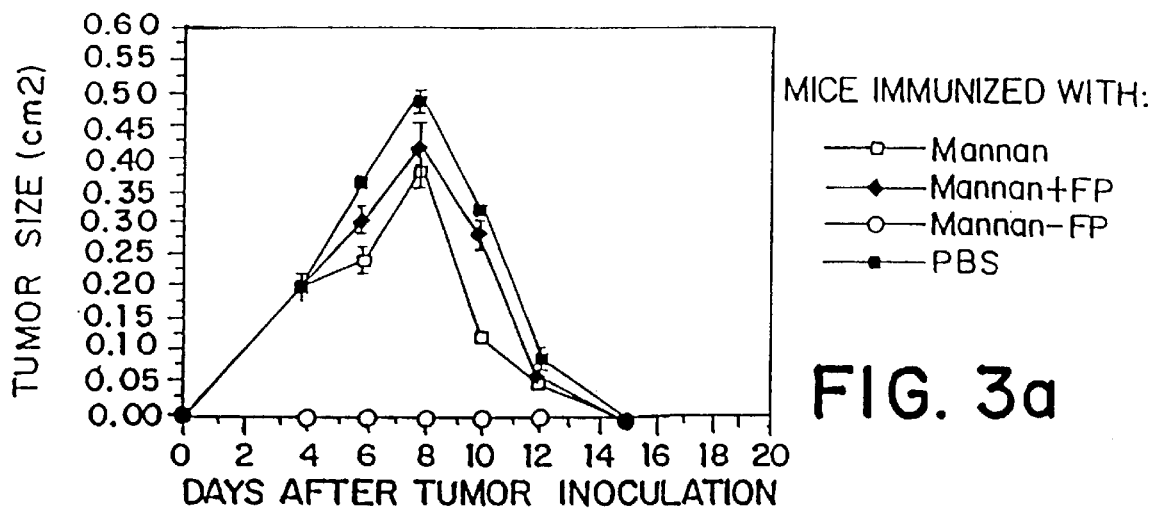
Figure 3B:
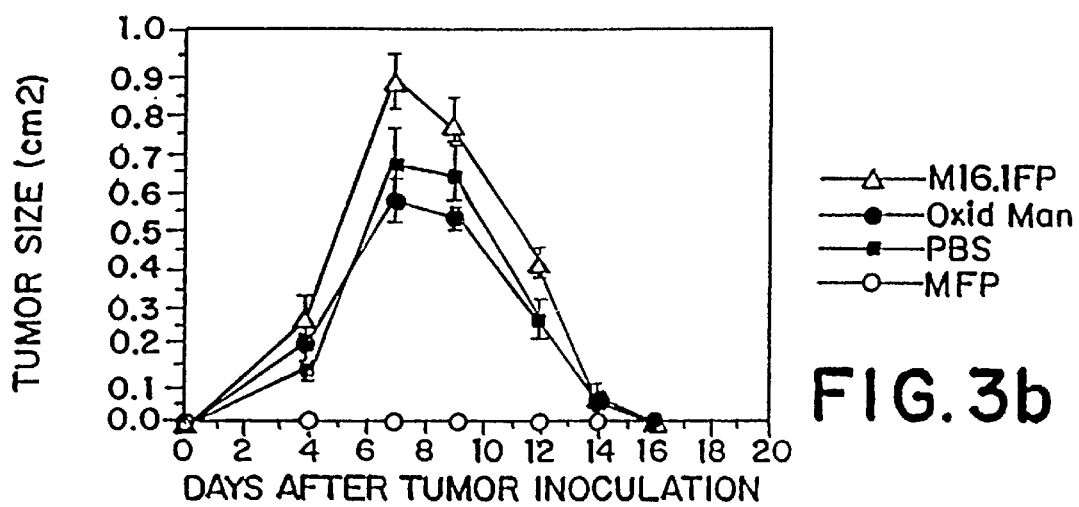
Figure 3C:
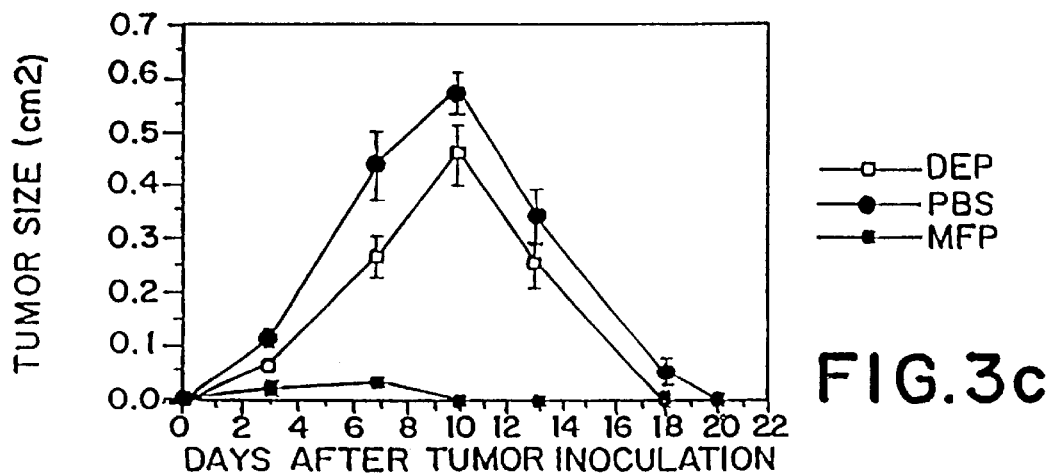

To examine the immunogenicity of the mannan-FP, groups of ten BALB/c mice were immunized with 5 μg mannan-FP (5 μg corresponding to the amount of FP) and challenged with 10$^6$–5×10$^7$ MUC1$^+$3T3 cells. There was no obvious tumour growth in immunized mice (FIG. 2A) as compared to non immunized mice (FIG. 2B). To show that the mannan-FP conjugate gave rise to specific anti-tumour immunity and that mannan or PP alone were without effect, mice were immunized with an equivalent dose of mannan (as in the conjugate=7 mg/ml), a mixture of mannan and FP and a group of non immunized mice and were challenged with 10$^6$ MUC1$^+$3T3 cells. Mice immunized with mannan-FP conjugate, no tumour growth was observed whereas mice immunized with mannan alone and a mixture of mannan and FP, tumours grew no different as compared to non immunized mice (FIGS. 3A, 3B and 3C). Thus, protection of tumour growth was specific for the conjugate and mannan and FP alone was without effect. Mannan-FP immunized mice were challenged with 10$^6$3T3 cells and the 3T3 cells had the same progressive growth in immunized and non-immunized mice (FIG. 4), indicating that there were no non-specific effects of the immunization procedures.

Immune response to M-FP

Anti-CD3 antibody could totally abrogate immunity in mice immunized with M-FP (FIG. 5) and mice which received anti-CD4 or anti-CD8 antibodies showed the following effect: CD4 immunosuppression had a minor effect on tumour growth (FIG. 5); by contrast anti-CD8 treatment led to prolonged tumour growth. Thus CD3$^+$/CD8$^+$ cells are totally responsible for the immunity and tumour protection, CD4$^+$ cells had a minimal effect (FIG. 5). Thus M-FP could immunize against MUC1 carried on the 3T3 cells giving rise to cellular immunity expressed by CD3$^+$/CD8$^+$ cells but not by CD3$^+$/CD4$^+$ cells. To measure the various parameters of the immune response, we examined (a) delayed type hypersensitivity, (b) cytotoxic T-lymphocytes (c) T-cell proliferation and (d) antibody production.

(a) Delayed type hypersensitivity: DTH responses (usually considered to be mediated by CD4$^+$ cells) were performed by injecting the hind footpads with the various antigens (FIG. 6). A DTH response was detected in the footpads challenged with killed (freeze/thawed five times) MUC1$^+$3T3 cells, HMFG, FP-GST, Cp13–32-KLH, mannan-FP and a weaker response to GST (as GST is part of the FP) (FIG. 6). These responses were clearly specific as killed 3T3 cells, mannan alone, an irrelevant peptide (T4N1) and PBS could elicit no responses. To determine whether the DTH response was mediated by CD4$^+$ or CD8$^+$ cells, mice were injected with anti-CD4 and anti-CD8 antibodies and the DTH response measured. Anti-CD4 totally inhibited DTH reactions, anti-CD8 inhibited but to a lesser extent (FIG. 6). Thus the cells which caused the effective immune response to human MUC1 (CD8$^+$ cells as shown in FIG. 5) were not the same as those eliciting a DTH response, although CD8$^+$ cells certainly contributed to the DTH.

(b) Cytotoxic T-lymphocytes: Cytotoxic assays were performed and it was shown that after M-FP immunization there was 30% MUC1 specific lysis of MUC1$^+$P815 targets treated with pagal (FIG. 7). Untreated MUC1$^+$P815 targets gave 15% MUC1 specific lysis whereas non-transfected P815 targets were not lysed (FIG. 7). It is likely that these cells were CD8$^+$(12).

(c) T cell proliferation: Proliferation assays were performed and it was shown that after M-FP immunization there were proliferative T-cells to M-FP, FP, Cp13–32, HMFG, and to pagal treated and untreated MUC1$^+$3T3, MUC1$^+$P815 cells. Other stimulants bad no effect.

(d) Antibodies to Mannan GYST-MUC1 fusion protein conjugate: Mice were bled and their sera tested by ELISA for anti-FP antibodies. No anti-FP antibodies were detected compared to mice immunized with FP alone. Plates coated with mannan coupled to BSA were used to detect anti-mannan antibodies and no anti-mannan antibodies were detected. Normal mouse serum was as a negative control.

Thus, mice made totally resistant to MUC1$^+$3T3 cells by immunizing with FP coupled to mannan have CD8$^+$ T-cell immunity, CD4$^+$/CD8$^±$ DTH, a detectable Tc response due to CD8$^+$ cells, proliferative T-cells to the specific to the immunizing antigen, and little humoral immunity as no anti-MUC1 antibodies were found M-FP appears to be able to induce an anti-tumour response, similar to that shown with tumour cell rejection (12).

M-FP in therapy

Figure 8A:
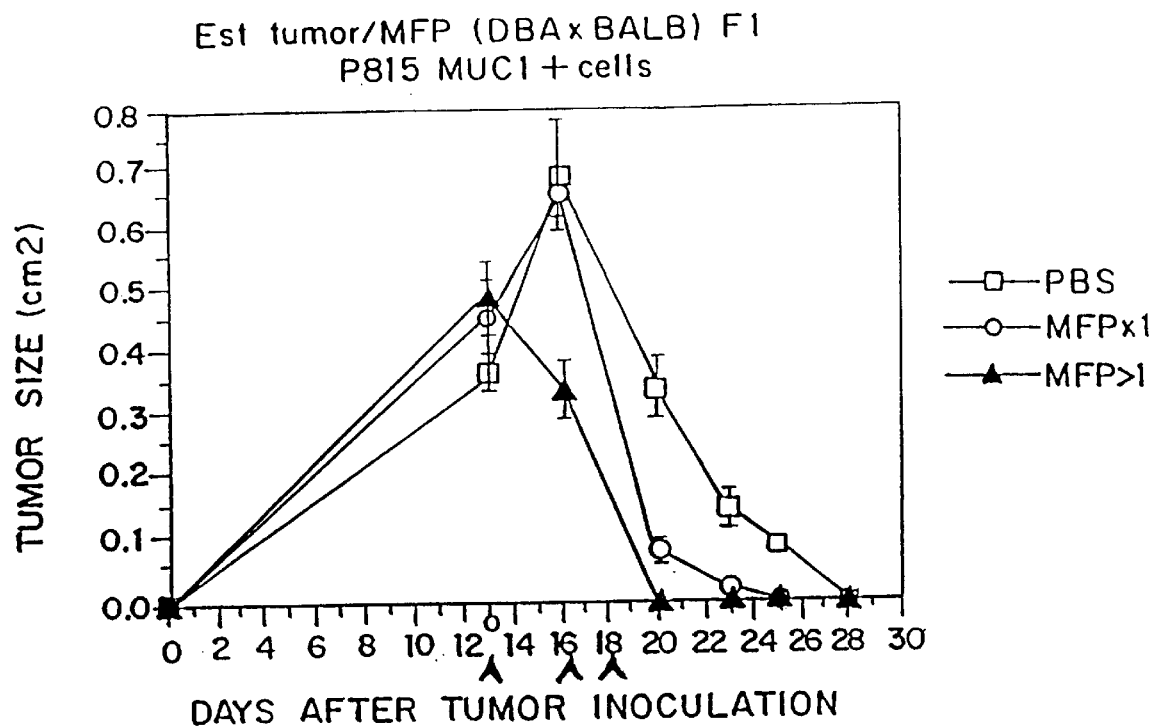
Figure 8B:
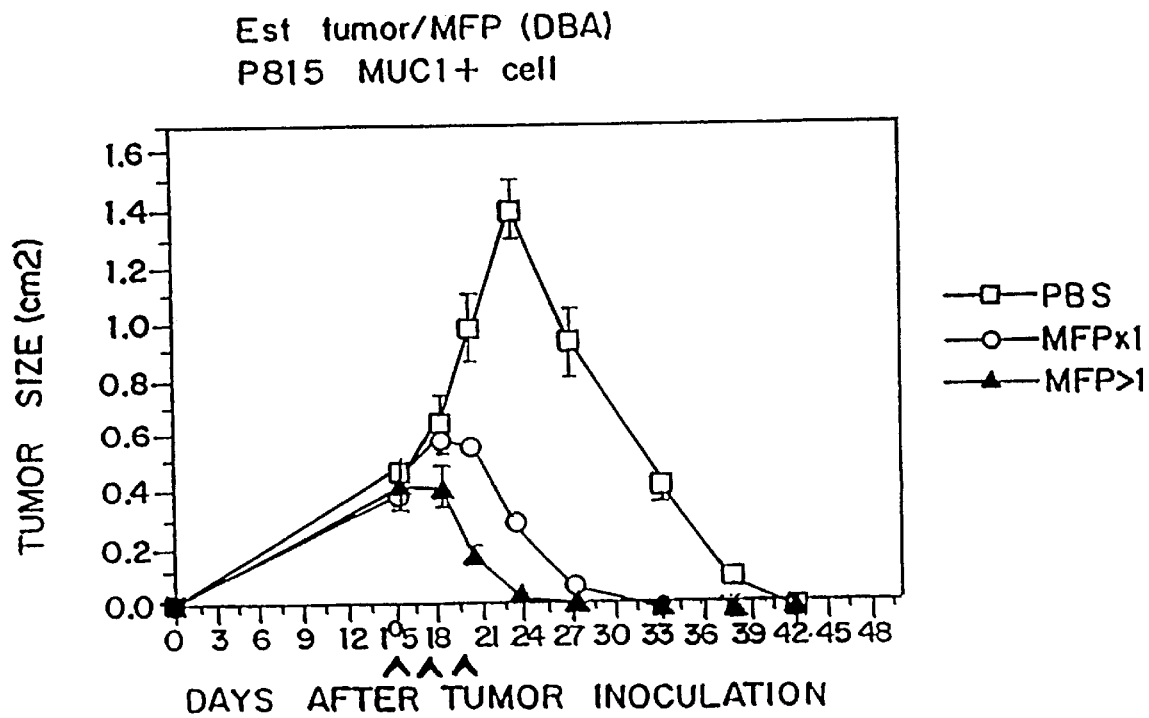

To determine the effectiveness of M-FP as a therapeutic agent against established tumours, injections of MFP were delayed until tumours were established. MUC1$^+$P815 cells grow progressively in (DBA/2×BALB/c)F1 mice, when given subcutaneously, until day sixteen to twenty when they start to shrink and usually disappear by day twenty-eight (FIG. 8A). To examine the effectiveness of M-FP on established tumours, groups of five (DBA/2×BALB/c)F1 mice were injected with 5×10$^6$ MUC1$^+$P815 cells; thirteen days later, the mice were injected with 5 $\mu$g M-FP (5 $\mu$g corresponding to the amount of FP) once, or every other day. Tumours in control mice (injected with PBS) were rejected by day twenty-eight. However, mice injected regularly began to reject their tumours immediately, the tumours rapidly disappearing by day twenty. A single injection also gave rise to more rapid rejection (FIG. 8A).

Another model was examined using MUC1$^+$P815 cells in DBA/2 mice, which grow until day twenty-two to thirty when they shrink and usually disappear by day forty two. MUC1$^+$P815 cells were injected subcutaneously and on day fifteen DBA/2 mice were injected with MFP. In the control group mice injected with PBS, tumours were rejected by day forty-two whereas mice immunized with MFP once on day fifteen tumours were rejected by day thirty-three (FIG. 8B) compared with mice immunized every other day, tumours were rejected by day twenty-seven with a rapid reversal in their growth after a single injection. Thus, not only do pre-immunized mice have an anti-tumour effect, this can be obtained with established tumours.

EXAMPLE 4

A patient suffering from breast cancer was injected with 50 $\mu$g of the mannan fusion protein produced according to Example 1. No side-effects were seen following immunization. The therapeutic treatment of the patient's cancer is currently under evaluation and it has already been observed that several lesions in the bone have disappeared.

EXAMPLE 5

The VNTR's of mucins MUC1 through MUC6 are coupled to mannan and other carbohydrates according to standard procedures such as described in Example 1. Table 3 sets out a description of the various mucin core proteins.

TABLE 3

Description of human mucin core proteins, cDNA's and genes

|  | MUC1 | MUC2 | MUC3 | MUC4 | MUC5 | MUC6 |
| --- | --- | --- | --- | --- | --- | --- |
| Tissue | Breast, ovary, pancreas $^a$GI, $^b$GU and $^c$resp. tract | GI and resp. | GI tract | Resp. tract | Trachea Bronchus ± Stomach | Stomach gall bladder |
| Polymorphism | Yes | Yes | Yes | ? | ? | ? |
| Chromosome | 1q21 | 11p5.5 | 7q | 3 | 11p15 | 11015.4/5 |
| Molecular weight of protein kDa | 120–240 | 160 | 190–320 | ? | ? | ? |

TABLE 3-continued

Description of human mucin core proteins, cDNA's and genes

|  | MUC1 | MUC2 | MUC3 | MUC4 | MUC5 | MUC6 |
|---|---|---|---|---|---|---|
| Base pairs | 60 | 60 | 51 | 48 | 24 | 507 |
| VNTR*([d]aa/repeat | 20 | 23 | 17 | 16 | 8 | 169 |

[a]GI—Gastrointestinal;
[b]GU—Gastrourinary;
[c]Resp.—Respiratory;
[d]aa—amino acids
*MUC1 VNTR - SAPDTRPAPGSTAPPAHVT SEQ ID NO: 22
MUC2 VNTR - PTTTPISTTTMVTPTPTPTGTQT SEQ ID NO: 2
MUC3 VNTR - HSTPSFTSSITTTETTS SEQ ID NO: 3
MUC4 VNTR - TSSASTGHATPLPVTD SEQ ID NO: 4
MUC5 VNTR - PTTSTTSA (494 base pair insert - eight amino acid tandem repeat) SEQ ID NO: 5
MUC6 VNTR - 169aa repeat unit
MUC7 VNTR - TTAAPPTPPATTPAPPSSSPPE SEQ ID NO: 7

EXAMPLE 6

MHC Restriction of CTL's After MFP Immunization

To determine whether the CTL's produced in mice were MHC or indeed, Class I MHC restricted, mice were immunized with MFP (5 μg weekly×3) and their spleen cells removed and used as CTL's against various $^{51}$Cr labelled target cells. The results demonstrate that:

a) Immunizing H-$2^d$ mice (DBA/2, NZB, BALB/c or B10.D2) gave CTL's against P815-Tm211 (MUC1$^+$) P815 cells but not against P815-MUC1 cells.

b) When mice of other H-2 haplotypes were immunized, no CTL's were found on testing the H-$2^d$ P815 MUC1$^+$ cells (in particular H-$2^b$; C57BL/6; 129 and BALB.B; H-$2^k$: CBA; H-$2^s$: SJL and H-$2^w$: NZW. Of interest in these studies is the finding that:

BALB/c (H-$2^d$) was +  
BALB.B (H-$2^b$) was −  } these are a congenic pair differing only in H-2

B10.D2 (H-$2^d$) was +  
C57BL6 (H-$2^b$) was −  } these are a congenic pair differing only in H-2

This maps the reactivity to the H-2 MHC complex.

c) In other studies it was shown that mice of the H-$2^b$ haplotype had activity for H-$2^b$ (E3 MUC1$^+$ tumour cells), but not for other H-2 haplotypes.

Thus, CTL responses in mice to MFP are H-2 (MHC) restricted.

EXAMPLE 7

T-cell Proliferation to MFP in Mice

Mice were immunized with various MFP (5 μg/week×3) and tested on a range of peptides at different doses in a proliferation assay. In this assay, different peptides are added in different amounts to splenic cells in tissue culture and after forty-eight hours $^3$H-thymidine is added for twenty-four hours. The cells are harvested and the incorporated radioactivity measured. The studies show that:

i) MFP stimulates the proliferation of T-cells from immunized mice in the presence of peptides.

ii) There is a dose response so that peptides
C-p13–32, C-p1–24: 5 mcM is the optimal dose
p13–32, p1-$^{24}$: 10 mcM is the optimal dose
Ap1–15<1.0 mcM is the optimal dose
P5–20<1.0 mcM is the optimal dose The sequence numbering is such that:

```
1         5          10         15      2021 next
                                             repeat
P D T R P A P G S T A P P A H G V T S A P - - -
SEQ ID NO; 23
``` iii) Of the peptides used:

| p5–20 is | + |
| p14–24 | } are − |
| p16–24 | |

The epitope is not likely to be the antibody epitope APDTR, but is in p14–24~possibly GSTAP.

EXAMPLE 8

Phase I Study of Synthetic MUC1 Peptides in Cancer

The aim of this example is firstly to determine whether synthetic or other MUC1 agents are immunogenic in humans and secondly, to determine whether an immune response against a self-peptide has any deleterious effects by reaction on normal tissues containing MUC1—the basis of a Phase I study. Anti-tumour effects are then to be examined.

Materials and Methods

Patients

To be eligible to enter the trial, patients had to have histologically proven breast cancer and only those with metastatic disease were considered, particularly those not having received cytotoxic chemotherapy in the preceding four weeks. The patient bad to have given written informed consent and those who were lactating or pregnant were ineligible for the study. All patients had their clinical status documented and base-line blood samples taken for MSA and CASA analyses The studies undertaken were routine for a Phase I study including history and examination, full blood examination, toxicity notation, collection of blood for creatinine and amylase. Specific testing for immune response to the injected material was done in several ways:

Serological and Cellular Studies
  a) the MSA and CASA tests were performed—these detect circulating MUC1 and conceivably alter with an immune response to the antigen (MSA detects a unique carbohydrate antigen; CASA the APDTR peptide SEQ ID NO: 7).
  b) samples were tested for anti-MUC1 antibodies using an ELLSA test and testing and separately on diphtheria toxoid, fusion protein, GST, p13–32 synthetic peptide, HMFG and on another peptide (STPA—derived from the sequence of CD46—used as a non-specific negative control).
  c) T-cell responses were determined in three ways:
    i) delayed type hypersensitivity reactions—(DTH) performed using standard antigens to determine the patients response to diphtheria or tetanus; response to the injected material (DT-peptide); and separately testing peptide linked to another carrier e.g. human serum albumin.
    ii) T-cell proliferation—performed by taking blood from the patient, separating the peripheral blood lymphocytes (PBL) and establishing these in tissue culture with appropriate antigens (see below) and after forty-eight to seventy-two hours adding tritiated thymidine or twenty-four hours and measuring proliferation.
    iii) T-cell cytotoxicity—patients proliferal blood cells were isolated and set up in short term (four hour culture) with $^{51}$Cr labelled target cells consisting of murine cells (MUC1$^+$3T3 and P815) and human tumour cells which express human MUC1 (T47D, BT20).

Finally, the responses of the tumours were monitored in the patients.

Synthesis and Conjugation of Peptides

Peptide C-pI 3–32 (CPAHGVTSAPDTRPAPGSTAP SEQ ID NO: 19) derived from the sequence of MUC1 variable number of tandem repeats (VNTR) were synthesized using an ABI peptide synthesizer (Foster City, Calif., United States of America). Peptide STP-A representing the serine, threonine and proline rich region of human CD46 was used as a negative control. The peptide C-p13–32 was conjugated to diphtheria toxoid (DT) (Special sample, CSL, Melbourne, Australia) using glutaraldehyde. Ten milligrams of peptide C-p 13–32 was reacted with 1250Lf DT in the presence of 5 ml, 0.25% glutaraldehyde at room temperature for six hours, dialysed against phosphate-buffered saline. The conjugate DT-C-p1 332 was filtered (0.22 mm, Millipore) in a laminar flow hood. The activity of DT-Cp1 3–32 was tested by an anti-MUC1 antibody BC2.

The sterility and pyrogen tests were performed at the Pharmacology Department, Melbourne University, and Microbiology Department, Austin Hospital, Australia).

Enzyme-linked Immunosorbent Assay (ELISA

To test human antibody to C-p13–32, various antigens including FP, DT and HMFG were coated onto PVC plates (Costar) in 0.05M carbonate buffer, pH9.6 for two hours at 37° C., and non-specific binding sites were blocked with 2% BSA for one hour at 37° C. After washing with PBS-0.05% between twenty, serum samples at series dilution were added to each well, and incubated at 4° C. overnight. After thorough washing of the plates, sheep anti-human immunoglobulin labelled with horseradish peroxidase (Silenus, Melbourne, Australia) was added to plates and incubated for two hours at ambient temperature. The plates were washed and at the bound human antibodies were detected by the addition of 0.03% 2,2-azinodi (3-ethylbenzthiazoline sulfate) in 0.1M citrate buffer, pH4, containing 0.02% H202. The absorbency was measured at 405 nm using an ELISA reader (Bioteck, EL312e). The antigen used in this assay were a) human milk fat globule (HMFG), b) fusion protein, containing five VNTR repeats of MUC1 and glutathione-s-transferase, produced using P-GEX vector; c) DT, d(C-p13–32, and e) negative control peptide STP-A.

To measure circulating MUC1 antigen in serum two commercial kits (MSA assay and CASA assay) (Medical Innovations Limited, Artarmon, NSW, Australia) were used.

The MSA assay is an inhibition assay using an anti-MUC1 antibody, the binding of which to the MUC1 can be inhibited by the circulated MUC1 in the sera of patients.

The CASA assay is a sandwich ELISA, which used two anti-MUC1 antibodies.

Results

Toxicity: In general, there was little systemic toxicity—particularly with the first injections. Later, local reactions occurred in patients which we presumed to be due to a local DTH reaction to diphtheria toxoid as there was erythema and induration which lasted up to seventy-two hours. In some patients, this was accompanied by enlargement of local lymph nodes. Apart from these reactions after the injection, no other side effects were noted.

Figure 9A:
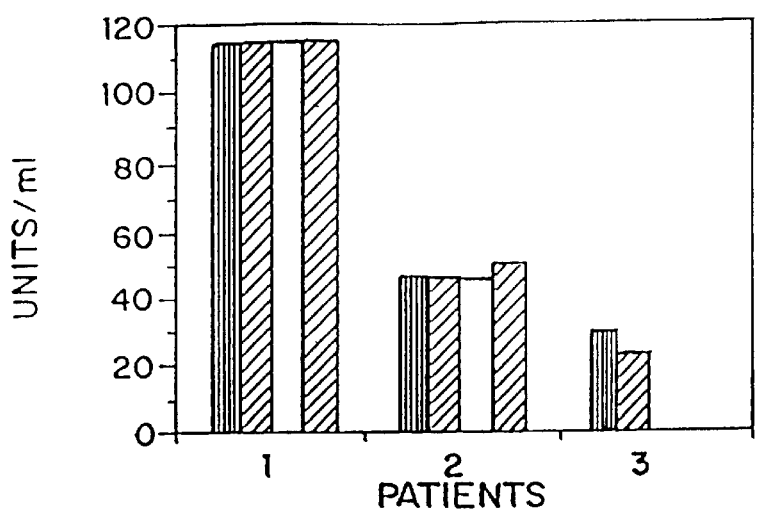
Figure 9B:
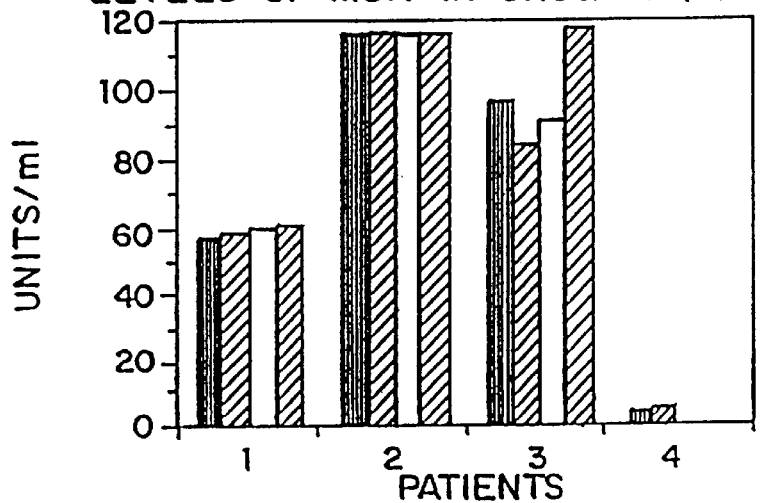
Figure 9C:
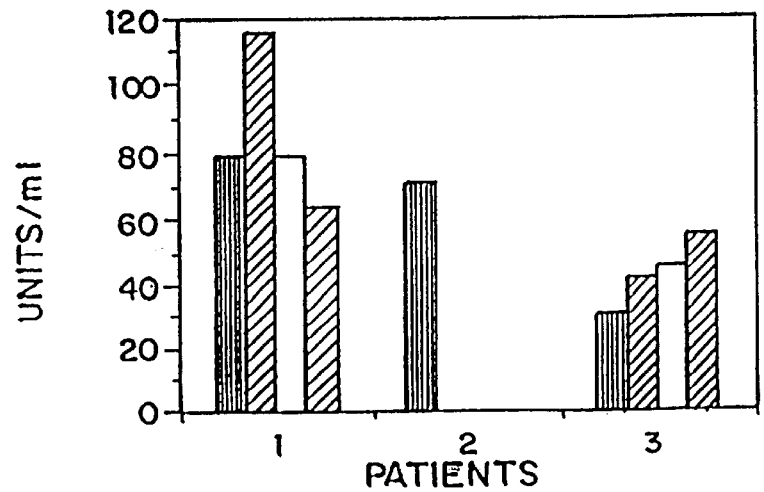
Figure 11A:
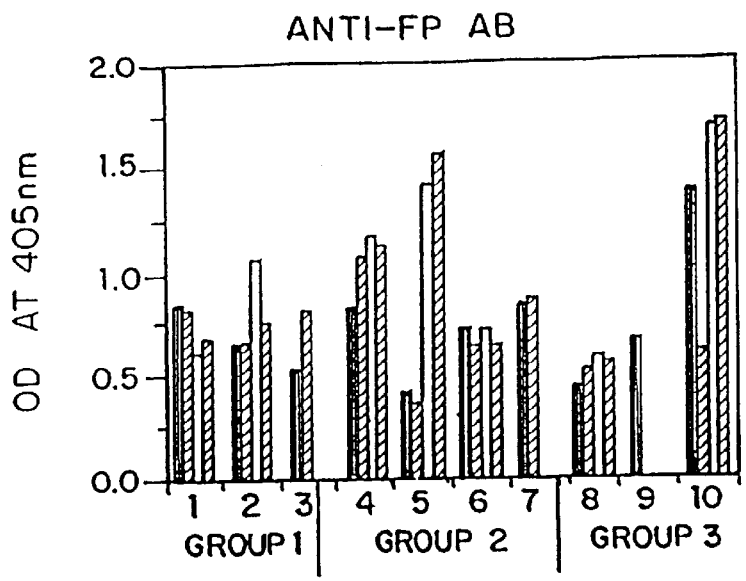
Figure 11B:
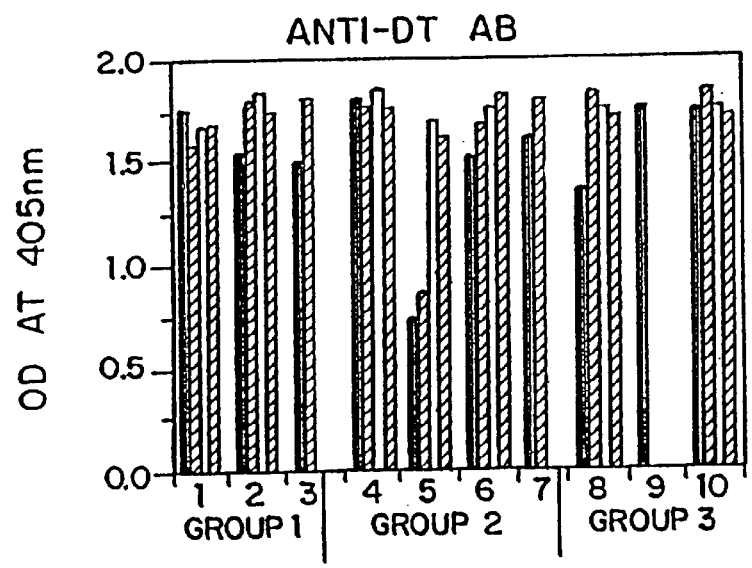
Figure 11C:
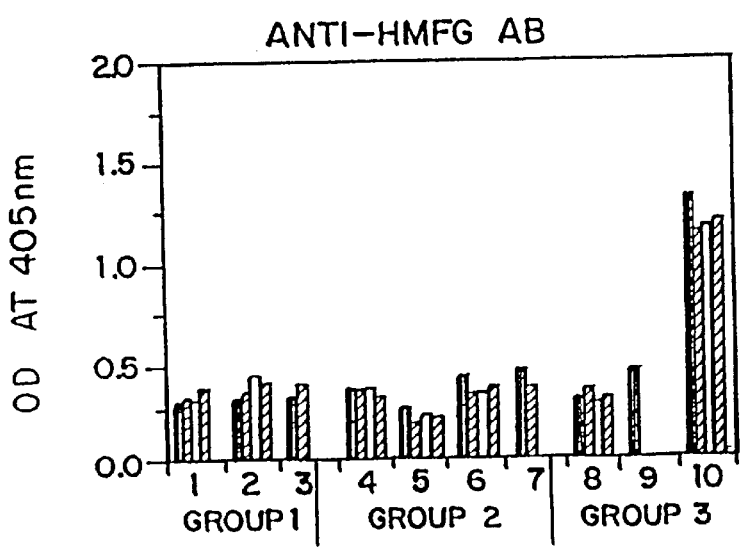
Figure 11D:
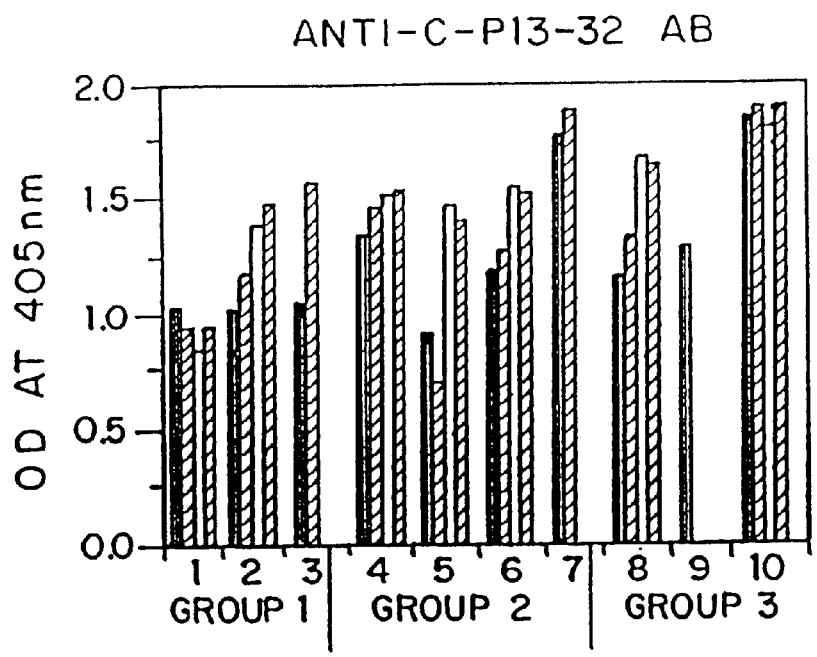
Figure 11E:
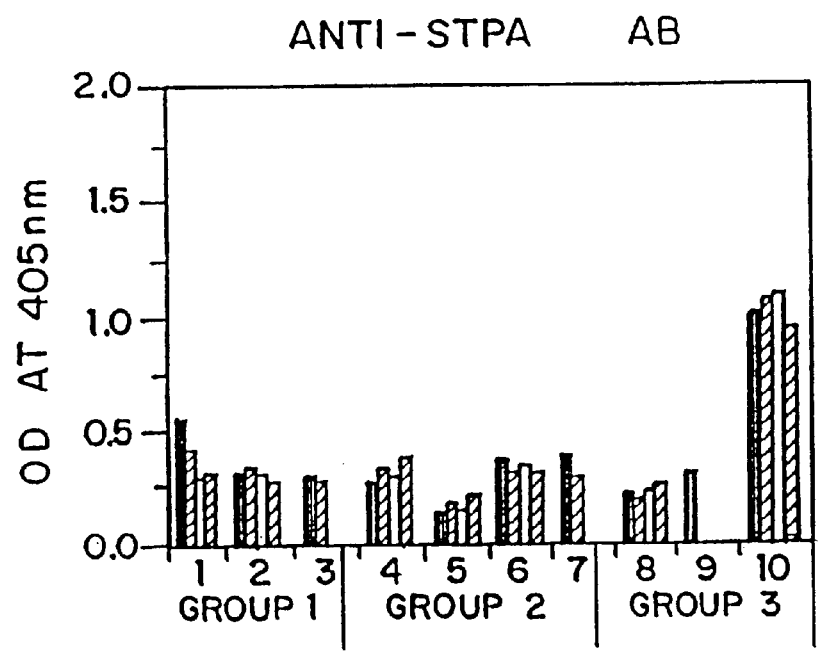

MSA and CASA testing: These tests were performed on most patients and no trends were noted. The data is presented on samples taken at different times during the course of injection and in most patients, there was virtually no increase in the MSA level over the course of the injection (FIGS. 9A, 9B and 9C). Similar comments can be made with the CASA tests (FIGS. 10A, 10B and 10C). In most patients, there was little change in the levels, although in two patients a progressive increase was noted and this correlated with the progressive disease in those patients. It would be appropriate to state there were essentially no changes in the circulating levels of MUC1 detected by these two separate tests over the course of injection and some weeks thereafter.

Anti-MUC1 antibody (FIG. 11): Firstly, we would indicate some difficulty in using human serum samples on synthetic peptides—in most cases there is significant background on the synthetic MUC1 peptides not seen with HMFG or with the STPA non-specific peptide. Thus, the fusion protein and C-p13–32 are non-specifically "sticky". With the exception of several patients, there appeared to be little increase in antibody formation over the course of the injection and we conclude that immunization with peptide gave rise to no antibodies in 10/12 patients. However, in two patients (number 5 and number 10) significant increases in antibodies reacting with fusion protein and anti-C-p13–32 antibodies were noted—and these were specific increases as there was no alteration in the effect on either HMFG or the STPA. In patient number 5, an increase in the diphtheria antibody titre had also occurred, but not in patient number 10. Thus, antibody responses were noted, but not uniformly so.

Skin Testing: Skin testing of patients is still in progress. At the lower doses of 0.15 mg and 0.25 mg was not done and is currently in progress with 0.5 mg and 1 mg doses. At this stage there are no responses to the synthetic peptide, although responses were noted to diphtheria. As indicated, these studies are in progress.

T-cell proliferation: The validity of these assays was shown by the proliferative response found in six of ten normal subjects when tested with diphtheria toxoid—these responses indicating the previous immunization with the toxoid. Also of note was that none of the ten normal subjects had any proliferative responses to the different antigens used, in particular those containing MUC1 (fusion protein, synthetic peptide, C-p13–32, HMFG) or to the murine cell line expressing MUC1 (MorS). In addition, five of nine separate tests on the patients with cancer showed proliferative responses to DT, although these tests were only performed on six patients. It was of interest that after several courses of injections, four of the six patients showed proliferative responses to MUC1 in one form or another—this was particularly noted on the murine cell line expressing MUC1 on the cell surface, but in two patients, one to C-p13–32 DT and this patient also responded to the fusion protein. None of the patients responded to MUC1 in HMFG nor to the non-specific peptide T4N1. Thus, some proliferative responses were noted in some patients, but not in all.

Tumour Response: In the seven patients with progressive disease, in three the disease was stable.

EXAMPLE 9

1. Introduction

Immunotherapeutic approaches for the treatment of breast cancer have included the use of monoclonal antibodies and the generation of cytotoxic T lymphocytes (CTL) [29–34]. The identification of target antigens, the availability of recombinant proteins and cytokines have given impetus to immunotherapy. Thus, there are new means by which to generate an effective cytotoxic T cell response to MUC1-expressing carcinomas of the breast and other tissues [35]. MUC1 is a particularly attractive target for the generation of CTL: it is immunogenic in mice for the production of antibodies and for CD8$^+$ CTL, and further the MHC Class I H-2 and HLA-A*0201 binding peptides have been mapped in the VNTR [36–39]. Furthermore, in cancer cells, there is up to a 100 fold increase in the amount of mucin [40] and there should be a significant amount of MUC1 peptide available to be bound by Class I molecules. The reason for the focus on the VNTR peptides is clear–it is the most immunogenic region in MUC1 when whole tumour cells or mucin extracts (HMFG) are used to immunise mice for the production of antibodies [40]. Because of this focus and the finding that non-HLA restricted CTL also are directed to the VNTR, almost all interest in MUC1 for CTL induction has concentrated on VNTR peptides [37,41, 42]. In contrast in the following examples the inventors describe the induction of CTL to non-VNTR epitopes, in the extracellular and intracellular parts of MUC1 identified by immunising mice with native mucin (HMFG) obtained from human breast milk, or by immunising with non-VNTR peptides as described herein.

2. Materials and Methods

2.1 Mice and Tumour Cells

BALB/c (H-2$^d$), C57BL/6 (H-2$^b$), human MUC1 transgenic mice (obtained from B. Acres (Transgene, Strasbourg, France)), transgenic HLA-A*0201/K$^b$ mice (H-2$^b$)(obtained from The Scripps Clinic and Research Foundation, La Jolla, Calif.) and double transgenic mice (A2K$^b$MUC1) were bred at The Austin Research Institute. The human MUC1 in the MUC1 transgenic mice (back crossed to DBA/2) is under the control of the human MUC1 promoter; MUC1 is expressed in the lung bronchioles, β-islets of the pancreas, kidney tubules and stomach [43]. The HLA-A*0201/K$^b$ mice express a transgene composed of the α1 and α2 domains of HLA-A*0201 and the α3 contains the transmembrane and cytoplasmic domains of H-2K$^b$ [44]. The double transgenic mice were screened for expression of the HLA-A*0201/K$^b$ and human MUC1 transgenes by flow cytometry with antibodies to HLA-A*0201 and MUC1. RMA-MUC1 is a MUC1 transfected (C57BL/6 (H-2$^b$)) lymphoma cell line [45]. Tm211 is a MUC1 transfected P815 mastocytoma (DBA/2 origin; H-2$^d$) obtained from B. Acres (Transgene, Strasbourg, France) [46]. All mouse cell lines were maintained in Dulbecco's modified Eagles medium (DMEM) with 100 IU/ml penicillin, 100 μg/ml Streptomycin and 10% foetal calf serum (all from Commonwealth Serum Laboratories (CSL), Melbourne) and human cell lines in RPMI with the same additives in a 7% humidified $CO_2$ incubator at 37° C. BALB/c, C57BL/6 and double transgenic A2K$^b$MUC1 mice were immunised intraperitoneally with 3 injections of 5 μg mannan-HMFG or HMFG on days 0, 10, 17 while HLA-A*0201/K$^b$ mice were injected once.

2.2 Synthetic Peptides

Peptides (Table 4) were synthesised at the ARI; the purity of the peptides (>95%) was determined by mass spectroscopy.

2.3 Conjugation of HMFG to Mannan

HMFG was isolated from human milk [49] and coupled to mannan. Mannan (1 ml, 14 mg/ml) in phosphate buffer (0.1M, pH6.0) was treated with sodium periodate (100 μl, 0.1M) and incubated at 4° C. for 30 min [48]. Ethanediol (10 μl) was added for 30 mins at 4° to stop the reaction, and the mixture was passed through a PD10 column (Pharmacia Biotech, Sweden), equilibrated in bicarbonate buffer (0.2 M, pH 9.0) and the oxidised mannan fraction was mixed with 1 mg of HMFG overnight at room temperature to give mannan-HMFG.

2.4 T Cell Epitope Prediction

There are several CTL epitope prediction algorithms available and in this study we used the program developed by Dr Kenneth Parker available on the internet (bimas.dcrt.nih.gov/molbio/hla_bind/) to identify potential T cell epitopes. This program is based on scores given to the amino acids at each of the positions from 1–9 from input sequences by comparison with the reported databases [49, 50]. Higher numerical values for the 9-mer predict increased likelihood of being a T cell epitope. For example, the T cell epitope for ovalbumin (Kb, SIINFEKL SEQ ID NO: 24) and papillomavirus-16 E7 protein (Db, RAHYNIVTF SEQ ID NO: 25) gives scores of 17 and 6 respectively.

2.5 Cytotoxic T Cell and Cytotoxic T Cell Precursor (CTLp) Frequency Assays CTL assays were performed as described [37, 39, 48]. Briefly, 7 to 10 days after the final immunisation, splenocytes were harvested, washed and resuspended in growth medium and serially diluted in 96-well microtitre plates. A standard 3 hr $^{51}$Cr release assay was performed with 1×10$^4$ peptide pulsed or untreated P815 or RMA cells as targets at various effector target ratios. Peptide pulsed P815 or RMA target cells were prepared by overnight incubation with 9-mer peptides (25 μg/ml) [37]. For CTL assays with A2K$^b$MUC1 double transgenic effectors, MCF7 (MUC1$^+$ HLA-A*0201$^+$) and BT20 (MUC1$^+$HLA-A*0201$^-$) breast cancer cell lines or the ME272 (MUC1$^-$HLA-A*0201$^+$) melanoma cell line was used as targets. All of these human tumour cell lines are susceptible to cell mediated lysis [39, 51, 52]. CTLp frequencies were determined from a minimum of 32 replicates, for at least 6 effector cell numbers (1×10$^3$–1.28×10$^5$). Cells were cultured in U-bottomed microtitre trays, with 5×10$^5$ mitomycin C treated BALB/c (H-2$^d$), C57BL/6 (H-2$^b$) or HLA-A*0201/K$^b$ spleen cells, in DMEM supplemented with 10% foetal calf serum, 5 μM of various MUC1 peptides (Table 1) or HMFG and 10 U/ml rhIL-2. Seven days later, each microculture was assayed for cytotoxicity by replacing 100 μl of culture medium with 100 μl target cell suspension containing 10$^{4}$ $^{51}$Cr-labelled Tm211 (H-2$^d$), RMA-MUC1 (H-2$^b$) Tumour or EBV transformed human B cells (HLA-A*0201) or MCF7 as targets. As a specificity control non-MUC1 expressing P815(H-2$^d$) or RMA(H-2$^b$) cells were used. Cytotoxic activity was considered to be present if in each well $^{51}$Cr release was found 3 standard deviations above the mean isotope release from 10$^4$ effectors cultured with stimulators only or from stimulator cells with peptide only or rIL2 only. A linear relationship (0.987≦r$^2$≦1) existed between the number of responder cells, represented on a linear scale, and the frequency of negative wells on a logarithmic scale. CTLp frequencies were determined as the inverse of responder cell dose required to generate 37% negative wells [53–55]. CTLp frequency assays were performed three times and the individual frequencies did not differ by more than 20% from the mean value. It should be noted that the CTLp frequency in immunised mice are directly correlated with tumour protection (28).

2.6 Inhibition ELISA

An antibody inhibition ELISA was performed to compare the activity of HMFG before and after conjugation to mannan. Polyvinyl chloride plates were coated with 70 μl of 10 μg/ml HMFG in bicarbonate buffer (0.2M, pH9.0) overnight at 4° C. or 1 hr at 37° C. and non-specific binding was blocked with 2% bovine serum albumin (BSA). Various concentrations of HMFG or mannan-HMFG were incubated with anti-MUC1 antibody (VA2 [57], 1/200 supernatant) for 3 hr and 100 μl was added to PVC microtitre well plates coated with HMFG. After washing with phosphate buffered saline (PBS) containing 0.05% Tween 20, 50 μl of sheep anti-mouse immunoglobulin conjugated to horseradish peroxidase (Amersham, UK) was added and incubated for a further 1 hr at RT. After washing with PBS/Tween20, the plate was developed with the chromogenic substrate 2,2''-azino-di(3-ethylbenzthiazoline) sulphonate (ABTS) (Amersham, UK) and the absorption at 405 nm recorded.

2.7 Radioimmunoassay

A sandwich radioimmunoassay was performed to ascertain that the mannan was covalently linked to HMFG. A microtitre plate was coated with serial dilutions of anti-MUC1 antibody (BC2 [58]) in bicarbonate buffer overnight and non-specific binding blocked as described above. HMFG or Mannan-HMFG was then added to the wells and incubated for 1 hr at RT followed by washing extensively with PBS containing 0.05% Tween 20. Fifty μl of radiolabelled concanavalin A, which binds specifically to mannan but not HMFG, was then added and the plate incubated for a further 1 hr followed by washing with PBS/Tween 20. Microscint-O (120 μl)was added to the wells, and plates counted in a β-scintillation counter.

Results 3.1 Preparation and Characterisation of mannan-HMFG

Figure 12B:
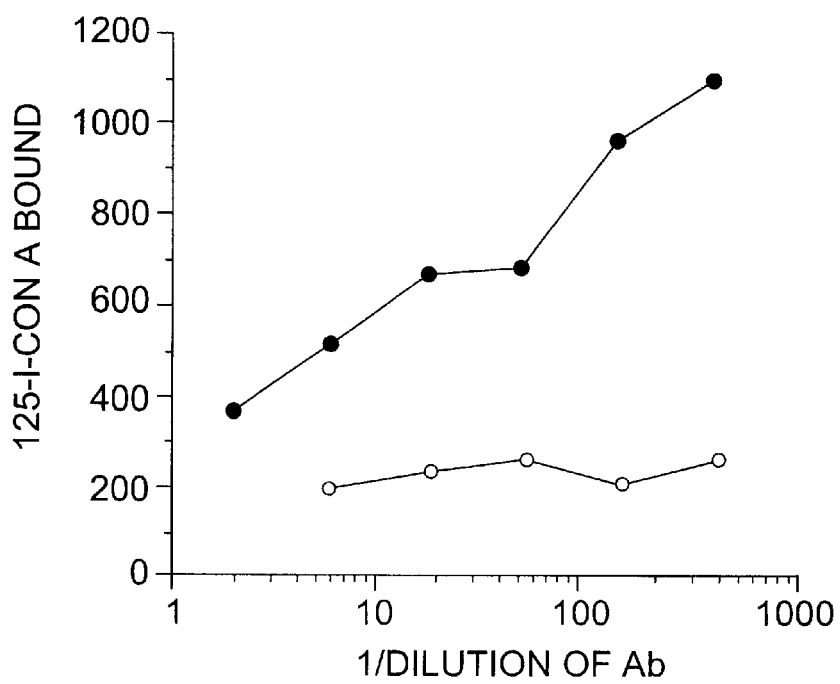

The activity of the HMFG after conjugation to mannan was determined by inhibition ELISA; the 50% inhibitory concentration for HMFG was 22 μg/ml while for the mannan-HMFG was 20 μg/ml (FIG. 12a), ie HMFG retained full reactivity after conjugation to mannan. The integrity of the mannan-HMFG complex was shown by a sandwich radioimmunoassay using anti-MUC1 antibody bound to the plate and $^{125}$I-labelled Con-A for the read out (FIG. 12b). Non-conjugated HMFG did not bind $^{125}$I-Con-A while mannan-HMFG bound demonstrating mannan to be linked to HMFG.

3.2 CTL Responses to mannan-HMFG in BALB/c Mice

Spleen cells, from BALB/c mice immunised with mannan-HMFG, were stimulated in vitro with different peptides (from both VNTR and non-VNTR regions, Table 4) and CTLp were determined by testing on target cells expressing native MUC1 (Table 5). It was apparent that immunisation with mannan-HMFG leads to CTL reacting with epitopes from the whole of MUC1,—ie, from both the VNTR and non-VNTR region.

The responses were:

a) HMFG. When whole MUC1 (HMFG) protein was used as the source of stimulating peptides, a CTLp frequency of 1/9,700 was obtained. Clearly HMFG is immunogenic for CTL production in BALB/c mice and can be processed to yield peptides presented by Class I molecules.

b) VNTR. When VNTR peptides Cp13–32 and p1–30 were used to stimulate, CTLp frequencies of 1/7000 (Cp13–32) and 1/13,200 (p1–30) resulted, ie, by immunising with HMFG, anti-VNTR CTL were produced, results similar to those found previously by immunising with mannan-conjugated VNTR peptides [47]. This is the first description of such CTL obtained by immunising with native mucin which is glycosylated.

c) Extracellular regions. When in vitro stimulation was with peptides containing amino acids 31–55, 51–70, 33–103, 344–364, CTL could be detected with a frequency of 1/19,500 (31–55); 1/10,000 (51–70); 1/20,150 (33–103) and 1/36,800 (344–364). Thus CTL can be produced to non-VNTR regions from the extracellular region; this is the first description of such CTL.

d) Intracellular regions Three different, non-overlapping intracellular peptides containing amino acids 408–423, 471–493, 507–526, were examined using the approach described above. CTLp frequencies of 1/30,000 (408–423), 1/12,500 (471–493) and 1/22,500 (507–526) were obtained, amino acids 471–493 being the most effective to restimulate cytolytic cells.

To demonstrate that the CTL were specific for MUC1 sequences, and not due to non-specific killing by NK cells or other cells, P815 target cells were used with a non-MUC1 peptide, T4N1, as the pulsed antigen, CTLp either were not detected or the frequencies were ≦1/200,000 and were considered to be negative (not shown). Of the different regions, 3 were of equivalent immunogenicity (using CTLp frequency as a measure): extracellular (51–70)=VNTR (Cp13–32)=intracellular (471–493), all of which gave a high frequency of ~1/10,000.

In contrast, immunising BALB/c mice with non-conjugated HMFG, and stimulating with the VNTR peptide Cp13–32, the CTLp frequency was 1/80,500. This frequency is similar to the CTLp frequency of 1/95,000 obtained with mannan conjugated to a recombinant bacterial fusion protein containing 5 repeats of the MUC1 VNTR (47) and thus conjugation of HMFG to mannan is necessary for generating a strong CTLp frequency in mice.

3.3 CTL Responses to mannan-HMFG in C57BL/6 mice

C57BL/6 were immunised with mannan-HMFG and in vitro stimulated with the same antigens used for the BALB/c mice (Table 5). There was a CTLp frequency of 1/13,500 for whole HMFG and 1/12,500 for the VNTR region peptide p1–30 (Table 5). Of the non-VNTR extracellular peptides, CTL were detected only to one extracellular peptide (344–364) with a frequency of 1/24,500. CTL were not detected to any of the intracellular peptides. Again the specificity of the CTL were confirmed by using a non-MUC1 peptide, T4N1, for stimulation and also using the non-MUC1 transfected parent RMA cell line as the target. Thus, C57BL/6 mice can respond to both VNTR and non-VNTR peptides, but there were no responses to certain peptides to which BALB/c mice responded.

3.4 Cellular Immune Responses to mannan-HMFG in Transgenic HLA-A*0201/$K^b$ Mice Transgenic HLA-A*0201/$K^b$ mice were immunised once with mannan-HMFG (not x3 as used above), stimulated in vitro with either HMFG, the VNTR peptide (p1–30) or one of the extracellular peptides (31–55). The CTLp were measured on human EBV HLA-A*0201$^+$ cells (see below) and frequencies were 1/39,000 (HMFG), and 1/33,000 (VNTR p1–30), which compare favourably with immunisation with mannan-VNTR peptide (1/48,000) ie, whole HMFG is as immunogenic as VNTR (Table 5). Further, when an extracellular peptide (31–55) was used, the CTLp frequency was 1/40,000, ie, the same as that found for VNTR. Thus, HLA-A*0201 can present extracellular and VNTR peptides. It should be noted that, the target cell being EBV transformed B cells, which expresses HLA-A*0201 but not $H-2^b$ class I molecules (expressed by the immunised mice), the CTLs detected were restricted to HLA-A*0201 presenting MUC1 peptides.

3.5 Cellular Immune Responses to Mannan-HMFG in A2$K^b$MUC1 Double Transgenic Mice To ascertain the ability of MUC1 CTL to lyse MUC1 positive breast cancer cells A2$K^b$MUC1 double transgenic mice injected with mannan HMFG 3 times were stimulated in vitro with either HMFG, the VNTR peptide (p1–30), extracellular peptides (31–55, 344–364) or intracellular peptides (408–423, 471–493, 507–526) (Table 5). There was a CTLp frequency of 1/2,000 for the whole HMFG and 1/8,000 for the VNTR region peptide p1–30. CTL were detected to the extracellular peptides 31–55 and 344–364 with a frequency of 1/2,000 and 1/11,000 respectively. Of the intracellular peptides CTL were detected for only peptide 408–423 with a frequency of 1/20,000.

Spleens of the immunised mice were used in a direct CTL assay to ascertain specificity of the anti-MUC1 CTL. As seen in FIG. 2 MUC1 CTL lysed 55% of MUC1$^+$ MCF7 (HLA-A*0201) breast carcinoma cells at an E:T ratio of 12:1 and was reduced to 17% when incubated in the presence of cold K562 targets. The MUC1 CTL were HLA restricted as no lysis was detected when the MUC1$^+$ BT20 (HLA-A1) breast cancer cell line was used. The MUC1 CTL did not lyse the MUC1 -ve melanoma cell line ME272.

Thus, immunisation of A2$K^b$MUC1 mice with mannan-HMFG resulted in specific Class I restricted CTL that can lyse tumour cells expressing native MUC1 and moreover anti-MUC1 CTL can be generated in mice in the presence of endogenously expressed human MUC1.

3.6 T Cell Epitope Prediction and Mapping

Figure 14A:
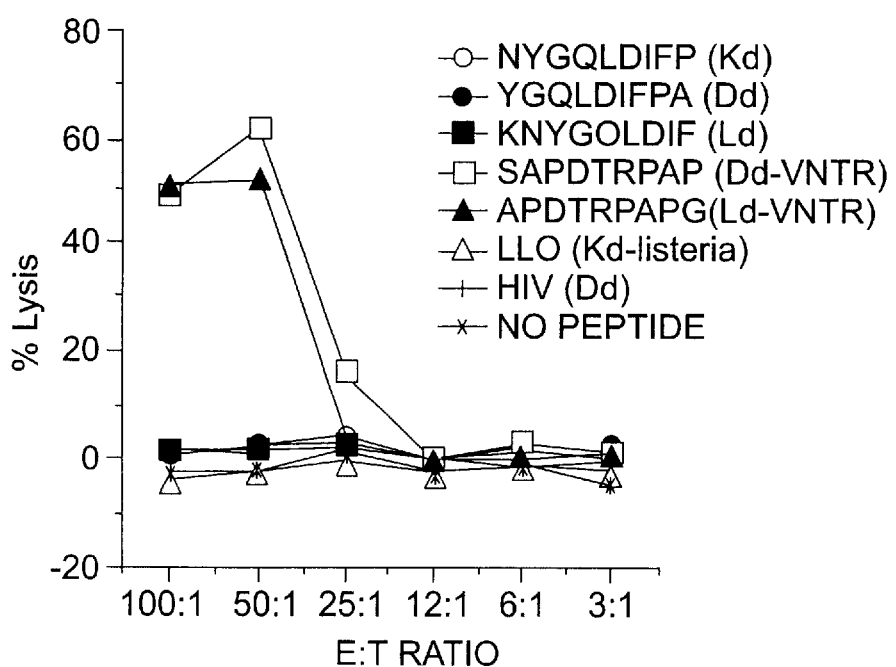

To precisely map the T cell epitopes involved in CTLp generation, a large number of overlapping 9-mer peptides would have to be synthesised and used in CTL assays. Instead, a CTL epitope prediction program was used to select putative immunogenic peptides and these were synthesised to test their antigenicity. Predicted H-2d-restricted petides (intracellular region MUC1) Several peptides (NYGQLDIFP($K^d$)SEQ ID NO: 26, YGQLDIFPA($D^d$)SEQ ID NO: 27, KNYGQLDIF($L^d$)SEQ ID NO: 28) were contained in 471–493 (CTLp frequency=1/12,500) and had predicted scores 6, 6 and 10 respectively (Table 6). To ascertain if the predicted 9-mers are presented by the Class I molecules, cytotoxic T cell assays were performed using spleen cells from mannan-HMFG immunised mice as effectors and P815 target cells were pulsed with the synthetic peptides. These were NYGQLDIFP(Kd)SEQ ID NO: 26, YGQLDIFPA(Dd)SEQ ID NO: 27, KNYGQLDIF(Ld)SEQ ID NO: 28. The pulsed cells were not lysed by Mannan-HMFG derived CTL from BALB/c mice (FIG. 14a), ie, the CTL epitopes were not predicted accurately by the algorithm. The MUC1 VNTR peptides SAPDTRPAP(Dd)SEQ ID NO: 29 and APDTRPAPG (Ld) SEQ ID NO: 8 identified previously as CTL epitopes in the VNTR region [38], were used as positive controls and 62% and 50% lysis at an E:T ratio of 50:1 was obtained. The listeriolysin Kd peptide (GYKDGNEYI) SEQ ID NO: 30 and HIV Dd peptide RKSIRIQRGPGRAFVTIGKGKGKGY SEQ ID NO: 31, used as negative controls, did not give rise to lysis (FIG. 14a).

Predicted H-2d-restricted peptides (extracellular region MUC1)

Figure 14B:
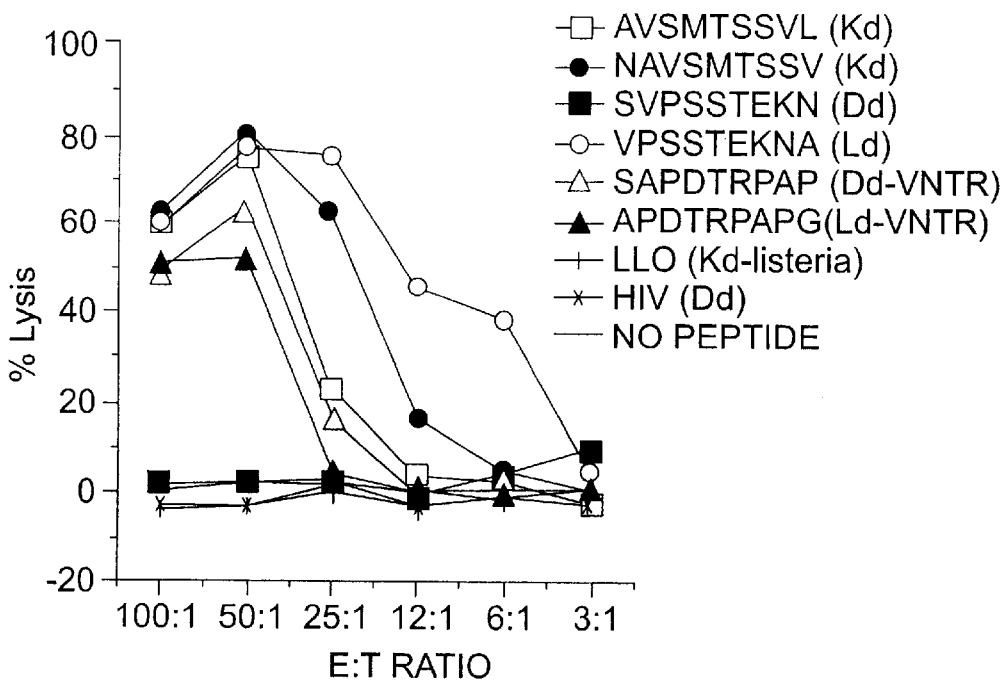
Figure 14C:
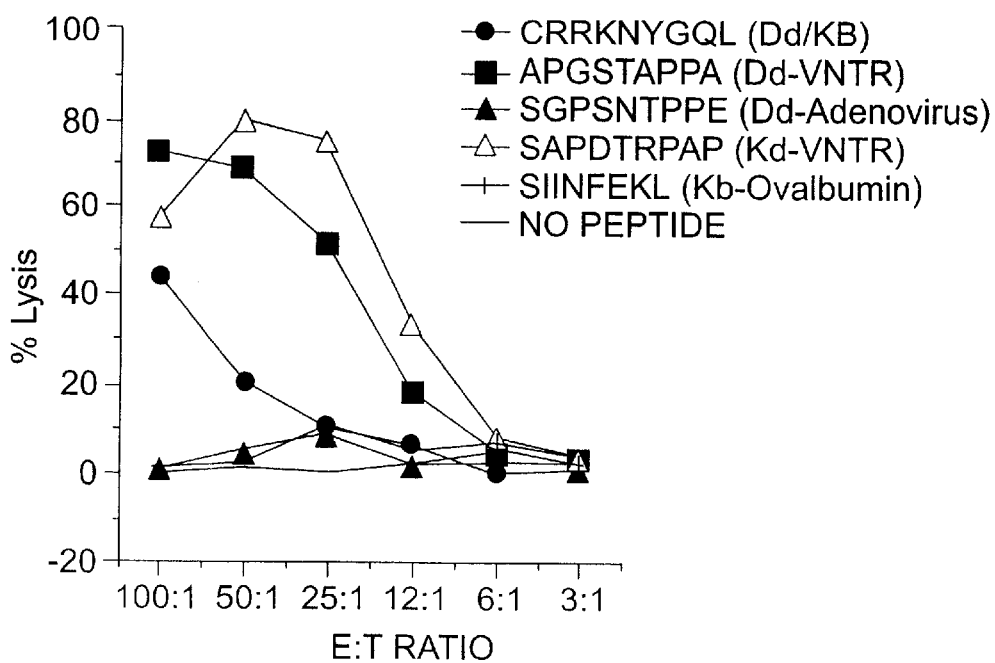
Figure 14D:
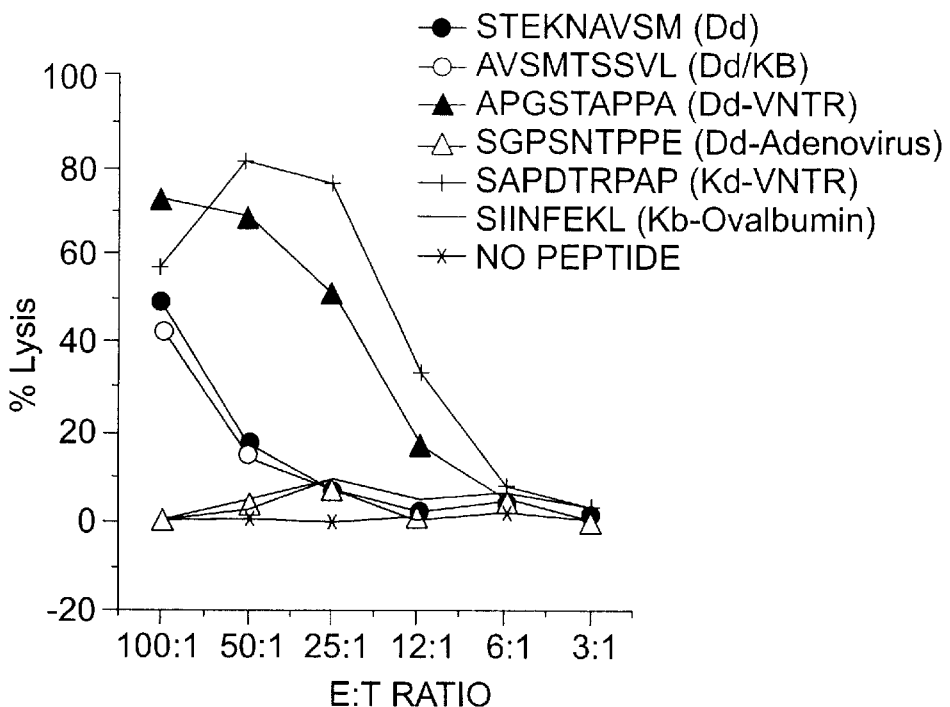

A number of 9-mer peptides in the extracellular region are predicted to be CTL epitopes [(AVSMTSSVL(Kd)SEQ ID NO: 32, TTQGQDVTL(Kd)SEQ ID NO: 33, NAVSMTSSV (Kd)SEQ ID NO: 34, TSATQRSSV(Kd)SEQ ID NO: 35, SSTTQGQDV(Kd)SEQ ID NO: 36, SVPSSTEKN(Dd)SEQ ID NO: 37, EPASGSAAT(Ld)SEQ ID NO: 38, SPGSGSSTT(Ld)SEQ ID NO: 39, VPSSTEKNA(Ld)SEQ ID NO: 40, TPGGEKETS(Ld)SEQ ID NO: 41, TSATQRSSV(Ld)SEQ ID NO: 35, SSTTQGQDV(Ld)SEQ ID NO: 36 and were contained in peptide 33–103 (CTLp frequency=1/20,150) with scores of 58, 40, 29, 10, 10, 2.9, 39, 39, 36, 30, 10 and 10) respectively. A subset of these peptides were also contained in the 51–70 peptide(CTLp frequency=1/10,000) (Table 6). Of these, four were made (AVSMTSSVL(Kd)SEQ ID NO: 32, NAVSMTSSV(Kd) SEQ ID NO: 34, VPSSTEKNA(Ld)SEQ ID NO: 40, SVPSSTEKN (Dd)SEQ ID NO: 37) and tested. Three of the four peptides were indeed presented and one was not. The synthetic peptides AVSMTSSVL(Kd)SEQ ID NO: 32, NAVSMTSSV(Kd) SEQ ID NO: 34 and VPSSTEKNA(Ld) SEQ ID NO: 40 sensitised P815 target cells with 77%, 80% and 78% lysis at E:T of 50:1 respectively, while SVPSSTEKN SEQ ID NO: 37 (with the lowest predictive value) was inactive (FIG. 14b). Therefore, AVSMTSSVL SEQ ID NO: 32, VPSSTEKNA SEQ ID NO: 40 and NAVSMTSSV SEQ ID NO: 34 are CTL epitopes in peptides 33–103 and 51–70. Predicted H-2b restricted peptides. Even though there were fewer identified peptide epitopes for C57BL/6 mice, there are a large number of potential CTL epitopes present in the peptides, albeit with low scores (Table 6). The 9-mer CRRKNYGQL SEQ ID NO: 42(Db, Kb) was contained in 471–493 (CTLp not detected) and had scores of 10 and 1.4. It weakly sensitised RMA targets to lysis by mannan-HMFG CTL with 20% lysis at a E:T of 50:1 and 42% lysis at E:T of 100:1 (FIG. 14c). The MUC1 VNTR peptides APGSTAPPA (Db) SEQ ID NO: 43 and SAPDTR-PAP (Kb)SEQ ID NO: 29 were used as positive specificity controls, where lysis of 70% and 80% were obtained while no lysis was detected for the ovalbumin Kb 9-mer SIINFEKL and Adenovirus Db 9 mer (used as negative specificity controls). The 9-mer peptides STEKNAVSM(Db) SEQ ID NO: 44, AVSMTSSVL(Db) SEQ ID NO: 32 and AVSMTSSVL(Kb) SEQ ID NO: 32 were contained in the peptides 33–103 and 51–70 with scores of 15, 10 and 1.2. All of these three peptides weakly sensitised RMA targets to lysis (~20% at 50:1 and ~40% lysis at E:T of 100:1) (FIG. 14d). There were no CTL reactive to peptides 31–55 and 51–70 in C57BL/6 mice.

Figure 14E:
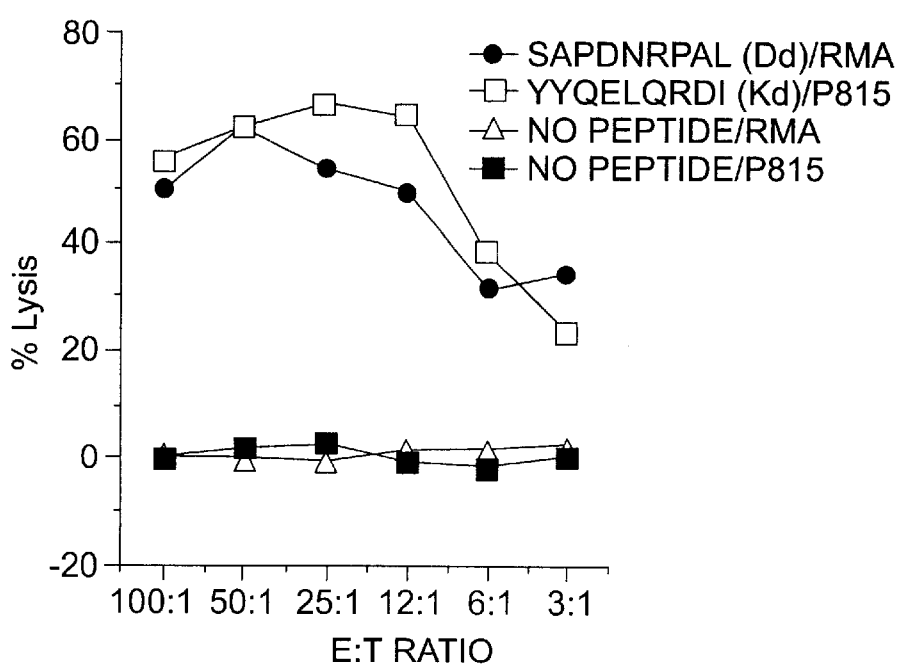

Two high scoring CTL epitopes predicted from the whole MUC1 molecule from the intracellular region (YYQELQRDI(Kd)SEQ ID NO: 18 score 2880) and extracellular region N-terminal to the VNTR (SAPDNRPAL(Db) SEQ ID NO: 13 score 4723) with scores of 2880 and 4723 sensitized RMA and P815 target cells to 50% lysis at an E:T of 50:1 (FIG. 14e). Therefore, several T cell epitopes are present in the non VNTR regions of the MUC1 molecule and as 9-mer peptides can be presented by target cells to CTL generated by mannan-HMFG immunisation.

4. Discussion

Previous immunisation studies by the inventors used a MUC1 fusion protein containing 5 repeats of the VNTR linked to mannan (MFP) and this generated strong cellular responses to MUC1 characterised by the production of IFN-γ, IL-12, very little IgG$_{2a}$ antibody and protection from tumour growth [36, 48]. Immune responses in humans have also shown promise for the therapeutic use of MUC1 antigens as in a Phase I clinical trial using MFP, 4 of 15 patients generated proliferative responses, 13 of 25 showed high levels of MUC1 specific serum antibody and 2 of 10 generated CTL to MUC1 [59]. However, in vitro peptide binding studies and in vivo studies using transgenic HLA-A*0201 mice demonstrated that the VNTR sequences can only be presented by HLA-A*0201 and HLA-A*1101 [39, 60], and studies thus far have concentrated on the MUC1 VNTR because of its preferential immunogenicity in mice, at least for antibodies, and because of evidence from humans implicating the VNTR in immune responses. Other protein sequences of MUC1 have not been examined for their cellular immunity. In the past, the inventors have sought monoclonal antibodies to non-VNTR regions in mice immunised with MUC1: none resulted and none were found in an international study. Scanning the whole MUC1 sequence for potential T cell epitopes predicted many previously untested peptides. The inventors have therefore immunised mice with mannan conjugated HMFG, to provide all possible MUC1 epitopes but dependent on natural antigen processing for their presentation, and showed that cellular immune responses to the non-VNTR regions of the MUC1 can be generated which are as effective as those generated to the VNTR and further both HLA-A*0201 and A2K$^b$MUC1 transgenic mice could be immunised, indicating that humans may also be able to be immunised.

Cellular responses could be detected to the extracellular region of MUC1, the VNTR and also to intracellular peptides in mannan-HMFG immunised BALB/c, C57BL/6, HLA-A*0201/Kb and double transgenic A2K$^b$MUC1 mice. Immunised BALB/c mice developed CTL that could respond to more non-VNTR CTL epitopes than C57BL/6 mice, in which only the 344–364 peptide and SAPDNRPAL SEQ ID NO: 13 was recognised by CTL (Table 5, FIG. 14e).

Of the various peptides used for restimulation, several possible candidate 9-mer epitopes could be predicted using the peptide motif search program (Table 6). In BALB/c mice, the precursor frequency for the 471–493 peptide was 1/12,500, however the predicted epitope peptides NYGQLDIFP SEQ ID NO: 26, YGQLDIFPA SEQ ID NO: 27 and KNYGQLDIF SEQ ID NO: 28 were not able to sensitise P81 5 targets for lysis by mannan-HMFG CTL (FIG. 14a). Therefore, either the stimulating CTL epitope was not correctly identified by the algorithm or these synthetic peptides were not appropriately processed and presented by the target cells. In contrast, several 9-mers present in the 33–103 and 51–70 sequences (AVSMTSSVL, SEQ ID NO: 32 NAVSMTSSV SEQ ID NO: 34 and VPSSTEKNA SEQ D NO: 40) were identified as functional CTL epitopes in the lysis assays (FIG. 14b).

In C57BL/6 mice, the CRRKNYGQL SEQ ID NO: 42, STEKNAVSM SEQ ID NO: 44 and AVSMTSSVL SEQ ID NO: 32 peptides from the 51–70 and 471–493 sequences sensitised RMA cells for lysis however no CTl-p were identified by restimulation with the larger peptides. This observation could result from the three 9-mers not being processed and presented by the MUC1+ cells.

Further analysis of the entire MUC1 sequence using the T cell epitope algorithm for mouse K$^d$, D$^d$, L$^d$, K$^b$, D$^b$, K$^k$, and human HLA-A1, HLA-A*0201, HLA-A3 and HLA-A24 epitopes show several candidate 9-mers for presentation by mouse or human cells. Of these 9-mer peptides, SAPIDNRPAL (D$^b$) SEQ ID NO: 13 and YYQELRDI (K$^d$) SEQ ID NO: 18 were synthesised and both were very efficient in sensitising P815 or RMA cells for lysis by mannan-HMFG CTL (FIG. 14e). It is apparent in this study and others that the prediction of CTL epitopes is not always accurate. A comparison of the predicted and experimentally determined T cell epitopes for the VNTR region illustrates that the lower scores do not necessarily predict a lack of presentation or antigenicity (Table 7). For example, SAPDTRPAP SEQ ID NO: 29 peptide has been confirmed to be a Kb-restricted epitope by class I stabilisation when incubated with the TAP defective RMA-S cells as well as by lysis of peptide pulsed RMA cells (FIG. 14c), however the predicted score is only 0.004 ([38]). Similarly, the K$^k$, L$^d$ and D$^d$ was not predicted accurately [38]. The HLA-A*0201 T cell epitope, STAPPAHGV SEQ ID NO: 45 identified independently by epitope mapping [39] was predicted albeit with a low score. The prediction algorithms act as a guide, to the probability of antigen presentation, but the in vivo response will be defined by antigen processing, immunodominance, T-cell repertoire, glycosylation and other unknown factors [61, 62].

The whole MUC1 protein in purified form has not previously been used to immunise mice to generate cellular immunity, although several other immunisation methods have been used. The whole MUC1 protein has been delivered in a vaccinia construct [46, 63], as a construct in DNA immunisation [64], in transfected dendritic cells [65] and in transfected EBV-B cells [66]. In none of these studies was the specificity of the CTL ascertained. However, the importance of using glycosylated MUC1 (as HMFG) should be stressed. Other studies, in mice and humans have used non-glycosylated peptides which have led to antibody production in both MUC1 transgenic mice [67] and in humans [59, 68, 69]; in these studies it was considered that B cell and at times T cell tolerance had been overcome but, with respect to antibodies, the non-glycosylated peptides represent novel antigens and the response is not surprising. However, in the studies described herein, native glycosylated mucin (HMFG) linked to mannan successfully primed CTL in several strains of mice including A2K$^b$MUC1 transgenic mice. Mannan-HMFG gave a higher CTLp frequency in A2K$^b$MUC1 mice (1/2000) compared to BALB/c or C57Bl/6 mice and could be due to either the different strain of mice or to the presence of a higher affinity HLA-A*0201 CTL epitope. In BALB/c mice HMFG gave a CTLp frequency of 1/80,500. This was comparable to the CTLp frequency in mice immunised with a non-glycosylated form of MUC1 VNTR [47], ie, both glycosylated and non-glycosylated forms of the VNTR were equally immunogenic provided they are presented with oxidised mannan. Clearly, the carbohydrate coating did not obscure the underlying peptide. Thus, mannan-HMFG is able to break tolerance in A2K$^b$MUC1 transgenic mice by producing CTLs to peptides in the VNTR, the extracellular region and the intracellular region in MUC1. These results reinforce the concept that MUC1 should be a useful target in therapy.

The use of mannan-HMFG in humans warrants some discussion in that MUC1 is a present on some normal cells such as pancreas, kidney. Hence it is possible that immune responses may be generated to these tissues and give rise to autoimmunity. Thus far in our clinical trials using MUC1 VNTR conjugated to mannan no autoimmunity was detected, however, careful dose escalation studies and monitoring is necessary [59]. The HMFG obtained directly from donors is likely to be less preferred for use and recombinant material may be more appropriate. However using recombinant material, the high level of glycosylation of the HMFG should be kept in mind. Presumably, a eukaryotic vector will be necessary. Thirdly, the inventors have recently shown that the VNTR peptides can deviate the immune response towards antibodies, because of a cross reaction with existing, natural human antibodies [70]. Such a deviation may occur when using whole MUC1.

EXAMPLE 10

The non-VNTR peptides were coupled to keyhole limpet hemocyanin (KLH) using gluteraldehyde and then reacted with oxidised mannan as follows: Two mg of the peptide 471 or 507 was dissolved in 1.75 ml phosphate buffer and mixed with 0.25 ml KLH (2 mg/ml), treated with 1 ml of 0.25% glutaraldehyde and allowed to mix in the dark overnight at room temperature. The mixture was dialysed into phosphate buffer overnight. The dialysed mixture was mixed with 1 ml oxidised mannan prepared as described in European Patent Application No. 94303817.4 and allowed to stand overnight.

BALB/c mice (6–8 weeks) were immunised intraperitoneally with 5 micrograms Mannan-peptide KLH on days 0, 10 and 17 and CTL activity in splenocytes determined as described. Non-VNTR peptide conjugated to mannan showed positive responses in the CTL assay (FIGS. 15 & 16) compared to the positive controls (VNTR peptides conjugated to mannan).

REFERENCES

1. Gendler, S., Papadimitriou, J. T., Duhig, T., Rothbard, J. & Burchell, J., *A highly immunogenic region of a human polymorphic epithelial mucin expressed by carcinomas is made up of tandem repeats.*, J. Blot. Chem., 263:12820–12823,1988.
2. Harisch, F. G. & Uhlenbruck, G., *Structures of Neutral O-Linked polylactosaminoglycans on human skim milk mucins*, I. Biol. Chem., 264: 872–883, 1989.
3. Marjolijn, J. L., Ligtenberg, M. 1. L., Vos, H. L., Annemiek, M. C., Gennissen, A. M. C. & Hilkens, J. Episialin, *A carcinoma-associated much is generated by a polymorphic gene encoding splice variants with alternating amino termini*, J. Biol. Chem., 265:5573–5578, 1990.
4. Crocker, G. & Price, M. R., *Genetic polymorphism of high molecular weight glycoproteins: A comparative study in normal individuals and breast cancer patients*, Br. J. Cancer, 55:651–652, 1987.
5. Barnd, D. L., Lan, M. S., Metzgar, R. S., Finn, O. J., *Specific, major histocompatibiliiy complex-unrestricted recognition of tumour-associated mucins by human cytotoxic T-cells*, Proc. Natl. Acad. Sd., 86:7159–7163, 1989.
6. Jerome, K. R., Barnd, D. L., Boyer, C. M., Taylor-Papadimitriou, J., McKenzie, I. F. C., Bast, R, C., and Finn, O. J., *Adenocarcinoma reactive cytotoxic T-lymphocytes recognize an epitope present on the protein core of epithelial mucin molecules. Cellular immunity and immunotherapy of cancer*, 321–328, 1990.
7. Sambrook, et al., *Molecular Cloning: A Labo rat oty Manual*, Cold Spring Harbor Press, Cold Spring Harbor, 1989.
8. Xing, P. X., Tjandra, J. J., Stacker, S. A., Teh, J. O., Thompson, C. H., McLaughlin, P. J., and McKenzie, I. F. C., *Monoclonal antibodies reactive with mucin expressed in breast cancer*, Immunol. Cell Biol., 67:183–185, 1989.
9. Apostolopoulos, V., Xing, P. X., Trapani, J. A. and McKenzie, I. F. C., *Production of anti-breast cancer monoclonal antibodies using a glutathione-S-transferase-MUCJ bacterial fusion protein*, Br. J. Cancer, 67:713–720, 1993.
10. Siddiqui, J., Abe, M., Hayes, D., Shani, E., Yunis, E. & Kufe, D., *Isolation and sequencing of a cDNA coding for the human DF3 breast carcinoma-associated antigen*, Proc. Natl. Acad. Sci., 85:2320–2323, 1988.
11. Smith, D. B. & Johnson, K. S., *Single-step purfication of polypeptides expressed in Escherichia coli as fusions with glutathione S-transferase*, Gene, 67:31–40, 1988.
12. Tomonari, K. *A rat antibody against a structure functionally related to the mouse Tcell eceptoe/T3 complex*, Immunogenetics, 28:455458, 1988.
13. Pierres, A., Naquet, P., Van Agthoven, A., Bekkhoucha, F., Denizot, F., Mishal, Z., Schmitt-Verhulst, A-M. and Pierres, M., *A rat anti-mouse T4 monoclonal antibody (H129. 19) inhibits the proliferation of Ia-reactive T-cell clones and delineates two phenotypically distinct (7'4+, Lyt-2, 3-, and T4-, Lyt-2,3+) subsets among anti-Ia cytolytic T-cell clones*, J. Immunol., 132:2775–2782, 1984
14. Ledbetter, J. A. and Herzenberg, L. A., *Xenogeneic monoclonal antibodies to mouse lymphoid differentiation antigens*, Immunol. Rev., 47:63–90, 1979.
15. Harlow, D. and Lane, D., *A Laboratory Manual*, E. Harlow and D. Lane eds. Cold Spring Harbor Laboratory Press, Cold Spring Harbor, N.Y., 271, 1988.
16. Apostolopoulos, V., Xing, P. X., Trapani, J. A. and McKenzie, I. F. C., *Production of anti-breast cancer monoclonal antibodies using a glutathione-S-transferase-MUC1 bacterial fusion protein*, Br. J. Cancer, 67(4):713–720, 1993.
17. Xing, P. X., Tjandra, J. J., Stacker, S. A., Teh, J. O., Thompson, C. H., McLaughlin, P. J., and McKenzie, I. F. C., *Monoclonal antibodies reactive with mucin expressed in breast cancer*, Immunol. Cell Biol., 67:183–185, 1989.
18. Devine, P. L., Clark, B. A., Birrell, O. W., Layton, O. T., Ward, B. O, Alewood, P. F. and McKenzie, I. F. C., *The breast tumor-associated epitope defined by monoclonal antibody 3E1. 2 is an O-linked mucin carbohydrate containing N-glycolylneuramic acid*, Cancer Res., 51:5826–5836, 1991.
19. Hareuvem, M., Gautier, C., Kieny, M. P., Wreschner, D., Chambon, P. and Lathe, R., *Vaccination against tumor cells expressing breast cancer epithelial tumor antigen*, Proc. Natl. Acad. Sci. USA, 87:9498–9502, 1990.

20. Pierres, A., Naquet, P., VanAgthoven, A., Bekkhoucha, F., Denizot, F., Mishal, Z., Schmitt-Verhulst, A-M. and Pierres, M., *A rat anti-mouse T4 monoclonal antibody (H129. 19) inhibits the proliferation of Ia-reactive T-cell clones and delineates two phenoiypically distinct (T4+, Lyt-2,3-, and T4-, Lyt-2,3k) subsets among anti-Ia cytolytic T-cell clones, J. Immunol.,* 132:2775–2782,1984
21. Miller, R. A. and Stutman, O., *Monoclonal antibody to Lyt 2 antigen blocks H-5 21- and H-2K-specific mouse cytotoxic T-cells, Nature,* 296:76–78, 1982.
22. Tomonari, K., *A rat antibody against a structure functionally related to the mouse T-cell receptor/T3 complex, Immunogenetics,* 28:455–458, 1988.
23. Auchincloss, H., Moses, R., Conti, D., Sundt, T., Smith, C., Sachs, D. H. and Winn, H. J., *Rejection of transgenic skin expressing a xeno-classI antigen is CD4-dependent and CD8-independent, Transpl. Proc.,* 22(3): 1059–1060, 1990.
24. Pierres, A., Naquet, P., Van Agthoven, A., Bekkhoucha, F., Denizot, F., Mishal, Z., Schmitt-Verhulst, A-M. and Pierres, M., *A rat anti-mouse T4 monoclonal antibody (H129. 19) inhibits the prol(feration of Ia-reactive T-cell clones and delineates two phenoiypically distinct (T4+, Lyt-2, 3-, and T4-, Lyt-2,3+) subsets among anti-Ia cytolytic T-cell clones, J. Immunol.* 132:2775–2782, 1984.
25. Ledbetter, J. A. and Herzenberg, L. A., *Xenogeneic monoclonal antibodies to mouse lymphoid differentiation antigens, Immunol. Rev.,* 47:63–90,1979.
26. Apostolopoulos, V., Xing, P. X, and McKenzie 1. F. C., *New Trends in the Development of a Breast Cancer Vaccine, Cancer Forum,* 17:11–116, 1993.
27. Bobek, L. A., Tsai, H., Besbrock A. R., Levine, M. 1., *Molecular Cloning Sequence and Specificity of Expression of the Gene Encoding the Low Molecular Weight Human Salivary Mucin (MUC7), J. Bid. Chem.,* 268:20563–20569,1993.
28. Mandelboimo, O., Berke O., Fridkin, M., Feldman, M., Eisenstein, M., and Eisenbachd L_*CTh Induction by a Tumour-a c.coci ated Antigen Octapeptide Derived from a Murine Lung Carcinoma, Nature,* 369,67–71, 1994.
29. Goodman G E, Helistrom I, Yelton D E, Murray J L, O'Hara S, Meaker E, Zeigler L, Palazollo P, Nicaise C, Usakewicz J et al. Phase I trial of chimeric (human-mouse) monoclonal antibody L6 in patients with non-small-cell lung, colon, and breast cancer. Cancer Immunol. Immunother. 19936 36:267–273.
30. Apostolopoulos V, McKenzie I F C. Cellular mucins: targets for immunotherapy. Crit. Rev. Immunol. 1994; 14:293–309.
31. Finn O J, Jerome K R, Henderson R A, Pecher G, Domenech N, Magarian-Blander J, Barratt-Boyes S M. MUC-1 epithelial tumor mucin-based immunity and cancer vaccines. Immunol. Rev. 1995; 145:61–89.
32. Schrier D M, Stemmer S M, Johnson T, Kasliwal R, Lear J, Matthes S, Taffs S, Dufton C, Glenn S D, Butchko G et al. High-dose 90Y Mx diethylenetriaminepentaacetic acid (DTPA)-BrE-3 and autologous hematopoietic stem cell support (AHSCS) for the treatment of advanced breast cancer: a phase I trial. Cancer Res. 1995;55(23 Suppl) :5921S–5924S.
33. Richman C M, DeNardo S J, O'Grady L F, DeNardo G L. Radioimmunotherapy for breast cancer using escalating fractionated doses of $^{131}$I-labeled chimeric L6 antibody with peripheral blood progenitor cell transfusions. Cancer Immunol. Immunother. 1993;36: 267–273.
34. MacLean G D, Miles D W, Rubens R D, Reddish M A, Longenecker B M. Enhancing the effect of THERATOPE STn-KLH cancer vaccine in patients with metastatic breast cancer by pretreatment with low-dose intravenous cyclophosphamide. Immunother. Emphasis Tumor Immunol. 1996;19:309–316.
35. Apostolopoulos V, McKenzie I F C, Pietersz G A. Breast cancer immunotherapy-Current status and Future prospects. Immunol. Cell. Biol. 1996;74:457–464.
36. Apostolopoulos V, Pietersz G A, Loveland B E, Sandrin M S, McKenzie I F C. Oxidative/reductive conjugation of mannan to antigen selects for $T_1$ or $T_2$ immune responses. P.N.A.S. USA 1995;92:10128–10132.
37. Apostolopoulos V, Loveland B E, Pietersz G A, McKenzie I F C. CTL in mice immunized with human Mucin 1 are MHC-restricted. J. Immunol. 1995;1155:5089–5094.
38. Apostolopoulos V, Haurum J, McKenzie I F C. MUC1 peptide epitopes associated with 5 different H2 class I molecules. Eur. J. Immunol. 1997;27:2579–2587.
39. Apostolopoulos V, Karanikas V, Haurum J S, McKenzie I F C. Induction of HLA-A2-restricted CTLs to the Mucin 1 human breast cancer antigen. J. Immunol. 1997;159:5211–5218.
40. McKenzie I F C, Xing P-X. Mucins in Breast Cancer-Recent Advances. Cancer Cells 1990;2:75–78.
41. Jerome K R, Barnd D L, Boyer C M, Papadimitriou J T, McKenzie I F C, Bast R C, Finn O J. Adenocarcinoma reactive cytotoxic T lymphocytes recognise an epitope present on the protein core of epithelial mucin molecules. Cellular Immunity and Immunotherapy of Cancer 1990;321–328.
42. Barnd D L, Lan M S, Metzgar R S, Finn O J. Specific major histocompatibility complex-unrestricted recognition of Tumor-associated mucins by human cytotoxic T cells. P.N.A.S. USA 1989;86:7159–7163.
43. Acres B., Apostolopoulos V., Balloul J M., Wreschner D., Xing P X., Hadji D A., Spetz J F., Bisouarne N., Kieny M P and McKenzie I F C. MUC1 specific cytotoxic T cell precursor analysis in human MUC1 transgenic mice immunised with human MUC1 vaccines. Cancer Immunol. Immunother. (In Press)
44. Vitiello A, Marchesini D, Furze J, Sherman L A, Chesnut R W. Analysis of the HLA-restricted influenza-specific cytotoxic T lymphocyte response in transgenic mice carrying a chimeric human-murine class I major histocompatibility complex. J. Exp. Med. 1991;173:1007.
45. Graham R A, Stewart L S, Peat N P, Beverley P, Taylor-Papadimitriou J. MUC1-based immunogens for tumor therapy: development of murine model systems. Tumor Targeting 1995;1:211.
46. Acres R B, Hareuveni M, Balloul J M, Kieny M P. Vaccinia virus MUC1 immunization of mice: immune response and protection against the growth of murine tumors bearing the MUC1 antigen. J. Immunother. 1993;14:136–143.
47. Jarasch E, Bruder G, Keenan T W, Franke W W. Redox constituents in milk fat globule membranes and rough endoplasmic reticulum from lactating gland. J. Cell Biol. 1977;73:223–241.
48. Apostolopoulos V, Pietersz G A, McKenzie I F C. Cell-mediated immune responses to MUC1 fusion protein coupled to mannan. Vaccine 1996;74:930–938.

49. Parker K C, Bednarek M A, Hull L K, Utz U, Cunningham B, Zweerink H J, Biddison W E, Coligan J E. Sequence motifs important for peptide binding to the human MHC class I molecule, HLA-A2. J. Immunol. 1992;149:3580–3587.
50. Parker K C, Bednarek M A, Coligan J E. Scheme for ranking potential HLA-A2 binding peptides based on independent binding of individual peptide side-chains. J. Immunol. 1994;152:163–175.
51. Screpanti I, Felli M P, Toniato E, Meco D, Martinotti S, Frati L, Santoni A, Gulino A. Enhancement of natural-killer-cell susceptibility of human breast-cancer cells by estradiol and v-Ha-ras oncogene. Int. J. Cancer 1991;47:445–449.
52. Chen Q, Jackson H, Gibbs P., Davis I D, Trapani J, Cebon J. Spontaneous T cell responses to melanoma differentiation antigens from melanoma patients and healthy subjects. Cancer Immunol. Immunother. 1998;47:191–197.
53. Taswell, C. Limiting dilution assays for the determination of immunocompetent cell frequencies. I. Data analysis. J. Immunol. 1981;126:1614–1619.
54. Fazekas de St. Groth S. The evaluation of limiting dilution assays. J. Immunol. Methods 1982;49:R11.
55. Lefkovits I, Waldmann H. Limiting dilution analysis of the cells of the immune system. I. The clonal basis of the immune response. J. Immunol. Today 1984;5:265.
56. Pietersz G A, Wenjun L, Popovski V, Apostolopoulos V, and McKenzie I F C. Parameters for using mannan-MUC1 fusion protein to induce cellular immunity. Cancer Immunol. Immunother. 1998,45:321.
57. Apostolopoulos V, Xing P-X, Trapani J A, McKenzie I F C. Production of anti-breast cancer monoclonal antibodies using glutathione-S-transferase-MUC1 bacterial fusion protein. Brit. J. Cancer 1993;67:713–720.
58. Xing P-X, Tjandra J J, Stacker S A, Teh J G, Thompson C H, McLaughlin P J, McKenzie I F C. Monoclonal antibodies reactive with mucin expressed in breast cancer. Immunol. Cell Biol. 1989;67:183–195.
59. Karanikas V A, Hwang L, Pearson J, Ong C S, Apostolopoulos V, Vaughan H A, Xing P-X, Pietersz G A, Tait B D, Thynne G, McKenzie I F C. Immune responses of patients with adenocarcinoma vaccinated with mannan-MUC1 fusion protein. J. Clin. Invest. 1997;100:2783–2792.
60. Domenech N, Henderson R A, Finn O J. Identification of an HLA-A11-restricted epitope from the tandem repeat domain of the epithelial tumor antigen mucin. J. Immunol. 1995;155:4766–4774.
61. Lipford G B, Hoffman M, Wagner H, Heeg K. Primary in vivo responses to ovalbumin. Probing the predictive value of the $K^b$ motif. J. Immunol. 1993;150:1212–1222.
62. Pamer E G, Harty J T, Bevan M J. Precise prediction of a dominant class I MHC-restricted epitope of listeria monocytogenes. Nature 1991;353:852–855.
63. Akagi J, Hodge J W, McLaughlin J P, Gritz L, Mazzara G, Kufe D, Schlom J, Kantor J A. Therapeutic antitumor response after immunization with an admixture of recombinant vaccinia viruses expressing a modified MUC1 gene and the murine T-cell costimulatory molecule B7. J. Immunother. 1997;20:38–47.
64. Graham R A, Burchell J M, Beverley P, Taylor-Papadimitriou J. Intramuscular immunization with MUC1 cDNA can protect C57 mice challenged with MUC1-expressing syngeneic mouse Tumor cells. Int. J. Cancer 1996;65:664–670.
65. Gong J, Chen L, Chen D, Kashiwaba M, Manome Y,Tanaka T, Kufe D. Induction of antigen-specific antitumor immunity with adenovirus-transduced dendritic cells. Gene Ther. 1997;4:1023–1028.
66. Pecher G, Finn O J. Induction of cellular immunity in chimpanzees to human tumor-associated antigen mucin by vaccination with MUC-1 cDNA-transfected Epstein-Barr virus-immortalized autologous B cells. P.N.A.S. USA 1996;93:1699–1704.
67. Rowse G J, Tempero R M, VenLith M L, Hollingsworth M A, Gendler S J. Tolerance and immunity to MUC1 in a human MUC1 transgenic murine model. Cancer Res. 1998;58:315–321.
68. Goydos J S, Elder E, Whiteside T L, Finn O J, Lotze M T. A phase I trial of a synthetic mucin peptide vaccine. Induction of specific immune reactivity in patients with adenocarcinoma. J. Surg. Res. 1996; 63:298–304.
69. Reddish M, MacLean G D, Koganty R R, Kan-Mitchell J, Jones V, Mitchell M S, Longenecker B M. Anti-MUC1 class I restricted CTLs in metastatic breast cancer patients immunized with a synthetic MUC1 peptide. Int. J. Cancer 1998;76:817–823.
70. Apostolopoulos V, Osinski C., McKenzie I F C. MUC1 cross-reactive Gal α(1,3) Gal antibodies in humans switch responses from cellular to humoral. Nat. Med. 1998, 4:315–320.

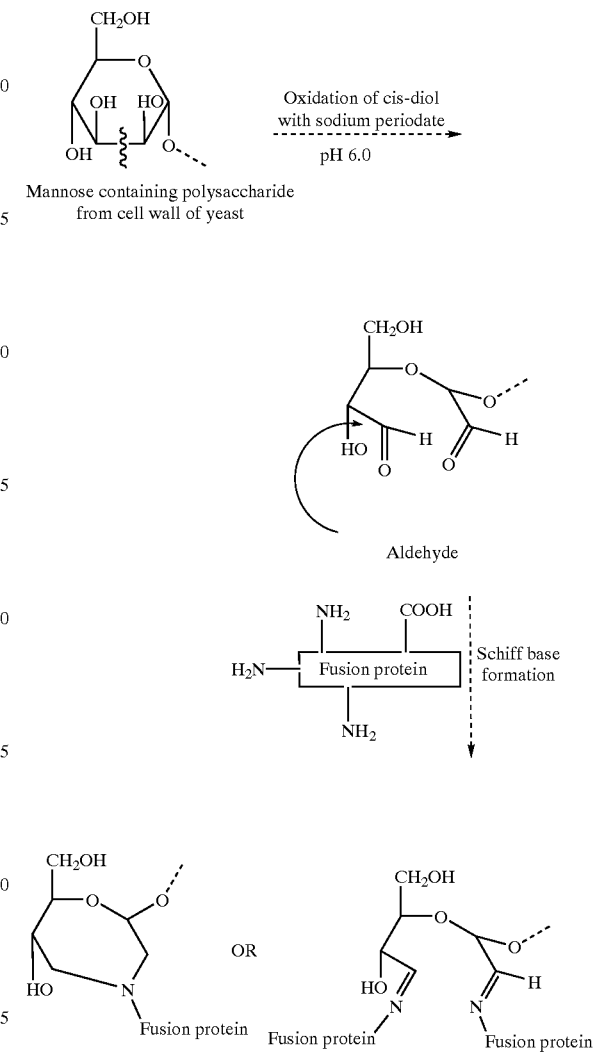

TABLE 4

Diagramatic Structure of MUC1 and Sequences of the Synthetic Peptides

```
N-Terminal      VNTR      Transmembrane    Cytoplasmic tail
┌──────────────┬┬┬┬┬─────────────────────────────────────┐
│              ││││                                       │
└──────────────┴┴┴┴┴─────────────────────────────────────┘
33                      423    452                    544
```

PDTRPAPGSTAPPAHGVTSAPDTRPAPGSTAP    SEQ. ID NO: 46
1              13              32
MUC1

Extracellular region

| | | |
|---|---|---|
| Cp13–32 | (C)PAHGVTSAPDTRPAPGSTAP | SEQ. ID NO: 19 |
| p1–30 | PDTRPAPGSTAPPAHGVTSAPDTRPAPGST | SEQ. ID NO: 47 |
| 31–55 | TGSGHASSTPGGEKETSATQRSSVP | SEQ. ID NO: 10 |
| 51–70 | RSSVPSSTEKNAVSMTSSVL | SEQ. ID NO: 11 |
| 33–103 | Glutathione-S-transferase fusion protein SGHASSTPGGEKETSATQRSSVPSSTEKNAVSMTSSVLS SHSPGSGSSTTQGQDVTLAPATEPASGSAATW | SEQ. ID NO: 12 |
| 229–237 | SAPDNRPAL | SEQ. ID NO: 13 |
| 344–364 | NSSLEDPSTDYYQELQRDISE | SEQ. ID NO: 14 |

Intracellular region

| | | |
|---|---|---|
| 408–423 | TQFNQYKTEAASRVNL | SEQ. ID NO: 15 |
| 471–493 | AVCQCRRKNYGQLDIFPARDTYH | SEQ. ID NO: 16 |
| 507–526 | (C)YVPPSSTDRSPYEKVSAGNG | SEQ. ID NO: 48 |

Mouse CD4

| | | |
|---|---|---|
| T4NI | KTLVLGKEQESAELPCECY | SEQ. ID NO: 49 |

In the peptides of the VNTR (sequence in italics) p1–30 and p13–32 the numbers refer to amino acid number in the VNTR. Other numbers (31–55, 51–70 etc) refer to the amino acid position in the published sequence.

TABLE 5

CTLp Frequencies in Spleens of Mice Immunised With mannan-HMFG

| | | CTLp Frequency Immunized Strain | | | |
|---|---|---|---|---|---|
| | | C57BL6($K^bD^b$) | BALB/c ($K^dD^dL^d$) | HLA*0201/$K^b$ | A2$K^b$MUC1 |
| | | | Target Cell | | |
| Restimulating Antigen | Peptide Details | MUC1-RMA | Target MUC1– P815 | EBV + pep | MCF7 |
| Whole MUC1 | HMFG | 1/13,500 | 1/9,700 | 1/39,000 | 1/2,000 |
| Extracellular region | Cp13–32 | ND | 1/7,000 | ND | ND |
| | p1–30 | 1/12,500 | 1/13,200 | 1/33,000 | 1/8,000 |
| | 31–55 | Not Detected | 1/19,500 | 1/40,000 | 1/2,000 |
| | 51–70 | Not Detected | 1/10,000 | ND | ND |
| | 33–103 | ND | 1/20,150 | ND | ND |
| | 344–364 | 1/24,500 | 1/36,800 | ND | 1/11,000 |
| Intracellular region | 408–423 | Not Detected | 1/30,000 | ND | 1/20,000 |
| | 471–493 | Not Detected | 1/12,500 | ND | Not detected |
| | 507–526 | Not Detected | 1/22,500 | ND | Not detected |
| Non-MUC1 | T4N1 | Not Detected | Not Detected | Not detected | Not Detected |

ND—Not done; No CTLp were detected when RMA, P815 or EBV infected lymphocytes without peptide were used as targets.

TABLE 6

Mice Immunised with mannan-HMFG: CTLp Frequencies to Various non-VNTR Peptides and their Predicted CTL Epitopes

| Peptide Used for Stimulation | CTLp Frequency | | Predicted 9-mers and Score for the Various H2 Haplotypes | | | | | | | | |
|---|---|---|---|---|---|---|---|---|---|---|---|
| | BALB/c | C57B1/6 | $K^d$ | $D^d$ | CTL | $L^d$ | CTL | $D^b$ | CTL | $K^b$ | CTL |
| 471–493 AVCQCRRKNYGQL DIFPARDTYH (16) | 1/12,500 | not detected | NYGQLDIFP 6 (26) CYVPPSSTD 12 (51) QFNQYKITEA 29 (54) QYKTEAASR 6.0 (55) TEAASRVNL 5.8 (56) | YGQLDIFPA (27) 6 VPPSSTDRS (52) 2.4 FNQYKITEAA 2.2 (57) | 0% | KNYGQLDIF (28) 10 VPPSSTDRS (52) 45 TEAASRVNL 6.0 (56) | 0% | CRRKNYGQL (42) 10 RSPYEKVSA (53) 0.99 TEAASRVNL 0.18 (56) | 20% | CRRKNYGQL (42) 1.4 VPPSSTDRS (52) 0.6 FNQYKITEAA 0.72 (57) | 20% |
| 507–526 CYVPPSSTDRSPYEKVS AGNG (48) 408–423 TGFNQYKTEAASRYNL (50) | 1/22,500 1/30,000 | not detected not detected | | | | | | | | | |
| 344–364 NSSLEDPSTDYYQELQR DISE (14) | 1/36,800 | 1/24,500 | YYQELQRDI 2880 (18) SLEDPSTDV 14 (62) | YYQELQRDI 1.8 (18) | 0% | NSSLEDPST (58) 5 DPSTDYYQE 3.6 (59) PSTDYYQEL 2.5 (60) | | SSLEDPSTD 4.4 (61) | | PSTDYYQEL 2.9 (60) YYQELQRDI (18) 1.1 | |
| 33–103 SGHASSTPGGEKETSATQ RSSVPSSTEKNAVSMTSS VLSSHSPGSGSSTTQGQD VTLAPATEPASGSAATW (12) | 1/20,150 | not done | AVSMTSSVL 58 (32) TTQGQDVTL (33) 40 NAVSMTSV (34) 29 TSATQRSSV (35) 10 SSTTQGQDV (36) 10 | SVPSSTEKN 2.9 (37) | 77% | EPASGSAAT 39 (38) SPGSGSSTT (39) 39 VPSSTEKNA (40) 36 TPGGEKETS (41) 30 TSATQRSSV (36) 10 SSTTQGQDV 10 (36) | 78% | STEKNAVSM 15 (44) AVSMTSSVL (32) 10.1 | 19% | AVSMTSSVL 1.2 (32) | 18% |
| 51–70 RSSVPSSTEKNAVSMTSSVL (11) | 1/10,000 | not detected | AVSMTSSVL (32) 58 NAVSMTSV (34) 29 STEKNVSM (44) 6.0 | SVPSSTEKN 2.9 | 80% | VPSSTEKNA (40) 36 AVSMTSSVL (32) 5.0 SSTEKNAVS (44) 5.0 NAVSMTSV (34) 2.0 | | STEKNAVSM (44) 15 AVSMTSSVL (32) 10 | 18% | AVSMTSSVL (32) 1.2 | |
| 31–55 TGSGHASSTPGGEKETSATQ RSSVP (10) | 1/19,500 | not detected | TSATQRSSV (35) 10 | GGEKETSAT (64) 2.0 TGSGHASST (65) 2.0 | | TPGGEKETS (41) 30 TSATQRSSV (35) 10 | | TSATQRSSV 2.6 (35) | | KETSATQRS (66) 0.24 | |

Numbers in parentheses are SEQ ID NOS.

TABLE 7

Experimentally Determined And Predicted Mouse and Human CTL Epitopes in The MUC1 VNTR

| Haplotype | Experimentally determined T cell epitope | Predicted Score for T cell epitope from algorithm | Predicted T cell epitopes | Predicted Score from algorithm | | |
|---|---|---|---|---|---|---|
| $K^b$ | SAPDTRPAP | 0.004 | APPAHGVTS | 0.330 | (29) | (69) |
|  |  |  | TAPPAHGVT | 0.300 |  | (70) |
| $K^d$ | ND |  | STAPPAHGV | 12.000 |  | (47) |
| $K^k$ | PDTRPAPGS | 0.200 | STAPPAHGV | 0.5 | (71) | (47) |
| $L^d$ | APDTRPAPG | 0.900 | APPAHGVTS | 45.00 | (8) |  |
|  |  |  | APGSTAPPA | 30.00 |  | (45) |
| $D^d$ | SAPDTRPAP | 0.086 | STAPPAHGV | 12.00 | (29) | (47) |
| HLA-A*0201 | STAPPAHGV | 0.966 | STAPPAHGV | 0.966 | (47) | (47) |

Numbers in Parentheses are SEQ ID NOS.

The claims defining the invention are as follows:

1. An immunogenic peptide, protein or portion thereof which is effective to elicit an immune response comprising an amino acid sequence of non-VNTR, non leader regions of mucin.

2. The immunogenic peptide, protein or portion thereof according to claim 1, the amino acid sequence of which is derived from human mucin 1.

3. The immunogenic peptide, protein or portion thereof according to claim 2, wherein said amino acid sequence is derived from HMFG.

4. The immunogenic peptide, protein or portion thereof according to claim 3, comprising one of the following amino acid sequences or an immunogenic fragment thereof:

(i) TGSGHASSTPGGEKETSATQRSSVP (SEQ ID No: 10)

(ii) RSSVPSSTEKNAVSMTSSVL (SEQ ID No: 11)

(iii) SGHASSTPGGEKETSATQRSSVPSSTEKNAVSMTSSV LSSHSPGSGSSTTQGQDVTLAPATEPASGSAATW (SEQ ID No: 12)

```
       (iv)    SAPDNRPAL (SEQ ID No: 13)

(v)     NSSLEDPSTDYYQELQRDISE (SEQ ID No: 14)

(vi)    TQFNQYKTEAASRVNL (SEQ ID No: 15)

(vii)   AVCQCRRKNYGQLDIFPARDTYH (SEQ ID No: 16)

(viii)  YVPPSSTDRSPYEKVSAGNG (SEQ ID No: 17).
```

5. A mutant, variant or derivative of the immunogenic peptide, protein or portion thereof according to claim 4.

6. The immunogenic peptide, protein or portion thereof of claim 1, wherein at least one amino acid is glycosylated.

7. A compound comprising a conjugate between an immunogenic peptide, protein or portion thereof which is effective to elicit an immune response comprising an amino acid sequence of non VNTR, non leader regions of mucin and carbohydrate polymer.

8. A compound according to claim 7 wherein the amino acid sequence of the immunogenic peptide, protein or portion thereof is derived from human mucin 1.

9. A compound according to claim 8 wherein said amino acid sequence is derived from HMFG.

10. A compound according to claim 9, wherein the immunogenic peptide, protein or portion thereof comprises one of the following amino acid sequences or an immunogenic fragment thereof:

```
       (i)     TGSGHASSTPGGEKETSATQRSSVP (SEQ ID No:
               10)

(ii)    RSSVPSSTEKNAVSMTSSVL (SEQ ID No: 11)

(iii)   SGHASSTPGGEKETSATQRSSVPSSTEKNAVSMTSSV
               LSSHSPGSGSSTTQGQDVTLAPATEPASGSAATW
               (SEQ ID No: 12)

(iv)    SAPDNRPAL (SEQ ID No: 13)

(v)     NSSLEDPSTDYYQELQRDISE (SEQ ID No: 14)

(vi)    TQFNQYKTEAASRVNL (SEQ ID No: 15)

(vii)   AVCQCRRKNYGQLDIFPARDTYH (SEQ ID No: 16)

(viii)  YVPPSSTDRSPYEKVSAGNG (SEQ ID No: 17).
```

11. A compound according to claim 10, wherein the immunogenic peptide, protein or portion thereof is a mutant, variant or derivative of the peptide, protein or portion thereof.

12. A compound according to claim 7, wherein the immunogenic peptide, protein or portion thereof comprises at least one amino acid which is glycosylated.

13. A compound according to claim 7, wherein the carbohydrate is a polymer comprising mannose.

14. A immunogenic vaccine against disease states which comprises an immunogenic peptide, protein or portion thereof which is effective to elicit an immune response comprising an amino acid sequence of non VNTR, non leader regions of mucin optionally with an adjuvant in association with a pharmaceutically acceptable carrier.

15. A vaccine according to claim 14, wherein the immunogenic peptide, protein or portion thereof comprises one or more amino acids which is glycosylated.

16. A compound comprising a conjugate between native MUC1 and a carbohydrate polymer.

17. A compound according to claim 16, wherein said native MUC1 is human milk fat globule antigen (HMFG).

18. A compound according to claim 16, wherein said carbohydrate polymer is oxidised mannan.

19. An immunogenic vaccine comprising the compound according to claim 16 together with a pharmaceutically acceptable carrier.

20. An immunogenic peptide, protein or portion thereof according to claim 1, the amino acid sequence of which corresponds substantially to that of an epitope of the non-VNTR, non-leader region of a mucin and elicits an immune response to said immunogenic peptide, protein or protein thereof, said epitope being selected from the group consisting of:

| amino acids | 33–103 (SEQ ID No: 12) |
|---|---|
| | 229–237 (SEQ ID No: 13) |
| | 471–493 (SEQ ID No: 16) and |
| | 507–526 (SEQ ID No: 48) of said mucin. |

21. An immunogenic peptide, protein or portion thereof according to claim 1, the amino acid sequence of which corresponds substantially to SGHASSTPGGEKETSATQRSSVPSSTEKNAVSMTSSVLSSH-SPGSGSSTTQGQDVTL APATEPASGSAATW (SEQ ID NO: 12), SAPDNRPAL (SEQ ID NO: 13), AVCQCR-RKNYGQLKIFPARDTYH (SEQ ID NO: 16) and YVPPSSTDRSPYEKVSAGNG (SEQ ID NO: 17) and elicits an immune response to said immunogenic peptide, protein or protein thereof.

22. An immunogenic peptide, protein or portion thereof according to claim 1, the amino acid sequence of which corresponds substantially to AVSMTSSVL (SEQ ID NO: 32), VPSSTEKNA (SEQ ID NO: 40) and NAVSMTSSV (SEQ ID NO: 34) and elicits an immune response to said immunogenic peptide, protein or protein thereof.

* * * * *

SEQUENCE LISTING

<160> NUMBER OF SEQ ID NOS: 69

<210> SEQ ID NO 1
<211> LENGTH: 20
<212> TYPE: PRT
<213> ORGANISM: Homo sapiens

<400> SEQUENCE: 1

Ser Ala Pro Asp Thr Arg Pro Ala Pro Gly Ser Thr Ala Pro Pro Ala
1               5                   10                  15

His Gly Val Thr
            20

<210> SEQ ID NO 2
<211> LENGTH: 23
<212> TYPE: PRT
<213> ORGANISM: Homo sapiens

<400> SEQUENCE: 2

Pro Thr Thr Thr Pro Ile Ser Thr Thr Thr Met Val Thr Pro Thr Pro
1               5                   10                  15

Thr Pro Thr Gly Thr Gln Thr
            20

<210> SEQ ID NO 3
<211> LENGTH: 17
<212> TYPE: PRT
<213> ORGANISM: Homo sapiens

<400> SEQUENCE: 3

His Ser Thr Pro Ser Phe Thr Ser Ser Ile Thr Thr Thr Glu Thr Thr
1               5                   10                  15

Ser

<210> SEQ ID NO 4
<211> LENGTH: 16
<212> TYPE: PRT
<213> ORGANISM: Homo sapiens

<400> SEQUENCE: 4

Thr Ser Ser Ala Ser Thr Gly His Ala Thr Pro Leu Pro Val Thr Asp
1               5                   10                  15

```
<210> SEQ ID NO 5
<211> LENGTH: 8
<212> TYPE: PRT
<213> ORGANISM: Homo sapiens

<400> SEQUENCE: 5

Pro Thr Thr Ser Thr Thr Ser Ala
1               5

<210> SEQ ID NO 6
<211> LENGTH: 23
<212> TYPE: PRT
<213> ORGANISM: Homo sapiens

<400> SEQUENCE: 6

Thr Thr Ala Ala Pro Pro Thr Pro Pro Ala Thr Thr Pro Ala Pro Pro
1               5                   10                  15

Ser Ser Ser Ala Pro Pro Glu
            20

<210> SEQ ID NO 7
<211> LENGTH: 5
<212> TYPE: PRT
<213> ORGANISM: Homo sapiens

<400> SEQUENCE: 7

Ala Pro Asp Thr Arg
1               5

<210> SEQ ID NO 8
<211> LENGTH: 9
<212> TYPE: PRT
<213> ORGANISM: Homo sapiens

<400> SEQUENCE: 8

Ala Pro Asp Thr Arg Pro Ala Pro Gly
1               5

<210> SEQ ID NO 9
<211> LENGTH: 12
<212> TYPE: PRT
<213> ORGANISM: Homo sapiens

<400> SEQUENCE: 9

Asp Thr Arg Pro Ala Pro Gly Ser Thr Ala Pro Pro
1               5                   10

<210> SEQ ID NO 10
<211> LENGTH: 25
<212> TYPE: PRT
<213> ORGANISM: Homo sapiens

<400> SEQUENCE: 10

Thr Gly Ser Gly His Ala Ser Ser Thr Pro Gly Gly Glu Lys Glu Thr
1               5                   10                  15

Ser Ala Thr Gln Arg Ser Ser Val Pro
            20                  25

<210> SEQ ID NO 11
<211> LENGTH: 20
<212> TYPE: PRT
<213> ORGANISM: Homo sapiens

<400> SEQUENCE: 11
```

-continued

Arg Ser Ser Val Pro Ser Ser Thr Glu Lys Asn Ala Val Ser Met Thr
1               5                   10                  15

Ser Ser Val Leu
            20

<210> SEQ ID NO 12
<211> LENGTH: 71
<212> TYPE: PRT
<213> ORGANISM: Homo sapiens

<400> SEQUENCE: 12

Ser Gly His Ala Ser Ser Thr Pro Gly Gly Glu Lys Glu Thr Ser Ala
1               5                   10                  15

Thr Gln Arg Ser Ser Val Pro Ser Ser Thr Glu Lys Asn Ala Val Ser
            20                  25                  30

Met Thr Ser Ser Val Leu Ser Ser His Ser Pro Gly Ser Gly Ser Ser
        35                  40                  45

Thr Thr Gln Gly Gln Asp Val Thr Leu Ala Pro Ala Thr Glu Pro Ala
    50                  55                  60

Ser Gly Ser Ala Ala Thr Trp
65                  70

<210> SEQ ID NO 13
<211> LENGTH: 9
<212> TYPE: PRT
<213> ORGANISM: Homo sapiens

<400> SEQUENCE: 13

Ser Ala Pro Asp Asn Arg Pro Ala Leu
1               5

<210> SEQ ID NO 14
<211> LENGTH: 21
<212> TYPE: PRT
<213> ORGANISM: Homo sapiens

<400> SEQUENCE: 14

Asn Ser Ser Leu Glu Asp Pro Ser Thr Asp Tyr Tyr Gln Ile Asp Gln
1               5                   10                  15

Arg Asp Ile Ser Glu
            20

<210> SEQ ID NO 15
<211> LENGTH: 16
<212> TYPE: PRT
<213> ORGANISM: Homo sapiens

<400> SEQUENCE: 15

Thr Gln Phe Asn Gln Tyr Lys Thr Glu Ala Ala Ser Arg Val Asn Leu
1               5                   10                  15

<210> SEQ ID NO 16
<211> LENGTH: 23
<212> TYPE: PRT
<213> ORGANISM: Homo sapiens

<400> SEQUENCE: 16

Ala Val Cys Gln Cys Arg Arg Lys Asn Tyr Gly Gln Leu Asp Ile Phe
1               5                   10                  15

Pro Ala Arg Asp Thr Tyr His
            20

```
<210> SEQ ID NO 17
<211> LENGTH: 20
<212> TYPE: PRT
<213> ORGANISM: Homo sapiens

<400> SEQUENCE: 17

Tyr Val Pro Pro Ser Ser Thr Asp Arg Ser Pro Tyr Glu Lys Val Ser
 1               5                  10                  15

Ala Gly Asn Gly
            20

<210> SEQ ID NO 18
<211> LENGTH: 9
<212> TYPE: PRT
<213> ORGANISM: Homo sapiens

<400> SEQUENCE: 18

Tyr Tyr Gln Glu Leu Gln Arg Asp Ile
 1               5

<210> SEQ ID NO 19
<211> LENGTH: 21
<212> TYPE: PRT
<213> ORGANISM: Homo sapiens

<400> SEQUENCE: 19

Cys Pro Ala His Gly Val Thr Ser Ala Pro Asp Thr Arg Pro Ala Pro
 1               5                  10                  15

Gly Ser Thr Ala Pro
            20

<210> SEQ ID NO 20
<211> LENGTH: 20
<212> TYPE: PRT
<213> ORGANISM: Homo sapiens

<400> SEQUENCE: 20

Pro Ala His Gly Val Thr Ser Ala Pro Asp Thr Arg Pro Ala Pro Gly
 1               5                  10                  15

Ser Thr Ala Pro
            20

<210> SEQ ID NO 21
<211> LENGTH: 18
<212> TYPE: PRT
<213> ORGANISM: Homo sapiens

<400> SEQUENCE: 21

Lys Thr Leu Val Leu Gly Lys Glu Gln Glu Ser Ala Glu Leu Pro Cys
 1               5                  10                  15

Glu Tyr

<210> SEQ ID NO 22
<211> LENGTH: 19
<212> TYPE: PRT
<213> ORGANISM: Homo sapiens

<400> SEQUENCE: 22

Ser Ala Pro Asp Thr Arg Pro Ala Pro Gly Ser Thr Ala Pro Pro Ala
 1               5                  10                  15

His Val Thr
```

```
<210> SEQ ID NO 23
<211> LENGTH: 21
<212> TYPE: PRT
<213> ORGANISM: Homo sapiens

<400> SEQUENCE: 23

Pro Asp Thr Arg Pro Ala Pro Gly Ser Thr Ala Pro Pro Ala His Gly
 1               5                  10                  15

Val Thr Ser Ala Pro
            20

<210> SEQ ID NO 24
<211> LENGTH: 8
<212> TYPE: PRT
<213> ORGANISM: Homo sapiens

<400> SEQUENCE: 24

Ser Ile Ile Asn Phe Glu Lys Leu
 1               5

<210> SEQ ID NO 25
<211> LENGTH: 9
<212> TYPE: PRT
<213> ORGANISM: Homo sapiens

<400> SEQUENCE: 25

Arg Ala His Tyr Asn Ile Val Thr Phe
 1               5

<210> SEQ ID NO 26
<211> LENGTH: 9
<212> TYPE: PRT
<213> ORGANISM: Homo sapiens

<400> SEQUENCE: 26

Asn Tyr Gly Gln Leu Asp Ile Phe Pro
 1               5

<210> SEQ ID NO 27
<211> LENGTH: 9
<212> TYPE: PRT
<213> ORGANISM: Homo sapiens

<400> SEQUENCE: 27

Tyr Gly Gln Leu Asp Ile Phe Pro Ala
 1               5

<210> SEQ ID NO 28
<211> LENGTH: 9
<212> TYPE: PRT
<213> ORGANISM: Homo sapiens

<400> SEQUENCE: 28

Lys Asn Tyr Gly Gln Leu Asp Ile Phe
 1               5

<210> SEQ ID NO 29
<211> LENGTH: 9
<212> TYPE: PRT
<213> ORGANISM: Homo sapiens

<400> SEQUENCE: 29

Ser Ala Pro Asp Thr Arg Pro Ala Pro
 1               5
```

<210> SEQ ID NO 30
<211> LENGTH: 9
<212> TYPE: PRT
<213> ORGANISM: Homo sapiens

<400> SEQUENCE: 30

Gly Tyr Lys Asp Gly Asn Glu Tyr Ile
 1               5

<210> SEQ ID NO 31
<211> LENGTH: 25
<212> TYPE: PRT
<213> ORGANISM: Homo sapiens

<400> SEQUENCE: 31

Arg Lys Ser Ile Arg Ile Gln Arg Gly Pro Gly Arg Ala Phe Val Thr
 1               5                  10                  15

Ile Gly Lys Gly Lys Gly Lys Gly Tyr
            20                  25

<210> SEQ ID NO 32
<211> LENGTH: 9
<212> TYPE: PRT
<213> ORGANISM: Homo sapiens

<400> SEQUENCE: 32

Ala Val Ser Met Thr Ser Ser Val Leu
 1               5

<210> SEQ ID NO 33
<211> LENGTH: 9
<212> TYPE: PRT
<213> ORGANISM: Homo sapiens

<400> SEQUENCE: 33

Thr Thr Gln Gly Gln Asp Val Thr Leu
 1               5

<210> SEQ ID NO 34
<211> LENGTH: 9
<212> TYPE: PRT
<213> ORGANISM: Homo sapiens

<400> SEQUENCE: 34

Asn Ala Val Ser Met Thr Ser Ser Val
 1               5

<210> SEQ ID NO 35
<211> LENGTH: 9
<212> TYPE: PRT
<213> ORGANISM: Homo sapiens

<400> SEQUENCE: 35

Thr Ser Ala Thr Gln Arg Ser Ser Val
 1               5

<210> SEQ ID NO 36
<211> LENGTH: 9
<212> TYPE: PRT
<213> ORGANISM: Homo sapiens

<400> SEQUENCE: 36

Ser Ser Thr Thr Gln Gly Gln Asp Val

<210> SEQ ID NO 37
<211> LENGTH: 9
<212> TYPE: PRT
<213> ORGANISM: Homo sapiens

<400> SEQUENCE: 37

Ser Val Pro Ser Ser Thr Glu Lys Asn
1               5

<210> SEQ ID NO 38
<211> LENGTH: 9
<212> TYPE: PRT
<213> ORGANISM: Homo sapiens

<400> SEQUENCE: 38

Glu Pro Ala Ser Gly Ser Ala Ala Thr
1               5

<210> SEQ ID NO 39
<211> LENGTH: 9
<212> TYPE: PRT
<213> ORGANISM: Homo sapiens

<400> SEQUENCE: 39

Ser Pro Gly Ser Gly Ser Ser Thr Thr
1               5

<210> SEQ ID NO 40
<211> LENGTH: 9
<212> TYPE: PRT
<213> ORGANISM: Homo sapiens

<400> SEQUENCE: 40

Val Pro Ser Ser Thr Glu Lys Asn Ala
1               5

<210> SEQ ID NO 41
<211> LENGTH: 9
<212> TYPE: PRT
<213> ORGANISM: Homo sapiens

<400> SEQUENCE: 41

Thr Pro Gly Gly Glu Lys Glu Thr Ser
1               5

<210> SEQ ID NO 42
<211> LENGTH: 9
<212> TYPE: PRT
<213> ORGANISM: Homo sapiens

<400> SEQUENCE: 42

Cys Arg Arg Lys Asn Tyr Gly Gln Leu
1               5

<210> SEQ ID NO 43
<211> LENGTH: 9
<212> TYPE: PRT
<213> ORGANISM: Homo sapiens

<400> SEQUENCE: 43

Ala Pro Gly Ser Thr Ala Pro Pro Ala
1               5

<210> SEQ ID NO 44
<211> LENGTH: 9
<212> TYPE: PRT
<213> ORGANISM: Homo sapiens

<400> SEQUENCE: 44

Ser Thr Glu Lys Asn Ala Val Ser Met
1               5

<210> SEQ ID NO 45
<211> LENGTH: 9
<212> TYPE: PRT
<213> ORGANISM: Homo sapiens

<400> SEQUENCE: 45

Ser Thr Ala Pro Pro Ala His Gly Val
1               5

<210> SEQ ID NO 46
<211> LENGTH: 32
<212> TYPE: PRT
<213> ORGANISM: Homo sapiens

<400> SEQUENCE: 46

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
                20                  25                  30

<210> SEQ ID NO 47
<211> LENGTH: 30
<212> TYPE: PRT
<213> ORGANISM: Homo sapiens

<400> SEQUENCE: 47

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr
                20                  25                  30

<210> SEQ ID NO 48
<211> LENGTH: 21
<212> TYPE: PRT
<213> ORGANISM: Homo sapiens

<400> SEQUENCE: 48

Cys Tyr Val Pro Pro Ser Ser Thr Asp Arg Ser Pro Tyr Glu Lys Val
1               5                   10                  15

Ser Ala Gly Asn Gly
                20

<210> SEQ ID NO 49
<211> LENGTH: 19
<212> TYPE: PRT
<213> ORGANISM: Homo sapiens

<400> SEQUENCE: 49

Lys Thr Leu Val Leu Gly Lys Glu Gln Glu Ser Ala Glu Leu Pro Cys
1               5                   10                  15

Glu Cys Tyr

<210> SEQ ID NO 50

```
<211> LENGTH: 16
<212> TYPE: PRT
<213> ORGANISM: Homo sapiens

<400> SEQUENCE: 50

Thr Gly Phe Asn Gln Tyr Lys Thr Glu Ala Ala Ser Arg Tyr Asn Leu
1               5                   10                  15

<210> SEQ ID NO 51
<211> LENGTH: 9
<212> TYPE: PRT
<213> ORGANISM: Homo sapiens

<400> SEQUENCE: 51

Cys Tyr Val Pro Pro Ser Ser Thr Asp
1               5

<210> SEQ ID NO 52
<211> LENGTH: 9
<212> TYPE: PRT
<213> ORGANISM: Homo sapiens

<400> SEQUENCE: 52

Val Pro Pro Ser Ser Thr Asp Arg Ser
1               5

<210> SEQ ID NO 53
<211> LENGTH: 9
<212> TYPE: PRT
<213> ORGANISM: Homo sapiens

<400> SEQUENCE: 53

Arg Ser Pro Tyr Glu Lys Val Ser Ala
1               5

<210> SEQ ID NO 54
<211> LENGTH: 9
<212> TYPE: PRT
<213> ORGANISM: Homo sapiens

<400> SEQUENCE: 54

Gln Phe Asn Gln Tyr Lys Thr Glu Ala
1               5

<210> SEQ ID NO 55
<211> LENGTH: 9
<212> TYPE: PRT
<213> ORGANISM: Homo sapiens

<400> SEQUENCE: 55

Gln Tyr Lys Thr Glu Ala Ala Ser Arg
1               5

<210> SEQ ID NO 56
<211> LENGTH: 9
<212> TYPE: PRT
<213> ORGANISM: Homo sapiens

<400> SEQUENCE: 56

Thr Glu Ala Ala Ser Arg Val Asn Leu
1               5

<210> SEQ ID NO 57
<211> LENGTH: 9
<212> TYPE: PRT
```

<213> ORGANISM: Homo sapiens

<400> SEQUENCE: 57

Phe Asn Gln Tyr Lys Thr Glu Ala Ala
1               5

<210> SEQ ID NO 58
<211> LENGTH: 9
<212> TYPE: PRT
<213> ORGANISM: Homo sapiens

<400> SEQUENCE: 58

Asn Ser Ser Leu Glu Asp Pro Ser Thr
1               5

<210> SEQ ID NO 59
<211> LENGTH: 9
<212> TYPE: PRT
<213> ORGANISM: Homo sapiens

<400> SEQUENCE: 59

Asp Pro Ser Thr Asp Tyr Tyr Gln Glu
1               5

<210> SEQ ID NO 60
<211> LENGTH: 9
<212> TYPE: PRT
<213> ORGANISM: Homo sapiens

<400> SEQUENCE: 60

Pro Ser Thr Asp Tyr Tyr Gln Glu Leu
1               5

<210> SEQ ID NO 61
<211> LENGTH: 9
<212> TYPE: PRT
<213> ORGANISM: Homo sapiens

<400> SEQUENCE: 61

Ser Ser Leu Glu Asp Pro Ser Thr Asp
1               5

<210> SEQ ID NO 62
<211> LENGTH: 9
<212> TYPE: PRT
<213> ORGANISM: Homo sapiens

<400> SEQUENCE: 62

Ser Leu Glu Asp Pro Ser Thr Asp Val
1               5

<210> SEQ ID NO 63
<211> LENGTH: 9
<212> TYPE: PRT
<213> ORGANISM: Homo sapiens

<400> SEQUENCE: 63

Ser Ser Thr Glu Lys Asn Ala Val Ser
1               5

<210> SEQ ID NO 64
<211> LENGTH: 8
<212> TYPE: PRT
<213> ORGANISM: Homo sapiens

```
<400> SEQUENCE: 64

Gly Glu Lys Glu Thr Ser Ala Thr
1               5

<210> SEQ ID NO 65
<211> LENGTH: 9
<212> TYPE: PRT
<213> ORGANISM: Homo sapiens

<400> SEQUENCE: 65

Thr Gly Ser Gly His Ala Ser Ser Thr
1               5

<210> SEQ ID NO 66
<211> LENGTH: 9
<212> TYPE: PRT
<213> ORGANISM: Homo sapiens

<400> SEQUENCE: 66

Lys Glu Thr Ser Ala Thr Gln Arg Ser
1               5

<210> SEQ ID NO 67
<211> LENGTH: 9
<212> TYPE: PRT
<213> ORGANISM: Homo sapiens

<400> SEQUENCE: 67

Ala Pro Pro Ala His Gly Val Thr Ser
1               5

<210> SEQ ID NO 68
<211> LENGTH: 9
<212> TYPE: PRT
<213> ORGANISM: Homo sapiens

<400> SEQUENCE: 68

Thr Ala Pro Pro Ala His Gly Val Thr
1               5

<210> SEQ ID NO 69
<211> LENGTH: 9
<212> TYPE: PRT
<213> ORGANISM: Homo sapiens

<400> SEQUENCE: 69

Pro Asp Thr Arg Pro Ala Pro Gly Ser
1               5
```